(12) United States Patent
Verreck et al.

(10) Patent No.: US 7,241,458 B1
(45) Date of Patent: *Jul. 10, 2007

(54) ANTIVIRAL COMPOSITIONS

(75) Inventors: Geert Verreck, Malle (BE); Lieven Baert, Bruges (BE)

(73) Assignee: Janssen Pharmaceutica N.V. (BE)

( * ) Notice: Subject to any disclaimer, the term of this patent is extended or adjusted under 35 U.S.C. 154(b) by 297 days.

This patent is subject to a terminal disclaimer.

(21) Appl. No.: 10/088,805

(22) PCT Filed: Aug. 31, 2000

(86) PCT No.: PCT/EP00/08522

§ 371 (c)(1),
(2), (4) Date: Mar. 21, 2002

(87) PCT Pub. No.: WO01/22938

PCT Pub. Date: Apr. 5, 2001

(30) Foreign Application Priority Data

Sep. 24, 1999 (EP) .................. 99203128

(51) Int. Cl.
A61K 9/14 (2006.01)
A61K 9/20 (2006.01)
A61K 9/50 (2006.01)
A61K 31/505 (2006.01)
A01N 43/54 (2006.01)

(52) U.S. Cl. .................. 424/489; 424/484; 424/464; 424/497; 424/486; 514/272; 514/274; 514/275; 544/323; 544/321; 544/320

(58) Field of Classification Search ................ 424/488, 424/499, 500–1; 514/952
See application file for complete search history.

(56) References Cited

U.S. PATENT DOCUMENTS

| | | | |
|---|---|---|---|
| 2,671,810 A | 3/1954 | Coffman et al. | 260/593 |
| 2,742,466 A | 4/1956 | Randall et al. | 260/249.5 |
| 4,096,206 A | 6/1978 | Boyer | 260/880 |
| 4,450,162 A | 5/1984 | Kamioka et al. | 424/251 |
| 4,652,645 A | 3/1987 | Stingelin et al. | 544/198 |
| 4,659,363 A | 4/1987 | Hubele et al. | 71/92 |
| 5,017,466 A | 5/1991 | Kobayasji et al. | 430/558 |
| 5,574,040 A | 11/1996 | Bukrinsky et al. | 514/275 |
| 5,716,722 A | 2/1998 | Hamada et al. | 428/690 |
| 5,837,436 A | 11/1998 | Mihayashi et al. | 430/503 |
| 5,939,099 A * | 8/1999 | Grabowski et al. | |
| 6,107,301 A | 8/2000 | Aldrich et al. | 514/258 |
| 6,197,779 B1 * | 3/2001 | Andries et al. | |
| 6,342,503 B1 | 1/2002 | Aldrich et al. | 514/272 |

FOREIGN PATENT DOCUMENTS

| | | |
|---|---|---|
| DE | 2 038 182 | 2/1972 |
| DE | 26 11 826 | 9/1976 |
| EP | 0 145 656 B1 | 5/1985 |
| EP | 0 270 111 A1 | 6/1988 |
| EP | 0 541 966 A2 | 5/1993 |
| EP | 0 588 762 A1 | 3/1994 |
| EP | 0 795 549 A1 | 9/1997 |
| EP | 0 834 507 A1 | 4/1998 |
| EP | 0 872 233 A1 | 10/1998 |
| EP | 0872233 | * 10/1998 |
| EP | 0 945 443 A1 | 9/1999 |
| EP | 0 945 447 A1 | 9/1999 |
| FR | 2099730 A | 3/1972 |
| FR | 2 398 740 | 3/1979 |
| FR | 2 400 535 | 4/1979 |
| GB | 1 010 998 | 11/1965 |
| GB | 1 477 349 | 6/1977 |
| HU | 211 774 | 12/1995 |
| JP | 02 052 360 | 2/1990 |
| JP | 2-286666 | 11/1990 |
| JP | 02 300 264 | 12/1990 |
| JP | 08 199 163 | 8/1996 |
| JP | 09 068 784 | 3/1997 |
| JP | 11-116555 | 4/1999 |
| SU | 143 808 | 1/1962 |
| WO | 91/18887 | 12/1991 |
| WO | WO 94/00513 | 1/1994 |
| WO | WO 94/02470 | 2/1994 |
| WO | 95/10506 | 4/1995 |
| WO | WO 95/15952 | 6/1995 |
| WO | WO 97/10887 | 3/1997 |
| WO | WO 97/19065 | 5/1997 |
| WO | WO 98/41512 | 9/1998 |

OTHER PUBLICATIONS

Ashley et al., "The Search for Chemotherapeutic Amidines. Part XVI. Amidinoanilino-1,3,5-triazines and Related Compounds," *J. Chem. Soc.*, Jan. 1, 1960, 4525-4532.

Koyanagi et al., "Selective Cytotoxicity of Aids Virus Infection Towards HTLV-1-Transformed Cell Lines," *Int. J. Cancer*, 1985, 36, 445-451.

Martindale, *The Extra Pharmacopoeia*, 29th edition, p. 1435.

Prakash, L. et al, "Synthesis of some new trisubstituted derivatives of 2,4,6-trichloro-1,3,5-triazine and their anti-bacterial activity," *Pharmazie*, 1990, 45(4), 284.

Ghosh, D. et al., "2,4-Bis(arylamino)-5-methylpyrimidines as Antimicrobial Agents," *J. Med. Chem.*, 1969, 10, 974-975.

(Continued)

*Primary Examiner*—Sreeni Padmanabhan
*Assistant Examiner*—Jake M. Vu

(57) ABSTRACT

The present invention is concerned with pharmaceutical compositions of antiviral compounds which can be administered to a mammal, in particular a human, suffering from a viral infection. These compositions comprise particles obtainable by melt-extruding a mixture comprising one or more antiviral compounds and one or more appropriate water-soluble polymers and subsequently milling said melt-extruded mixture.

32 Claims, No Drawings

OTHER PUBLICATIONS

Chen, C., "Design and Synthesis of a Series of Non-Peptide High-Affinity Human Corticotropin-Releasing Factor Receptor Antagonists," *J. Med. Chem.*, 1996, 39(22), 4358-4360.

International Search Report issued in International Application No. PCT/EP00/08522, Date of Mailing: Jan. 2, 2001.

J. W. F. McOmie (ed.), *Protective Groups in Organic Chemistry*, Plenum Press, 1973.

T. W. Greene & P. G. M. Wutz (eds.), *Protective Groups in Organic Synthesis*, 2nd edition, Wiley Interscience, 1991, pp. 473.

*CRC Handbook*, 64th edition, p. F-114.

Shaihla, M. et al., "Synthesis of some new fluorinated derivatives of 1,3,5-triazine as potential biologically active agents," Chem. Abstr., 1990, 112(1), abstract No. 7458v, p. 733.

Kreutzberger, A. et al., "Anticonvulsives. IV. 2,4,6- mixed functional substituted 1,3,5-triazines," Chem. Abstr., 1988, 108(15), abstract No. 131766a, p. 752.

Langalia, N. A. et al., "Studies on antitubercular agents. Part III. Preparation of some p-(2,4-diarylamino-6-S-triazinylamino)-benzaldehyde/acetophenone thiosemicarbazones as potential tuberculostatic agents," Chem. Abstr., 1983, 98(11), abstract No. 89321z, p. 556.

Unishi, T. et al., "Preparation of polypyromellitimides containing dialkylamino-type melamine units," Chem. Abstr., 1981, 95(4), 25685b, p. 3.

Ghosh, D., "2,4-Bis(arylamino)-6-methylpyrimidines as antimicrobial agents," Chem. Abstr. 1981, 95(11), 97712f, p. 648.

Parekh, H. et al., "Optically active s-triazine derivatives. I. Preparation of D(x)-2,4-diarylamino-6-α-carboxybenzylamino-s-triazines," Chem. Abstr., 1975, 83(23), 193239e, p. 460.

Acharya, J.N. et al., Studies on *s*-Triazinyl Compounds as Potential Medicinal Agents. Part I, *J. Indian Chem. Soc.*, Feb. 1976, vol. LII, 1190-1192.

Acharya, J.N. et al., Studies on *s*-Triazinyl Compounds as Potential Medicinal Agents. Part II, *J. Indian Chem. Soc.*, Feb. 1976, vol. LIII, 193-195.

Arutyunyan, E.A. et al., "Reaction of Uracils with Phosphoric Acid Amides", *Institute Org., Khim. Im Zelinskogo. IZV. Akad. Nauk SSSR, Ser Khim.*, 1970, 4, 904-909 English language abstract provided.

Fernandes, Y., et al., "Studies on *s*-Triazine Part VI: 2,4-Bisalyklamino 6 (Phenyl Azoaryl Hydrazino)-s-Triazine", *J. Inst. Chemists (India)*, May 1991, 63, 103-104.

Campbell, J.R. et al., "Unsymmetrically Substituted Melamines", *J. Org. Chem.*, 1961, 26, 2786-2789.

Chen, C. et al., "Design and Synthesis of a Series of Non-Peptide High-Affinity Human Corticotropin-Releasing Factor 1 Receptor Antagonists", *J. Med. Chem.*, 1996, 39, 4358-4360.

Freiberg, R. et al., "Synthese von 2,4-Bisalkyl(aryl)amino-6-Cyanamino-1,3,5-Triazinen", *J. Prakt. Chem*, 1985, 327(3), 471-478.

Ghosh, D., "2,4-Bis (Arylamino)-6-Methyl Pyrimidines as Antimicrobial Agents", *J. Indian Chem. Soc.*, May 1981, vol. LVIII, 512-513.

Ghosh, D., "2,4-Bis(Arylamino)Pyrimidines as Antimicrobial Agents", *J. Med Chem.*, 1966, 9(3), 423-424.

Ghosh, D. et al., "2,4 Bis(*p*-Chloroanilino)-Pyrimidine, an Uncoupler of Oxidative Phosphorylation" *FEBS Letters*, 4(3), 157-159.

Ghosh, D. et al., "2,4-Bis(arylamino)-5-Methylpyrimidines as Antimicrobial Agents", *J. Med. Chem.*, 1967, 10(5), 974-975.

Ghoneim, K.M. et al., "Synthesis and Evaluation of Some 2,4 and 2,4-Disubstituted-6-Methylpyrimidine Derivatives for Antimicrobial Activity", *Egypt J. Pharm Sci.*, 1978, 28(1-4), 117-126.

Goghari, M.H. et al., "Studies on s-Triazinyl Aryl/Alkyl Sulphones. Part 1, Preparation of 4'(2-*p*-Chlorophenylsulphonyl-4- Aryl/Alkyl Amino-s-Triazin-6-yl)-Aminobenzoic Acid", *J. Indian Chem Soc.*, 1976, 53(2), 207-208.

Goghari, M.H. et al., Studies on s-Triazinyl Aryl/Alkyl Sulphones Part-III, *Def Sci J.*, 1977, 27(3), 141-144.

Inoue, et al, "Synthesis of 2-(p-Aminophenyiazo)-1,3,5-Triazine Derivatives", *Nippon Kagaku Kaishi*, 1981, 12, 1922-1928 (English Abstract).

Kamdar, G.C. et al., "Preparation and Antibacterial Activity of 2-Phenyl-3-(2', 4'-Diarylamino-*s*-Triazin-6-yl)-5/H/Ch3-Carboxymethyl-4-thiazolidinone and 2-Aryl-3-(*p*-Aminosulphophenyl/2'-Pyrimidylaminosulphopheynyl)-*p*-Carboxymethyl-4-Thiazolidinones", *J. Indian Chem. Soc.*, May 1987, vol. LXIV, 298-301.

Inoue, Y. et al., "Synthesis of *p*-Nitrophenylazo-s-Triazines", *Yuki Gosei Kagaku Kyokaishi*, 1978, 36(9), 779-793.

Honda, I., "Synthesis of Arylmelamines. II. Synthesis of Diarymelamines", *Yuki Gosei Kagaku Kyokaishi*, 1962, 20, 460-465 (English Abstract).

*London Rubber Industries Ltd.'s Patent (Manner of Manufacture P.A.T.)*, Reports of Patent, Design and Trademark Cases, 1968, In the Appeal Tribunal *Before* R. Justice Lloyd-Jacob, 31-35.

L'Oreal's Application, Patent Appeal Tribunal, 1970, 20, R.P.C., In the Appeal Tribunal *Before*: Mr. Justice Graham and Mr. Justice Whitford, 565-573.

Ghoneim, et al., "Synthesis and Evaluation of some 2-,4- and 2,4-di-substituted-6-Methylpyrimidine Derivatives for Antimicrobial Activity", *J. Indian Chem Soc.*, 1986, 63(10), 914-917.

Coats, E. et al., "Correlation Analysis of Pyrimidine Folic Acid Antagonists as Antibacterial", *Eur. J. Med. Chem- Chim. Ther.*, 1979, 14(3), 26-27.

O'Brien, et al., Pyrimidines-(VIII), 2-Amino-4-(Substituted Anilino) Pyrimidines, CAOLD, 1986, 46-47.

Rajnani, H.B et al., "Studies on Thioureas. Part I: Preparation and Antibacterial Activity of [[2,4-bis(arylamino)-s-triazin-6-yl])Aminoacyl]Phenylthioureas", *Chemical Abstracts*, 1978, 88, 500, 88-37757v.

Folkers, J. et al., "Designing Ordered Molecular Arrays in Two and Three Dimensions", *ACS Symp. Ser.*, 1992, 499(Supramol. Archit), 10-23, Abstract Only, 1 page.

Kreutzberger, A.et al., "Herbizide, V1 [1], Kernfluorierte 2,4-Dianilino-6-(Diehexylamino)-1,3,5-Triazine", *Journal of Fluorine Chemistry*, 1985, 30, 329-341.

Kutepov, D.F. et al., "Synthesis and Investigation of Symmetrical Triazines", *Journal Gen Chemical (USSR)*, 1962, 32, 1557-1558.

LaBrecque, C. et al., "Substituted Melamines as Chemosterilants of House Flies", *Journal of Econ. Entomol*,1968, 61(6), 1621-1632.

Mehta, L. et al., Studies of S-Triazines Part I: Preparation of 2,4-Diarylamino-6-N, N-Diethylaminoethylamino/N,N-Diethylamino Ethoxy-S-Triazines, *J. Inst. Chemists(India)*, 1987, 59, 183-185.

Mehta, L. et al., "Studies of s-Triazines. Part II: Preparation of 2,4-Diaryl-Amino-6-Carbethoxymethylamino and 4-(2', 4'-Diarylamino-s-Triazin-6'-yl)Aminoantipyrine", *Journal of Indian Chem Soc.*, 1986, 63(4), 414-416.

Mehta, L. et al., "Studies on 1,3,4-Oxadiazoles. Part IV. Preparation of 2-Aryl-5(2',4'-bis-p-chlorophenyl-amino-s-triazin-6'ylaminomethyl)-1,3,4-Oxadiazoles", *J. Indian Chem Soc.*, 1987, 64(12), 770-771.

Ostroverkhov, V.G. et al., "Preparation and Reactivity of some Diisocynates—1,3,5-Triazine Derivatives", *Inst. Khim. Vysokomol, Sin Fiz Khim Polim*, 1968, 5, 59-65 English Abstract Provided.

Pandya, U.H. et al., Studies of Cyanuric Chloride Derivatives Part (II), *J. Inst. Chemists (India)*, 1981, 53, 81-82.

Pandya, K.S. et al., "s-Triazinyl Derivatives as Medicinal Agents", *J. Inst Chemists(India)*, 1976, 48(pt5), 245-247.

Pandya, U.H. et al., "Studies on Cyanuric Chloride Derivatives Part-(III)", *J. Inst. Chemists(India)*, 1981, 53, 83-84.

Pandya, K. S. et al., "Studies on Potential Drugs: Potential Anthelmintics Part I", *J. Inst Chemists(India)*, 1975, 47(6), 235-237.

Pathe, P.P. et al., "On 1,3,5-Triazines. Part-II: Synthesis of 2,4-Dithio-3,5- Diaryl-6-Phenylimino-Hexahydro-1,3,5-triazines and 2,6-Dithio-3,5-Diaryl-4-Phenylimino-Hexahydro-1,3,5-Triazines", *J. Indian Chem. Soc.*, 1982, 59(5), 670-672.

Prakash, L. et al., "Synthesis of some New Trisubstituted Derivatives of 2,4,6-Trichloro-1,3,5-Triazine and their Anti-Bacterial Activity", *Pharmize*, 1990, 45(4), 284.

Rajnani, H.B. et al., "Studies on Thioureas-Part-I: Preparation and Antibacterial Activity of 2,4-iarylamino-s-Triazin-6-yl-Aminoacyl Phenylthioureas", *J. Inst. Chemists(India)*, 1977, 49(4), 222-224.

Rajnani, H.B. et al., "Studies on Ureas: Part-I-Preparation of 2, 4-Diarylamino-s-Triazin-6-YL-AMinoacyl Phenylureas", *J. Inst. Chemists(India)*, 1976, 48(5), 254-255.

Sen, D. et al., "Pyrimidines: Part IX:Synthesis of Some is(arylamino) Pyrimidines", *J. Indian Chem. Soc.*, 1975, 52(8), 774-775.

Shaihla, et al., "Synthesis of some New Flurinated Derivatives of 1,3,5-Triazine as Potential Biologically Active Agents", *J. Indian Chem. Soc.*, 1989, 66(5), 352-353.

Shaihla, et al., "Synthesis and Spectroscopic Studies of some Fluorinated 1,3,5-Triazine Derivatives", *Journal of Fluorine Chemistry*, 1988, 39, 117-123.

Shealy, Y. et al., "*v*-Triazolo[4,5-*d*]pyrimidines. I. Synthesis and Nucleophilic Substitution of 7-Chloro Derivatives of 3-Substituted *v*-Triazolo[4,5-*d*]pyrimidines", *J. Org. Chem.*, 1961, 26, 4433-4440.

Strukov, O.G. et al., Infrared Spectra and Structure of some Secondary Amines(Derivatives of Cyanuric Chloride and Substituted Aniline), *Zh. Strukt. Khim,* 1965, 6(2), 218-226 English Language Abstract Provided.

Tyagi, E. et al., "Heterocyclic Compounds, Synthesis of Some Flurinated 1,3,5-Triazine Derivatives", *Rev Roum Chim*, 1990, 35(10-12), 1025-1029.

Wakabayashi, K. et al., "Inhibitory Effects of s-Triazines on the Nitrification in Soil. III. Diamino-s-triazines and Melanines", *Nippon Dojo-Hiryogaku Zasshi*, 1970, 41(5), 193-200 English Language Abstract Provided.

Zerkowski, J.A. et al., "Design of Organic Structures in the Solid State: Hydrogen-Bonded Molecular Tapes", *J. Am. Chem. Soc.*, 1990, 112, 9025-9026.

Zerkowski, J.A. et al., "Polymorphic Packing Arrangements in a Class of Engineered Organic Crystals", *Chem Mater.*, 1997, 9, 1933-1941.

Zerkowski, J.A. et al., "Investigation into the Robustness of Secondary and Tertiary Architecture of Hydrogen-Bonded Crystalline Tapes", *Chem. Matter*, 1994, 6, 1250-1257.

Chase, B.H. et al., "The Synthesis of Some Potential Antibacterial Agents", *J. Pharm. Pharmacol*, 1964, 16(3), 163-173.

Honda, I. et al., "Synthesis and Oxidation of Hyrrazino-s-Trizines. I. Synthesis and Oxidation of Anilinomelamines", *Kogyo Kagaku Zasshi,Journal of the Chemical Society of Japan. Industrial Chemistry Section*, 1965, 68(2), 311-314 English language abstract provided.

Parasharya, P.M. et al., "Studies on s-Triazines: Part XIV Preparation and Antimicrobial Activity of 2,4-Diarylamino 6_Dimethylaminoethyl-Amino s-Triazines", *Acta Ciencia Indica. Chem*, 1985, 11(1), 66-70 Brit 701-789.

Patwa, B.S. et al., "Preparation of 2,4-Diarylamino-s-Triazin-6-yl-Phenylsulphones. Part I", *Chemical Era*, 1975, 11(6), 17-18.

Mehta, S.S.B.et al., Preparation of s-Triazinyl artl Sulphones as Antibacterial Agents (II), *Chemical Era*, 1978, 14(8), 328-329.

Kreutzberger, V.A. et al., "Anticonvulsives. IV. 2,4,6-Mixed Functional Substituted 1,3,5-Triazines" *Chemiker-Zeitung*, 1987, 111(7-8), 241-245 English language abstract provided.

\* cited by examiner

ANTIVIRAL COMPOSITIONS

CROSS-REFERENCE TO RELATED APPLICATIONS

This application is a national stage application of patent application No. PCT/EP05/15398, filed Jul. 11, 2005, which application claims priority from EP patent application No.04103368.9, filed Jul. 14, 2004, each of which is hereby incorporated by reference.

The present invention concerns pharmaceutical compositions of antiviral compounds which can be administered to a mammal, in particular a human, suffering from a viral infection. These compositions comprise particles obtainable by melt-extruding a mixture comprising one or more antiviral compounds and one or more appropriate water-soluble polymers and subsequently milling said melt-extruded mixture.

The antiviral compounds constituting the pharmaceutical compositions of the present invention are dispersed in a carrier by melt-extrusion to obtain a solid dispersion in order to improve their bio-availability.

Compounds structurally related to the present antiviral compounds are disclosed in the prior art.

Pharmazie (1990), 45(4), p 284 discloses trisubstituted derivatives of 2,4,6-trichloro-1,3,5-triazine having anti-bacterial activity.

Chem. Abstr. (1990), 112, no. 1 concerns synthesis of fluorinated derivatives of 1,3,5-triazine as potential bactericidal agents.

Chem. Abstr. (1988), 108, no. 15 describes 2,4,6-mixed functional substituted 1,3,5-triazines as anti-convulsives.

Chem. Abstr. (1983), 98, no. 11 concerns the preparation of p-(2,4-diarylamino-6-S-triazinylamino)-benzaldehyde/acetophenone thiosemicarbazones as potential tuberculostatic agents.

Chem. Abstr. (1981), 95, no. 4 describes the preparation of polypyromellitimides containing dialkylamino-type melamine units.

Chem. Abstr. (1975), 83, no. 23 describes optically active S-triazine derivatives.

FR-A-2099730 concerns diamino-, and dinitro-5-triazines, which can be used for the preparation of polymeric material and colorants.

EP-A-0795549 discloses bis-aryloxy(amino)-triazinyl-oxy (amino)aryl derivatives as antiviral agents.

Ashley et al. (J. Chem. Soc. (1960), January 1, pp 4525–4532) describes amidinoanilino-1,3,5-triazines having potential trypanocidal activity.

WO 91/18887 discloses diaminopyrimidines as gastric acid secretion inhibitors.

EP-A-0588762 concerns the use of N-phenyl-2-pyrimidinamine derivatives as proteinkinase C-inhibitors and anticancer agents.

WO 95/10506 describes N-alkyl-N-aryl-pyrimidinamines and derivatives thereof as Corticotropin Releasing Factor receptor antagonists.

EP-A-0270111 discloses pyrimidine derivatives as fungicides in agricultural and horticultural compositions.

J. Med. Chem. (1969), 10, pp 974–975 describes 2,4-bis (arylamino)-5-methyl-pyrimidines and Chem. Abstr. (1981), 95, no. 11 describes 2,4-bis(arylamino)-6-methylpyrimidines as antimicrobial agents.

J. Med. Chem. (1996), 39, pp 43584360 deals with 4-anilino-6-aminopyrimidines as non-peptide high affinity human Cortocotropin Releasing Factor, receptor antagonists.

EP-0,834,507 discloses substituted diamino 1,3,5-triazine derivatives having HIV replication inhibiting properties.

The particles of the present invention consist of a solid dispersion comprising (a) an antiviral compound of formula

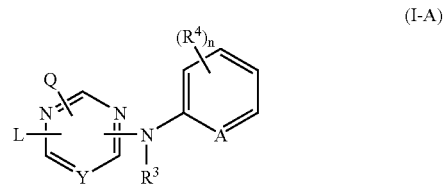

(I-A)

a N-oxide, a pharmaceutically acceptable addition salt or a stereochemically isomeric form thereof, wherein Y is $CR^5$ or N;

A is CH, $CR^4$ or N;

n is 0, 1, 2, 3 or 4;

Q is $-NR^1R^2$ or when Y is $CR^5$ then Q may also be hydrogen;

$R^1$ and $R^2$ are each independently selected from hydrogen, hydroxy, $C_{1-12}$alkyl, $C_{1-12}$alkyloxy, $C_{1-12}$alkylcarbonyl, $C_{1-12}$alkyloxycarbonyl, aryl, amino, mono- or di($C_{1-12}$alkyl)amino, mono- or di($C_{1-12}$alkyl)aminocarbonyl wherein each of the aforementioned $C_{1-12}$alkyl groups may optionally and each individually be substituted with one or two substituents each independently selected from hydroxy, $C_{1-6}$alkyloxy, hydroxy$C_{1-6}$alkyloxy, carboxyl, $C_{1-6}$alkyloxycarbonyl, cyano, amino, imino, aminocarbonyl, aminocarbonylamino, mono- or di($C_{1-6}$alkyl)amino, aryl and Het; or $R^1$ and $R^2$ taken together may form pyrrolidinyl, piperidinyl, morpholinyl, azido or mono- or di($C_{1-12}$alkyl)amino$C_{1-4}$ alkylidene;

$R^3$ is hydrogen, aryl, $C_{1-6}$alkylcarbonyl, $C_{1-6}$alkyl, $C_{1-6}$alkyloxycarbonyl, $C_{1-6}$alkyl substituted with $C_{1-6}$alkyloxycarbonyl; and each $R^4$ independently is hydroxy, halo, $C_{1-6}$alkyl, $C_{1-6}$alkyloxy, cyano, amino carbonyl, nitro, amino, trihalomethyl, trihalomethyloxy, or when Y is $CR^5$ then $R^4$ may also represent $C_{1-6}$alkyl substituted with cyano or aminocarbonyl;

$R^5$ is hydrogen or $C_{1-4}$alkyl;

L is $-X^1-R^6$ or $-X^2$-Alk-$R^7$ wherein $R^6$ and $R^7$ each independently are phenyl or phenyl substituted with one, two, three, four or five substituents each independently selected from halo, hydroxy, $C_{1-6}$alkyl, $C_{1-6}$alkyloxy, $C_{1-6}$alkylcarbonyl, $C_{1-6}$alkyloxycarbonyl, formyl, cyano, nitro, amino, and trifluoromethyl; or when Y is $CR^5$ then $R^6$ and $R^7$ may also be selected from phenyl substituted with one, two, three, four or five substituents each independently selected from aminocarbonyl, trihalomethyloxy and trihalomethyl; or when Y is N then $R^6$ and $R^7$ may also be selected from indanyl or indolyl, each of said indanyl or indolyl may be substituted with one, two, three, four or five substituents each independently selected from halo, hydroxy, $C_{1-6}$alkyl, $C_{1-6}$alkyloxy, $C_{1-6}$alkylcarbonyl, $C_{1-6}$alkyloxycarbonyl, formyl, cyano, nitro, amino, and trifluoromethyl; when $R^6$ is optionally substituted indanyl or indolyl, it is preferably attached to the remainder of the molecule via the fused phenyl ring. For instance, $R^6$ is suitably 4-, 5-, 6- or 7-indolyl;

$X^1$ and $X^2$ are each independently —$NR^3$—, —NH—NH—, —N=N—, —O—, —S—, —S(=O)— or —S(=O)$_2$—;

Alk is $C_{1-4}$alkanediyl; or when Y is $CR^5$ then L may also be selected from $C_{1-10}$alkyl, $C_{3-10}$alkenyl, $C_{3-10}$alkynyl, $C_{3-7}$cycloalkyl, or $C_{1-10}$alkyl substituted with one or two substituents independently selected from $C_{3-7}$cycloalkyl, indanyl, indolyl and phenyl, wherein said phenyl, indanyl and indolyl may be substituted with one, two, three, four or where possible five substituents each independently selected from halo, hydroxy, $C_{1-6}$alkyl, $C_{1-6}$alkyloxy, cyano, aminocarbonyl, $C_{1-6}$alkyloxycarbonyl, formyl, nitro, amino, trihalomethyl, trihalomethyloxy and $C_{1-6}$alkylcarbonyl;

aryl is phenyl or phenyl substituted with one, two, three, four or five substituents each independently selected from halo, $C_{1-6}$alkyl, $C_{1-6}$alkyloxy, cyano, nitro and trifluoromethyl;

Het is an aliphatic or aromatic heterocyclic radical; said aliphatic heterocyclic radical is selected from pyrrolidinyl, piperidinyl, homopiperidinyl, piperazinyl, morpholinyl, tetrahydrofuranyl and tetrahydrothienyl wherein each of said aliphatic heterocyclic radical may optionally be substituted with an oxo group; and said aromatic heterocyclic radical is selected from pyrrolyl, furanyl, thienyl, pyridyl, pyrimidinyl, pyrazinyl and pyridazinyl wherein each of said aromatic heterocyclic radical may optionally be substituted with hydroxy;

or an antiviral compound of formula

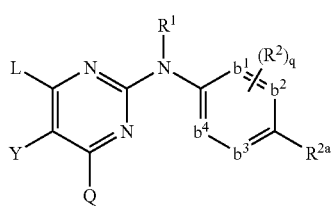

(I-B)

the N-oxides, the pharmaceutically acceptable addition salts, quaternary amines and the stereochemically isomeric forms thereof, wherein -$b^1$=$b^2$-C($R^{2a}$)=$b^3$-$b^4$=represents a bivalent radical of formula —CH=CH—C($R^{2a}$)=CH—CH= (b-1);

—N=CH—C($R^{2a}$)=CH—CH= (b-2);

—CH=N—C($R^{2a}$)=CH—CH= (b-3);

—N=CH—C($R^{2a}$)=N—CH= (b-4);

—N=CH—C($R^{2a}$)=CH—N= (b-5);

—CH=N—C($R^{2a}$)=N—CH= (b-6);

—N=N—C($R^{2a}$)=CH—CH= (b-7);

q is 0, 1, 2; or where possible q is 3 or 4;

$R^1$ is hydrogen, aryl, formyl, $C_{1-6}$alkylcarbonyl, $C_{1-6}$alkyl, $C_{1-6}$alkyloxycarbonyl, $C_{1-6}$alkyl substituted with formyl, $C_{1-6}$alkylcarbonyl, $C_{1-6}$alkyloxycarbonyl;

$R^{2a}$ is cyano, aminocarbonyl, mono- or di(methyl)aminocarbonyl, $C_{1-6}$alkyl substituted with cyano, aminocarbonyl or mono- or di(methyl)aminocarbonyl, $C_{2-6}$alkenyl substituted with cyano, or $C_2$ alkynyl substituted with cyano;

each $R^2$ independently is hydroxy, halo, $C_{1-6}$alkyl optionally substituted with cyano or —C(=O)$R^6$, $C_{3-7}$cycloalkyl, $C_{2-6}$alkenyl optionally substituted with one or more halogen atoms or cyano, $C_{2-6}$alkynyl optionally substituted with one or more halogen atoms or cyano, $C_{1-6}$alkyloxy, $C_{1-6}$alkyloxycarbonyl, carboxyl, cyano, nitro, amino, mono- or di($C_{1-6}$alkyl)amino, polyhalomethyl, polyhalomethyloxy, polyhalomethylthio, —S(=O)$_p$$R^6$, —NH—S(=O)$_p$$R^6$, —C(=O)$R^6$, —NHC(=O)H, —C(=O)NHNH$_2$, —NHC(=O)$R^6$, —C(=NH)$R^6$ or a radical of formula

(c)

wherein each A independently is N, CH or $CR^6$;

B is NH, O, S or $NR^6$;

p is 1 or 2; and $R^6$ is methyl, amino, mono- or dimethylamino or polyhalomethyl;

L is $C_{1-10}$alkyl, $C_{2-10}$alkenyl, $C_{2-10}$alkynyl, $C_{3-7}$cycloalkyl, whereby each of said aliphatic group may be substituted with one or two substituents independently selected from $C_{3-7}$cycloalkyl, indolyl or isoindolyl, each optionally substituted with one, two, three or four substituents each independently selected from halo, $C_{1-6}$alkyl, hydroxy, $C_{1-6}$alkyloxy, cyano, aminocarbonyl, nitro, amino, polyhalomethyl, polyhalomethyloxy and $C_{1-6}$alkylcarbonyl, phenyl, pyridinyl, pyrimidinyl, pyrazinyl or pyridazinyl, wherein each of said aromatic rings may optionally be substituted with one, two, three, four or five substituents each independently selected from the substituents defined in $R^2$; or L is —X—$R^3$ wherein $R^3$ is phenyl, pyridinyl, pyrimidinyl, pyrazinyl or pyridazinyl, wherein each of said aromatic rings may optionally be substituted with one, two, three, four or five substituents each independently selected from the substituents defined in $R^2$; and X is —$NR^1$—, —NH—NH—, —N=N—, —O—, —C(=O)—, —CHOH—, —S—, —S(=O)— or —S(=O)$_2$—;

Q represents hydrogen, $C_{1-6}$alkyl, halo, polyhalo$C_{1-6}$alkyl or —$NR^4R^5$; and $R^4$ and $R^5$ are each independently selected from hydrogen, hydroxy, $C_{1-12}$alkyl, $C_{1-12}$alkyloxy, $C_{1-12}$alkylcarbonyl, $C_{1-12}$alkyloxycarbonyl, aryl, amino, mono- or di($C_{1-12}$alkyl)amino, mono- or di($C_{1-12}$alkyl)aminocarbonyl wherein each of the aforementioned $C_{1-12}$alkyl groups may optionally and each individually be substituted with one or two substituents each independently selected from hydroxy, $C_{1-6}$alkyloxy, hydroxy$C_{1-6}$alkyloxy, carboxyl, $C_{1-6}$alkyloxycarbonyl, cyano, amino, imino, mono- or di($C_{1-6}$alkyl)amino, polyhalomethyl, polyhalomethyloxy, polyhalomethylthio, —S(=O)$_p$R$^6$, —NH—S(=O)$_p$R$^6$, —C(=O)R$^6$, —NHC(=O)H, —C(=O)NHNH$_2$, —NHC(=O)R$^6$, —C(=NH)R$^6$, aryl and Het; or R$^4$ and R$^5$ taken together may form pyrrolidinyl, piperidinyl, morpholinyl, azido or mono- or di($C_{1-12}$alkyl)amino$C_{1-4}$alkylidene;

Y represents hydroxy, halo, $C_{3-7}$cycloalkyl, $C_2$alkenyl optionally substituted with one or more halogen atoms, $C_{2-6}$alkynyl optionally substituted with one or more halogen atoms, $C_{1-6}$alkyl substituted with cyano or —C(=O)R$^6$, $C_{1-6}$alkyloxy, $C_{1-6}$alkyloxycarbonyl, carboxyl, cyano, nitro, amino, mono- or di($C_{1-6}$alkyl)amino, polyhalomethyl, polyhalomethyloxy, polyhalomethylthio, —S(=O)$_p$R$^6$—NH—S(=O)$_p$R$^6$, —C(=O)R$^6$, —NHC(=O)H, —C(=O)NHNH$_2$, —NHC(=O)R$^6$, —C(=NH)R$^6$ or aryl;

aryl is phenyl or phenyl substituted with one, two, three, four or five substituents each independently selected from halo, $C_{1-6}$alkyl, $C_{3-7}$cycloalkyl, $C_{1-6}$alkyloxy, cyano, nitro, polyhalo$C_{1-6}$alkyl and polyhalo$C_{1-6}$alkyloxy;

Het is an aliphatic or aromatic heterocyclic radical; said aliphatic heterocyclic radical is selected from pyrrolidinyl, piperidinyl, homopiperidinyl, piperazinyl, morpholinyl, tetrahydrofuranyl and tetrahydrothienyl wherein each of said aliphatic heterocyclic radical may optionally be substituted with an oxo group; and said aromatic heterocyclic radical is selected from pyrrolyl, furanyl, thienyl, pyridinyl, pyrimidinyl, pyrazinyl and pyridazinyl wherein each of said aromatic heterocyclic radical may optionally be substituted with hydroxy; Het is meant to include all the possible isomeric forms of the heterocycles mentioned in the definition of Het, for instance, pyrrolyl also includes 2H-pyrrolyl; the Het radical may be attached to the remainder of the molecule of formula (I-B) through any ring carbon or heteroatom as appropriate, thus, for example, when the heterocycle is pyridinyl, it may be 2-pyridinyl, 3-pyridinyl or 4-pyridinyl. or an antiviral compound of formula

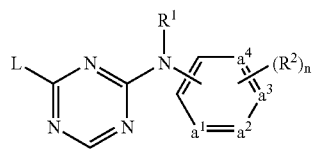

(I-C)

the N-oxides, the pharmaceutically acceptable addition salts, quaternary amines and the stereochemically isomeric forms thereof, wherein -a$^1$=a$^2$-a$^3$=a$^4$- represents a bivalent radical of formula

  (a-1);

  (a-2);

  (a-3);

  (a-4);

  (a-5);

n is 0, 1, 2, 3 or 4; and in case -a$^1$=a$^2$-a$^3$=a$^4$- is (a-1), then n may also be 5;

R$^1$ is hydrogen, aryl, formyl, $C_{1-6}$alkylcarbonyl, $C_{1-6}$alkyl, $C_{1-6}$alkyloxycarbonyl, $C_{1-6}$alkyl substituted with formyl, $C_{1-6}$alkylcarbonyl, $C_{1-6}$alkyloxycarbonyl; and each R$^2$ independently is hydroxy, halo, $C_{1-6}$alkyl optionally substituted with cyano or —C(=O)R$^4$, $C_{3-7}$cycloalkyl, $C_{2-6}$alkenyl optionally substituted with one or more halogen atoms or cyano, $C_{2-6}$alkynyl optionally substituted with one or more halogen atoms or cyano, $C_{1-6}$alkyloxy, $C_{1-6}$alkyloxycarbonyl, carboxyl, cyano, nitro, amino, mono- or di($C_{1-6}$alkyl)amino, polyhalomethyl, polyhalomethyloxy, polyhalomethylthio, —S(=O)$_p$R$^4$, —NH—S(=O)$_p$R$^4$, —C(=O)R$^4$, —NHC(=O)H, —C(=O)NHNH$_2$, —NHC(=O)R$^4$, —C(=NH)R$^4$ or a radical of formula

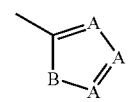

(c)

wherein each A independently is N, CH or CR$^4$;
B is NH, O, S or NR$^4$;
p is 1 or 2; and
R$^4$ is methyl, amino, mono- or dimethylamino or polyhalomethyl;

L is $C_{1-10}$alkyl, $C_{2-10}$alkenyl, $C_{2-10}$alkynyl, $C_{3-7}$cycloalkyl, whereby each of said aliphatic group may be substituted with one or two substituents independently selected from $C_{3-7}$cycloalkyl, indolyl or isoindolyl, each optionally substituted with one, two, three or four substituents each independently selected from halo, $C_{1-6}$alkyl, hydroxy, $C_{1-6}$alkyloxy, cyano, aminocarbonyl, nitro, amino, polyhalomethyl, polyhalomethyloxy and $C_{1-6}$alkylcarbonyl, phenyl, pyridinyl, pyrimidinyl, pyrazinyl or pyridazinyl, wherein each of said aromatic rings may optionally be substituted with one, two, three, four or five substituents each independently selected from the substituents defined in R$^2$; or L is —X—R$^3$ wherein R$^3$ is phenyl, pyridinyl, pyrimidinyl, pyrazinyl or pyridazinyl, wherein each of said aromatic rings may optionally be substituted with one, two, three, four or five substituents each independently selected from the substituents defined in R$^2$; and X is —NR$^1$—, —NH—NH—, —N=N—, —O—, —C(=O)—, —CHOH—, —S—, —S(=O)— or —S(=O)$_2$—;

aryl is phenyl or phenyl substituted with one, two, three, four or five substituents each independently selected from halo, $C_{1-6}$alkyl, $C_{3-7}$cycloalkyl, $C_{1-6}$alkyloxy, cyano, nitro, polyhalo$C_{1-6}$alkyl and polyhalo$C_{1-6}$alkyloxy;

with the proviso that compounds wherein

L is $C_{1-3}$alkyl; R$^1$ is selected from hydrogen, ethyl and methyl; -a$^1$=a$^2$-a$^3$=a$^4$- represents a bivalent radical of formula (a-1); n is 0 or 1 and R$^2$ is selected from fluoro, chloro, methyl, trifluoromethyl, ethyloxy and nitro; or L is —X—R$^3$, X is —NH—; R$^1$ is hydrogen; -a$^1$=a$^2$-a$^3$=a$^4$- represents a bivalent radical of formula (a-1); n is 0 or 1 and R$^2$ is selected from chloro, methyl, methyloxy, cyano, amino and nitro and R$^3$ is phenyl, optionally substituted with one substituent selected from chloro, methyl, methyloxy, cyano, amino and nitro;

and the compounds

N,N'-dipyridinyl-(1,3,5)-triazine-2,4-diamine;
(4-chloro-phenyl)-(4(1-(4-isobutyl-phenyl)-ethyl)-(1,3,5)triazin-2-yl)-amine are not included;

and (b) one or more pharmaceutically acceptable water-soluble polymers.

As used in the foregoing definitions and hereinafter halo defines fluoro, chloro, bromo and iodo; polyhalomethyl as a group or part of a group is defined as mono- or polyhalo-substituted methyl, in particular methyl with one or more fluoro atoms, for example, difluoromethyl or trifluoromethyl; polyhalo$C_{1-6}$alkyl as a group or part of a group is defined as mono- or polyhalosubstituted $C_{1-6}$alkyl, for example, the groups defined in halomethyl, 1,1-difluoroethyl and the like; in case more than one halogen atoms are attached to an alkyl group within the definition of polyhalomethyl or polyhalo$C_{1-6}$alkyl, they may be the same or different; $C_{1-4}$alkyl as a group or part of a group encompasses the straight and branched chained saturated hydrocarbon radicals having from 1 to 4 carbon atoms such as, for example, methyl, ethyl, propyl, butyl and the like; $C_{1-6}$alkyl as a group or part of a group encompasses the straight and branched chained saturated hydrocarbon radicals as defined in $C_{1-4}$alkyl as well as the higher homologues thereof containing 5 or 6 carbon atoms such as, for example pentyl or hexyl; $C_{1-10}$alkyl as a group or part of a group encompasses the straight and branched chained saturated hydrocarbon radicals as defined in $C_{1-6}$alkyl as well as the higher homologues thereof containing 7 to 10 carbon atoms such as, for example, heptyl, octyl, nonyl or decyl; $C_{1-12}$alkyl as a group or part of a group encompasses the straight and branched chained saturated hydrocarbon radicals as defined in $C_{1-10}$alkyl as well as the higher homologues thereof containing 11 or 12 carbon atoms such as, for example, undecyl, dodecyl and the like; $C_{1-4}$alkylidene as a group or part of a group defines bivalent straight and branched chained hydrocarbons having from 1 to 4 carbon atoms such as, for example, methylene, ethylidene, propylidene, butylidene and the like; $C_{1-4}$alkanediyl as a group or part of a group encompasses those radicals defined under $C_{1-4}$alkylidene as well as other bivalent straight and branched chained hydro-carbons having from 1 to 4 carbon atoms such as, for example, 1,2-ethanediyl, 1,3-propanediyl, 1,4-butanediyl and the like; $C_{3-7}$cycloalkyl as a group or part of a group is generic to cyclopropyl, cyclobutyl, cyclopentyl, cyclohexyl and cycloheptyl; $C_{3-10}$alkenyl as a group or part of a group defines straight and branch chained hydrocarbon radicals containing one double bond and having from 3 to 10 carbon atoms such as, for example, 2-propenyl, 2-butenyl, 2-pentenyl, 3-pentenyl, 3-methyl-2-butenyl, 3-hexenyl, 3-heptenyl, 2-octenyl, 2-nonenyl, 2-decenyl and the like, whereby the carbon atom attached to the pyrimidine ring is preferably an aliphatic carbon atom; $C_{3-10}$alkynyl as a group or part of a group defines straight and branch chained hydrocarbon radicals containing one triple bond and having from 3 to 10 carbon atoms such as, for example, 2-propynyl, 2-butynyl, 2-pentynyl, 3-pentynyl, 3-methyl-2-butynyl, 3-hexynyl, 3-heptynyl, 2-octynyl, 2-nonynyl, 2-decynyl and the like, whereby the carbon atom attached to the pyrimidine ring is preferably an aliphatic carbon atom; $C_{2-6}$alkenyl defines straight and branched chain hydrocarbon radicals having from 2 to 6 carbon atoms containing a double bond such as ethenyl, propenyl, butenyl, pentenyl, hexenyl and the like; $C_{2-10}$alkenyl defines straight and branched chain hydrocarbon radicals having from 2 to 10 carbon atoms containing a double bond such as the groups defined for $C_{2-6}$alkenyl and heptenyl, octenyl, nonenyl, decenyl and the like; $C_{2-6}$alkynyl defines straight and branched chain hydrocarbon radicals having from 2 to 6 carbon atoms containing a triple bond such as ethynyl, propynyl, butynyl, pentynyl, hexynyl and the like; $C_{2-10}$alkynyl defines straight and branched chain hydrocarbon radicals having from 2 to 10 carbon atoms containing a triple bond such as the groups defined for $C_{2-6}$alkynyl and heptynyl, octynyl; nonynyl, decynyl and the like; $C_{1-3}$alkyl as a group or part of a group encompasses the straight and branched chain saturated hydrocarbon radicals having from 1 to 3 carbon atoms such as, methyl, ethyl and propyl; $C_{4-10}$alkyl encompasses the straight and branched chain saturated hydrocarbon radicals as defined above, having from 4 to 10 carbon atoms. The term $C_{1-6}$alkyloxy defines straight or branched chain saturated hydrocarbon radicals such as methoxy, ethoxy, propyloxy, butyloxy, pentyloxy, hexyloxy, 1-methylethyloxy, 2-methyl-propyloxy, 2-methylbutyloxy and the like; $C_{3-6}$cycloalkyloxy is generic to cyclo-propyloxy, cyclobutyloxy, cyclopentyloxy and cyclohexyloxy.

As used herein before, the term (=O) forms a carbonyl moiety when attached to a carbon atom, a sulfoxide group when attached once to a sulfur atom, and a sulfonyl group when attached twice to a sulfur atom.

When any variable (e.g. aryl, $R^3$, $R^4$ in formula (I-A) etc.) occurs more than one time in any constituent, each definition is independent.

Lines drawn into ring systems from substituents indicate that the bond may be attached to any of the suitable ring atoms. For instance for compounds of formula (I-A), $R^4$ can be attached to any available carbon atom of the phenyl or pyridyl ring.

The addition salts as mentioned herein are meant to comprise the therapeutically active addition salt forms which the compounds of formula (I-A), (I-B) or (I-C) are able to form with appropriate acids, such as, for example, inorganic acids such as hydrohalic acids, e.g. hydrochloric or hydrobromic acid; sulfuric; nitric; phosphoric and the like acids; or organic acids such as, for example, acetic, propanoic, hydroxyacetic, lactic, pyruvic, oxalic, malonic, succinic, maleic, fumaric, malic, tartaric, citric, methane-sulfonic, ethanesulfonic, benzenesulfonic, p-toluenesulfonic, cyclamic, salicylic, p-aminosalicylic, pamoic and the like acids.

The pharmaceutically acceptable addition salts as mentioned hereinabove are also meant to comprise the therapeutically active non-toxic base, in particular, a metal or amine addition salt forms which the compounds of the present invention are able to form. Said salts can conveniently be obtained by treating the compounds of the present invention containing acidic hydrogen atoms with appropriate organic and inorganic bases such as, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like.

Conversely said salt forms can be converted by treatment with an appropriate base or acid into the free acid or base form.

The term addition salts also comprises the hydrates and the solvent addition forms which the compounds of formula (I-A), (I-B) or (I-C) are able to form. Examples of such forms are e.g. hydrates, alcoholates and the like.

The term stereochemically isomeric forms of the compounds of formula (I-A), (I-B) or (I-C), as used hereinbefore, defines all possible compounds made up of the same atoms bonded by the same sequence of bonds but having different three-dimensional structures which are not interchangeable, which the compounds of the present invention may possess. Unless otherwise mentioned or indicated, the chemical designation of a compound encompasses the mixture of all possible stereochemically isomeric forms which said compound may possess. Said mixture may contain all diastereomers and/or enantiomers of the basic molecular structure of said compound. All stereochemically isomeric forms of the compounds of formula (I-A), (I-B) or (I-C) both in pure form or in admixture with each other are intended to be embraced within the scope of the present invention.

Some of the compounds of formula (I-A), (I-B) or (I-C) may also exist in their tautomeric forms. Such forms although not explicitly indicated in the above formula are intended to be included within the scope of the present invention.

Whenever used hereinafter, the term compound of formula (I-A), (I-B) or (I-C) is meant to include any subgroup thereof, also the N-oxides, the pharmaceutically acceptable addition salts, the quaternary amines and all stereoisomeric forms.

Suitable compounds of formula (I-A) are those wherein Y is $CR^5$ or N; A is CH, $CR^4$ or N; n is 0, 1, 2, 3 or 4; Q is —$NR^1R^2$; $R^1$ and $R^2$ are each independently selected from hydrogen, hydroxy, $C_{1-12}$alkyl, $C_{1-12}$alkyloxy, $C_{1-12}$alkylcarbonyl, $C_{1-12}$alkyloxy-carbonyl, aryl, amino, mono- or di($C_{1-12}$alkyl)amino, mono- or di($C_{1-12}$alkyl)amino-carbonyl wherein each of the aforementioned $C_{1-12}$alkyl groups may optionally and each individually be substituted with one or two substituents each independently selected from hydroxy, $C_{1-6}$alkyloxy, hydroxy$C_{1-6}$alkyloxy, carboxyl, $C_{1-6}$alkyloxy-carbonyl, cyano, amino, imino, aminocarbonyl, aminocarbonylamino, mono- or di($C_{1-6}$alkyl)amino, aryl and Het; or $R^1$ and $R^2$ taken together may form pyrrolidinyl, piperidinyl, morpholinyl, azido or mono- or di($C_{1-12}$alkyl)amino$C_{1-4}$alkylidene; $R^3$ is hydrogen, aryl, $C_{1-6}$alkylcarbonyl, $C_{1-6}$alkyl, $C_{1-6}$alkyloxycarbonyl, $C_{1-6}$alkyl substituted with $C_{1-6}$alkyloxycarbonyl; each $R^4$ independently is hydroxy, halo, $C_{1-6}$alkyl, $C_{1-6}$alkyloxy, cyano, aminocarbonyl, nitro, amino, trihalomethyl, trihalo-methyloxy; $R^5$ is hydrogen or $C_{1-4}$alkyl; L is —$X^1$—$R^6$ or —$X^2$-Alk-$R^7$ wherein $R^6$ and $R^7$ each independently are phenyl or phenyl substituted with one, two, three, four or five substituents each independently selected from halo, hydroxy, $C_{1-6}$alkyl, $C_{1-6}$alkyloxy, $C_{1-6}$alkylcarbonyl, $C_{1-6}$alkyloxycarbonyl, formyl, cyano, nitro, amino, and trifluoromethyl, $X^1$ and $X^2$ are each independently —$NR^3$—, —NH—NH—, —N=N—, —O—, —S—, —S(=O)— or —S(=O)$_2$—, and Alk is $C_{1-4}$alkanediyl; aryl is phenyl or phenyl substituted with one, two, three, four or five substituents each independently selected from halo, $C_{1-6}$alkyl, $C_{1-6}$alkyloxy, cyano, nitro and trifluoromethyl; Het is an aliphatic or aromatic heterocyclic radical; said aliphatic heterocyclic radical is selected from pyrrolidinyl, piperidinyl, homopiperidinyl, piperazinyl, morpholinyl, tetrahydrofuranyl and tetrahydrothienyl wherein each of said aliphatic heterocyclic radical may optionally be substituted with an oxo group; and said aromatic heterocyclic radical is selected from pyrrolyl, furanyl, thienyl, pyridyl, pyrimidinyl, pyrazinyl and pyridazinyl wherein each of said aromatic heterocyclic radical may optionally be substituted with hydroxy.

Most preferred compounds of formula (I-A) are
[4[-amino-6-[(2,6-dichlorophenyl)methyl]-2-pyrimidinyl]amino]benzonitrile (*1.B1; comp. 1);
6-[(2,6-dichlorophenyl)methyl]-N2-(4-fluorophenyl)-2,4-pyrimidinediamine (*1.B1; comp. 2);
4-[[4-[(2,4-dichlorophenyl)methyl]-6-[(4-hydroxybutyl)amino]-2-pyrimidinyl]amino]-benzonitrile (*1.B2; comp. 3);
4-[[4-[(2,6-dichlorophenyl)methyl]-6-[(3-hydroxypropyl)amino]-2-pyrimidinyl-amino]benzonitrile (*1.B1; comp. 4);
N-[2-[(4-cyanophenyl)amino]-6-[(2,6-dichlorophenyl)methyl]-4-pyrimidinyl]acetamide (*1.B7; comp. 5);
N-[2-[(4-cyanophenyl)amino]-6-[(2,6-dichlorophenyl)methyl]-4-pyrimidinyl]-butanamide (*1.B7; comp. 6);
4-[[2-amino-6-(2,6-dichlorophenoxy)-4-pyrimidinyl]amino]benzonitrile (*1.B1; comp. 7);
4-[[4-[(2,6-dichlorophenyl)methyl]-6-[(2-hydroxy-2-phenylethyl)amino]-2-pyrimidinyl]amino]benzonitrile (*1.B2; comp. 8);
4-[[4-[(2,6-dichlorophenyl)methyl]-6-[[3-(2-oxo-1-pyrrolidinyl)propyl]amino]-2-pyrimidinyl]amino]benzonitrile (*1.B2; comp. 9);
4-[[4-[(2,6-dichlorophenyl)methyl]-6-[[2-(2-hydroxyethoxy)ethyl]amino]-2-pyrimidinyl]amino]benzontrile monohydrochloride (*1.B2; comp. 10);
4-[[4-[(2,6-dichlorophenyl)methyl]-6-[(2,3-dihydroxypropyl)amino]-2-pyrimidinyl]-amino]benzonitrile (*1.B2; comp. 11);
4-[[4-[(2,6-dichlorophenyl)methyl]-6-(hydroxyamino)-2-pyrimidinyl]amino]-benzonitrile (*1.B4; comp. 12);
4-[[4-[(2-cyanoethyl)amino]-6-[(2,6-dichlorophenyl)methyl]-2-pyrimidinyl]amino]-benzonitrile (*1.B3; comp. 13);
4-[[4-[(2,6-dichlorophenyl)methyl]-6-[[2-(1-pyrrolidinyl)ethyl]amino]-2-pyrimidinyl]-amino]benzonitrile (*1.B3; comp. 14);
4-[[4-amino-6-[(2,6-dichlorophenyl)methyl]-5-methyl-2-pyrimidinyl]amino]-benzonitrile (*1.B1; comp. 15);
N2-(4-bromophenyl)-6-[(2,6-dichlorophenyl)methyl]-5-methyl-2,4-pyrimidinediamine (*1.B1; comp. 16);
4-[[4-[(2,4,6-trimethylphenyl)amino]-2-pyrimidinyl]amino]benzonitrile (*1.B8a; comp. 17);
4-[[2-[(2,4,6-trimethylphenyl)amino]-4-pyrimidinyl]amino]benzonitrile (*1.B9a; comp. 18);
4-[[4-[(2,6-dimethylphenyl)amino]-2-pyrimidinyl]amino]benzonitrile (*1.B9a; comp. 19);
4-[[4-(2,4,6-trimethylphenoxy)-2-pyrimidinyl]amino]benzonitrile (*1.B10; comp. 20);
4-[[4-[(2,6-dichlorophenyl)thio]-2-pyrimidinyl]amino]benzonitrile (*1.B10; comp. 21);
4-[[4-[[2,6-dibromo-4-(1-methylethyl)phenyl]amino]-2-pyrimidinyl]amino]benzonitrile (*1.B9a; comp. 22);
4-[[4-[[2,6-dichloro-4-(trifluoromethyl)phenyl]amino]-2-pyrimidinyl]amino]-benzonitrile (*1.B9c; comp. 23);
4-[[4-[(2,4-dichloro-6-methylphenyl)amino]-2-pyrimidinyl]amino]benzonitrile (*1.B9a; comp. 24);
4-[[2-[(cyanophenyl)amino]-4-pyrimidinyl]amino]-3,5-dimethylbenzonitrile (*1.B 8a or 1.B8b; comp. 25);
4-[[4-[(2,4-dibromo-6-fluorophenyl)amino]-2-pyrimidinyl]amino]benzonitrile (*1.B9c; comp. 26);
4-[[4-amino-6-[(2,6-dichlorophenyl)methyl]-5-methyl-2-pyrimidinyl]amino]-benzeneacetonitrile (*1.B1; comp. 27);
4-[[4-[methyl(2,4,6-trimethylphenyl)amino]-2-pyrimidinyl]amino]benzonitrile (*1.B9c; comp. 28);

4-[[4-[(2,4,6-trichlorophenyl)amino]-2-pyrimidinyl]amino]benzonitrile (*1.B9c; comp. 29);
4-[[4-[(2,4,6-trimethylphenyl)thio]-2-pyrimidinyl]amino]benzonitrile (*1.B10; comp. 30);
4-[[4-[(2,4,6-trimethylphenyl)amino-2-pyrimidinyl]amino]benzonitrile (*1.B11; comp. 31);
4-[[4-amino-6-[(2,4,6-trimethylphenyl)amino]-2-pyrimidinyl]amino]benzonitrile (*1.B1; comp. 32);
4-[[2-amino-6-[(2,4,6-trimethylphenyl)amino]-4-pyrimidinyl]amino]benzonitrile (*1.B1; comp. 33);
4-[[4-(2-bromo-4-chloro-6-methylphenoxy)-2-pyrimidinyl]amino]benzonitrile (*1.B10; comp. 34);
4-[[4-[(4-chloro-2,6-dimethylphenyl)amino]-2-pyrimidinyl]amino]benzonitrile (*1.B9c; comp. 35);
3,5-dichloro-4-[[2-[(4-cyanophenyl)amino]-4-pyrimidinyl]amino]benzonitrile (*1.B9a; comp. 36);
4-[[4-[[2,6-dichloro-4-(trifluoromethoxy)phenyl]amino]-2-pyrimidinyl]amino]-benzonitrile (*1.B9c; comp. 37);
4-[[4-[(2,4-dibromo-3,6-dichlorophenyl)amino]-2-pyrimidinyl]amino]benzonitrile (*1.B9c; comp. 38);
4-[[4-[(2,6-dibromo-4-propylphenyl)amino]-2-pyrimidinyl]amino]benzonitrile (*1.B9c; comp. 39);
4-[[4-[(2,4,6-trimethylphenyl)amino]-2-pyrimidinyl]amino]benzamide (*1.B11; comp. 40);
4-[[4-[(4-(1,1-dimethylethyl)-2,6-dimethylphenyl)amino]-2-pyrimidinyl]amino]-benzonitrile (*1.B9a; comp. 41);
4-[[2-[(4-cyanophenyl)amino]4-pyrimidinyl]oxy]-3,5-dimethylbenzonitrile (*1.B10; comp. 42);
4-[[4-[(4-chloro-2,6-dimethylphenyl)amino]-5-methyl-2-pyrimidinyl]amino]-benzonitrile (*1.B9c; comp. 43);
4-[[2-[(4-cyanophenyl)amino]-5-methyl-4-pyrimidinyl]amino-3,5-dimethylbenzonitrile (*1.B9b; comp. 44);
4-[[4-[[4-(1,1-dimethylethyl)-2,6-dimethylphenyl]amino]-5-methyl-2-pyrimidinyl]-amino]benzonitrile (*1.B9c; comp. 45);
4-[[4-[(4-bromo-2,6-dimethylphenyl)amino]-5-methyl-2-pyrimidinyl]amino]-benzonitrile (*1.B9c; comp. 46);
4-[[5-methyl-4-[(2,4,6-trimethylphenyl)thio]-2-pyrimidinyl]amino]benzonitrile (*1.B9c; comp. 47);
4-[[4-[(2,6-dibromo-4-propylphenyl)amino]-5-methyl-2-pyrimidinyl]amino]-benzonitrile (*1.B9a; comp. 48);
4-[[4-[(2,4,6-trimethylphenyl)amino]-2-pyrimidinyl]amino]benzamide, N3-oxide (*1.B12; comp. 49);
N2-(4-chlorophenyl)-N4-(2,4,6-trimethylphenyl)-2,4-pyrimidinediamine (*1.B8a; comp. 50);
4-[[4-[[2,6-dibromo-4-(1-methylethyl)phenyl]amino]-5-methyl-2-pyrimidinyl]amino]-benzonitrile (*1.B9a; comp. 51);
4-[[2-[(4-cyanophenyl)amino]-5-methyl-4-pyrimidinyl]amino]-3,5-dimethyl Benzonitrile (*1.B9b; comp. 52);
4-[[4-[(phenylmethyl)amino]-2-pyrimidinyl]amino]benzonitrile (comp. 53);
4-[[4-amino-6-(2,6-dimethylphenoxy)-1,3,5-triazin-2-yl]amino]benzonitrile (*1.B15; comp. 54);
4-[[4-amino-6-[(2-chloro-6-methylphenyl)amino]-1,3,5-triazin-2-yl]amino]benzonitrile (*1.B13a; comp. 55);
4-[[4-amino-6-[(2,4,6-trimethylphenyl)amino]-1,3,5-triazin-2-yl]amino]benzonitrile (*1.B13a or 1.B13b; comp. 56);
4-[[4-(hydroxyamino)-6-[(2,4,6-trimethylphenyl)amino]-1,3,5-triazin-2-yl]amino]-benzonitrile (*1.B14; comp. 57);
4-[[4-amino-6-[(2-ethyl-6-methylphenyl)amino]-1,3,5-triazin-2-yl]amino]benzonitrile (*1.B13b; comp. 58);
4-[[4-amino-6-[(2,6-dichlorophenyl)thio]-1,3,5-triazin-2-yl]amino]benzonitrile (*1.B13b; comp. 59);
4-[[4-(hydroxyamino)-6-[(2,4,6-trichlorophenyl)amino]-1,3,5-triazin-2-yl]amino]-benzonitrile (*1.B14; comp. 60);
4-[[4-amino-6-(2,4,6-trimethylphenoxy)-1,3,5-triazin-2-yl]amino]benzonitrile (*1.B13b; comp. 61);
4-[[4-(hydroxyamino)-6-(2,4,6-trimethylphenoxy)-1,3,5-triazin-2-yl]amino]-benzonitrile (*1.B14; comp. 62);
4-[[4-amino-6-[(2,4-dichloro-6-methylphenyl)amino]-1,3,5-triazin-2-yl]amino]-benzonitrile (*1.B13b; comp. 63);
4-[[4-[(2,4-dichloro-6-methylphenyl)amino]-6-(hydroxyamino)-1,3,5-triazin-2-yl]-amino]benzontrile (*1.B14; comp. 64);
4-[[4-(hydroxyamino)-6-(2,4,6-trichlorophenoxy)-1,3,5-triazin-2-yl]amino]benzonitrile trifluoroacetate (1:1) (*1.B14; comp. 65);
4-[[4-(4-acetyl-2,6-dimethylphenoxy)-6-amino-1,3,5-triazin-2-yl]amino]benzonitrile (*1.B16; comp. 66);
4-[[4-amino-6-(2,4,6-tribromophenoxy)-1,3,5-triazin-2-yl]amino]benzonitrile (*1.B17; comp. 67);
4-[[4-amino-6-(4-nitro-2,6-dimethylphenoxy)-1,3,5-triazin-2-yl]amino]benzonitrile (*1.B17; comp. 68);
4-[[4-amino-6-(2,6-dibromo-4-methylphenoxy)-1,3,5-triazin-2-yl]amino]benzonitrile (*.B17; comp. 69);
4-[[4-amino-6-(4-formyl-2,6-dimethylphenoxy)-1,3,5-triazin-2-yl]amino]benzonitrile (*1.B17; comp. 70);
4-[[4-amino-6-[(2,4-dichlorophenyl)thio]-1,3,5-triazin-2-yl]amino]benzonitrile (*1.B17; comp. 71);
4-[[4-[(5-acetyl-2,3-dihydro-7-methyl-1H-inden-4-yl)oxy]-6-amino-1,3,5-triazin-2-yl]-amino]benzonitrile (*1.B20; comp. 72);
4-[[4-amino-6-[(4-bromo-2-chloro-6-methylphenyl)amino]-1,3,5-triazin-2-yl]amino]-benzonitrile (*1.B20; comp. 73);
4-[[4-amino-6-[(2-chloro4,6-dimethylphenyl)amino]-1,3,5-triazin-2-yl]amino]-benzonitrile (*1.B20; comp. 74);
4-[[4-amino-6-[[2,4-dichloro-6-(trifluoromethyl)phenyl]amino]-1,3,5-triazin-2-yl]-amino]benzonitrile (*1.B13; comp. 75);
4-[[4-amino-6-[methyl(2,4,6-trimethylphenyl)amino]-1,3,5-triazin-2-yl]amino]-benzonitrile (*1.B18; comp. 76);
4-[[4-amino-6-[(2,6-dibromo-4-methylphenyl)amino]-1,3,5-triazin-2-yl]amino]-benzonitrile (*1.B13b; comp. 77);
4-[[4-amino-6-[[2,6-dibromo-4-(1-methylethyl)phenyl]amino]-1,3,5-triazin-2-yl]-amino]benzonitrile (*1.B13b; comp. 78);

the N-oxides, the pharmaceutically acceptable addition salts and the stereochemically isomeric forms thereof (* indicates the example number of the preparation procedure listed in the experimental part according to which the compound of formula (I-A) was synthesized).

Suitable compounds of formula (I-B) are those wherein one or more of the following restrictions apply:
i) -$b^1$=$b^2$-C($R^{2a}$)=$b^3$-$b^4$=is a radical of formula (b-1);
ii) q is 0;
iii) $R^{2a}$ is cyano or —C(=O)NH$_2$, preferably $R^{2a}$ is cyano;
iv) Y is cyano, —C(=O)NH$_2$ or a halogen, preferably a halogen;
v) Q is hydrogen or —NR$^4$R$^5$ wherein R$^4$ and R$^5$ are preferably hydrogen;
vi) L is —X—R$^3$ wherein X is preferably NR$^1$, O or S, most preferably X is NH, and R$^3$ is substituted phenyl with C$_{1-6}$alkyl, halogen and cyano as preferred substituents.

Another interesting group of compounds of formula (I-B) are those compounds of formula (I-B) wherein L is —X—R$^3$ wherein R$^3$ is 2,4,6-trisubstituted phenyl, each substituent independently selected from chloro, bromo, fluoro, cyano or C$_{1-4}$alkyl.

Also interesting are those compounds of formula (I-B) wherein Y is chloro or bromo and Q is hydrogen or amino.

Particular compounds of formula (I-B) are those compounds of formula (I-B) wherein the moiety in the 2 position of the pyrimidine ring is a 4-cyano-anilino group.

Preferred compounds of formula (I-B) are those compounds of formula (I-B) wherein the moiety in the 2 position of the pyrimidine ring is a 4-cyano-anilino group, L is —X—R³ wherein R³ is a 2,4,6-trisubstituted phenyl, Y is a halogen and Q is hydrogen or NH₂.

Most preferred compounds of formula (I-B) are:

4-[[4-amino-5-chloro-6-[(2,4,6-trimethylphenyl)amino]-2-pyrimidinyl]amino]-benzonitrile;

4-[[5-chloro-4-[(2,4,6-trimethylphenyl)amino]-2-pyrimidinyl]amino]benzonitrile;

4-[[5-bromo-4-(4-cyano-2,6-dimethylphenoxy)-2-pyrimidinyl]amino]benzonitrile;

4-[[4-amino-5-chloro-6-[(4-cyano-2,6-dimethylphenyl)amino]-2-pyrimidinyl]amino]-benzonitrile;

4-[[5-bromo-6-[(4-cyano-2,6-dimethylphenyl)amino]-2-pyrimidinyl]amino]-benzonitrile;

4-[[4-amino-5-chloro-6-(4-cyano-2,6-dimethylphenyloxy)-2-pyrimidinyl]amino]-benzonitrile; and 4-[[4-amino-5-bromo-6-(4-cyano-2,6-dimethylphenyloxy)-2-pyrimidinyl]amino]-benzonitrile; the N-oxides, the pharmaceutically acceptable addition salts, quaternary amines and the stereochemically isomeric forms thereof.

An interesting group of compounds of formula (I-C) are those compounds of formula (I-C) wherein one or more of the following conditions are met:

(i) n is 1;

(ii) -a¹=a²-a³=a⁴- represents a bivalent radical of formula (a-1);

(iii) R¹ is hydrogen or alkyl;

(iv) R² is cyano; aminocarbonyl; mono- or di(methyl)aminocarbonyl; $C_{1-6}$alkyl substituted with cyano, aminocarbonyl or mono- or di(methyl)aminocarbonyl; and more in particular, R² is on the 4 position relative to the —NR¹— moiety;

i) L is —X—R³ wherein X is preferably —NR¹—, —O— or —S—, most preferably X is —NH—, and R³ is substituted phenyl with $C_{1-6}$alkyl, halogen and cyano as preferred substituents.

Preferred compounds of formula (I-C) are those compounds of formula (I-C) wherein L is —X—R³ wherein R³ is a disubstituted phenyl group or a trisubstituted phenyl group, each substituent independently selected from chloro, bromo, fluoro, cyano or $C_{1-4}$alkyl.

Most preferred compound of formula is 4-[[4-[(2,4,6-trimethylphenyl)amino]-1,3,5-triazin-2-yl]amino]benzonitrile.

The compounds of formula (I-A) can be prepared according to art-known procedures.

In particular, the compounds of formula (I-A) can generally be prepared by reacting an intermediate of formula (II), wherein W¹ is a suitable leaving group such as, for example, a halo atom with an amino derivative of formula (III) in a reaction inert solvent such as, for example, 1,4-dioxane, tetrahydrofuran, 2-propanol, N-methyl-pyrrolidinone and the like, optionally in the presence of a suitable base such as, for example, sodiumhydroxide, sodiumhydride, triethylamine or N,N-di-isopropyl-ethylamine or the like.

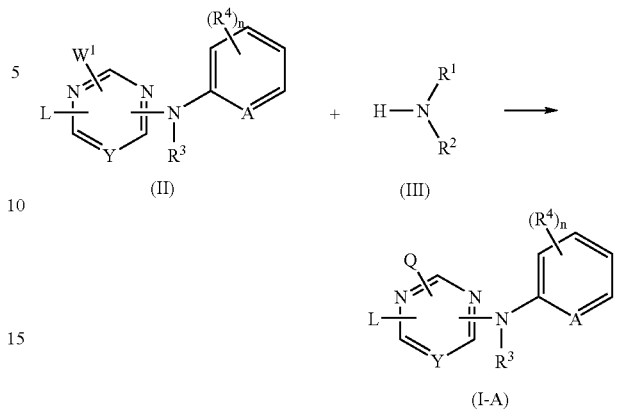

In case Q is NR¹R² and R² contains a hydroxy moiety, it may be convenient to perform the above reaction with a protected form of intermediate (III) whereby the hydroxy moiety bears a suitable protecting group P being, for instance, a benzyl, and subsequently removing the protective group according to art-known methodologies, such as, for example, reacting with BBr₃ in dichloromethane under nitrogen atmosphere.

Compounds of formula (I-A) wherein Y is CR⁵, said compounds being represented by formula (I-A-a), may also be prepared by reacting an intermediate of formula (IV) wherein W¹ is a suitable leaving group such as, for example, a halo atom, with an amino derivative of formula (V), optionally in a solvent such as, for example, water, 2-propanol, diethylether, 1-methyl-2-pyrrolidinone and the like, and optionally in the presence of an acid such as, for example, 1 N hydrochloric acid in diethylether. It may be convenient to perform the reaction under a reaction-inert atmosphere such as, for example, oxygen free argon or nitrogen.

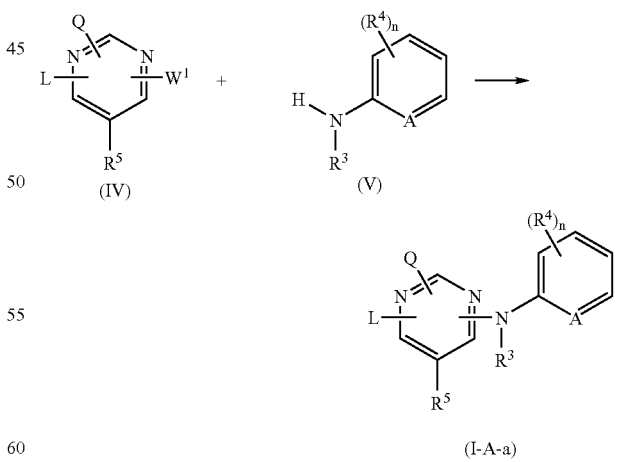

Compounds of formula (I-A-a) wherein L is —X¹—R⁶, said compounds being represented by formula (I-A-a-1), can also be prepared by reacting an intermediate of formula (VI) with an intermediate of formula (VII) in a suitable solvent such as, for example, 1,4-dioxane.

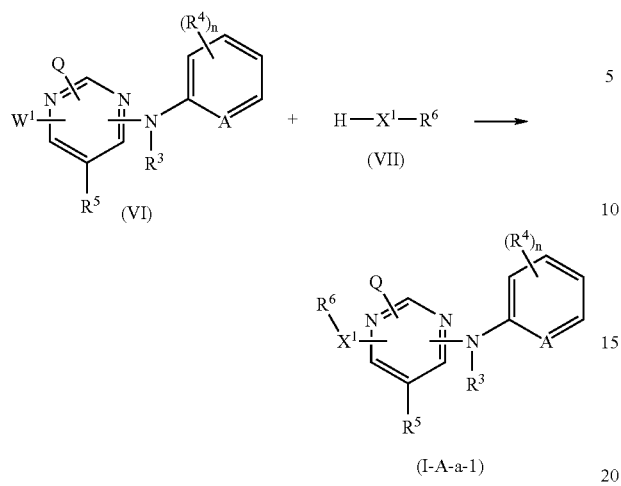

Depending on the nature of $X^1$ a suitable base or acid may be used to improve the reaction rate. For instance, in case $X^1$ is —O—, sodium hydride may be used as suitable base; or in case $X^1$ is —$NR^3$—, HCl may be used as a suitable acid.

The compounds of formula (I-A), wherein Y is N, said compounds being represented by formula (I-A-b), can also conveniently be prepared using solid phase synthesis techniques. In general, solid phase synthesis involves reacting an intermediate in a synthesis with a polymer support. This polymer supported intermediate can then be carried on through a number of synthetic steps. After each step, impurities are removed by filtering the resin and washing it numerous times with various solvents. At each step the resin can be split up to react with various intermediates in the next step thus allowing for the synthesis of a large number of compounds. After the last step in the procedure the resin is treated with a reagent or process to cleave the resin from the sample.

Suitable polymer supports include for instance Rink Amide resin (Calbiochem-Novabiochem Corp., San Diego, Calif.).

For instance, the compounds of formula (I-A-b) wherein n is 1 and the $R^4$ substituent is placed in the meta position of A, and $NR^1R^2$ is $NH_2$, said compounds being represented by formula (I-A-b-1), were prepared according to the procedure depicted in Scheme 1.

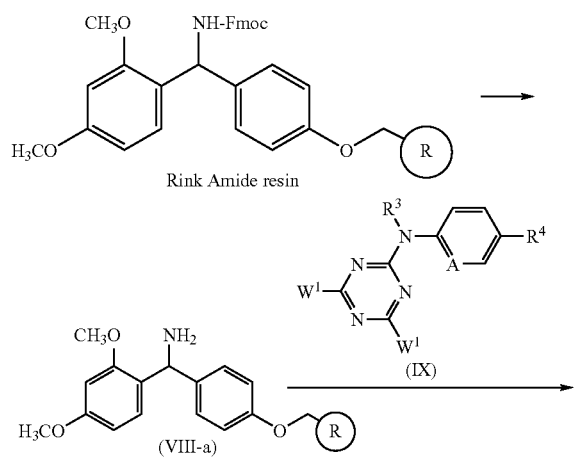

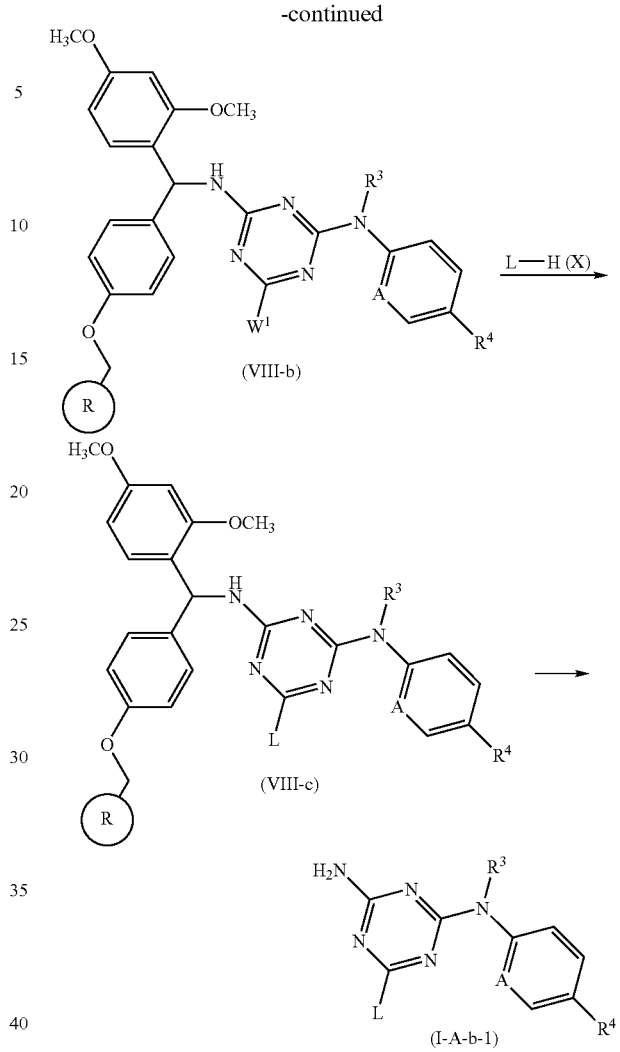

In scheme 1, Rink Amide resin is reacted in a suitable solvent such as, for example N,N-dimethylformamide in the presence of piperidine to obtain the primary amine of formula (VIII-a) which can then further be reacted with an intermediate of formula (IX) wherein $W^1$ is a suitable leaving group such as, for example, a halo atom, in the presence of a base such as for example, N,N-diisopropylethylamine, in a suitable solvent such as, for example, dimethylsulfoxide. Impurities can be removed by washing numerous times with various solvents such as, for example, N,N-dimethylformamide, dichloromethane, dimethylsulfoxide and the like. The resulting polymer-bound intermediate of formula (VIII-b) was then further reacted with L—H (X). To facilitate this transformation, silver triflate, sodium hexamethyldisilazide or cesium carbonate may be used. The resin is finally treated with a cleavage reagent such as for example trifluoroacetic acid in tetrahydrofuran, thus obtaining compounds of formula (I-A-b-1).

In this and the following preparations, the reaction products may be isolated from the reaction medium and, if necessary, further purified according to methodologies generally known in the art such as, for example, extraction, crystallization, distillation, trituration and chromatography.

The compounds of formula (I-A) may further be prepared by converting compounds of formula (I-A) into each other according to art-known group transformation reactions.

The compounds of formula (I-A) may be converted to the corresponding N-oxide forms following art-known procedures for converting a trivalent nitrogen into its N-oxide form. Said N-oxidation reaction may generally be carried out by reacting the starting material of formula (I-A) with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chlorobenzenecarboperoxoic acid, peroxoalkanoic acids, e.g. peroxoacetic acid, alkylhydroperoxides, e.g. t.butyl hydro-peroxide. Suitable solvents are, for example, water, lower alcohols, e.g. ethanol and the like, hydrocarbons, e.g. toluene, ketones, e.g. 2-butanone, halogenated hydrocarbons, e.g. dichloromethane, and mixtures of such solvents.

For instance, compounds of formula (I-A-a) wherein Q is $NR^1R^2$ and $R^1$ and $R^2$ are taken together to form mono- or di($C_{1-2}$alkyl)amino$C_{1-4}$alkylidene, said compounds being represented by formula (I-A-a-2), may be prepared by reacting a compound of formula (I-A-a) wherein $R^1$ and $R^2$ are hydrogen, said compound being represented by formula (I-A-a-3), with an intermediate of formula (XI) or a functional derivative thereof.

the like methods. Enantiomers can be obtained from racemic mixtures by first converting said racemic mixtures with suitable resolving agents such as, for example, chiral acids, to mixtures of diastereomeric salts or compounds; then physically separating said mixtures of diastereomeric salts or compounds by, for example, selective crystallization or chromatographic techniques, e.g. liquid chromatography and the like methods; and finally converting said separated diastereomeric salts or compounds into the corresponding enantiomers. Pure stereochemically isomeric forms may also be obtained from the pure stereochemically isomeric forms of the appropriate intermediates and starting materials, provided that the intervening reactions occur stereospecifically.

An alternative manner of separating the enantiomeric forms of the compounds of formula (I-A) and intermediates involves liquid chromatography, in particular liquid chromatography using a chiral stationary phase.

Some of the intermediates and starting materials are known compounds and may be commercially available or may be prepared according to art-known procedures.

Intermediates of formula (II), wherein Y is $CR^5$, said intermediates being represented by formula (II-a), can be prepared by reacting an intermediate of formula (XII) with an intermediate of formula (V) analogously to the preparation of compounds of formula (I-a).

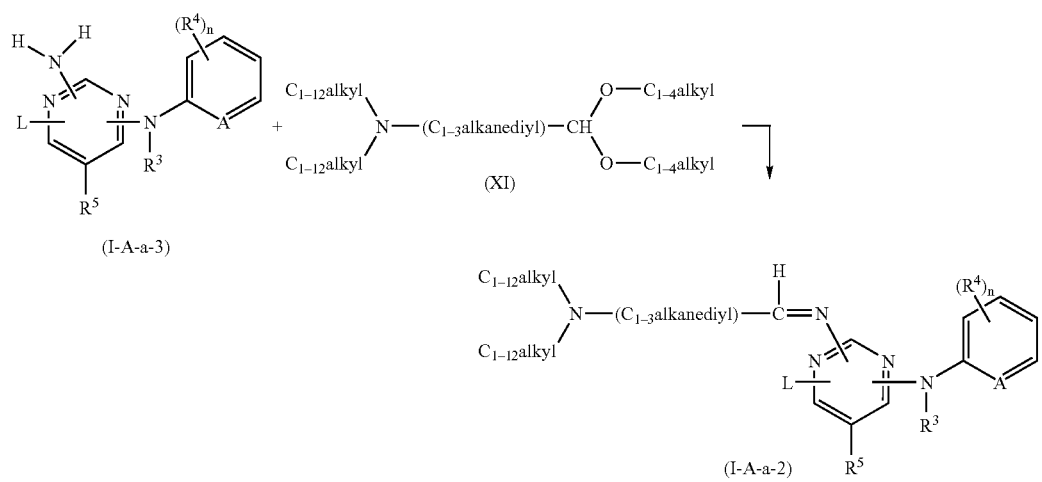

Also, compounds of formula (I-A-a) wherein Q is $NR^1R^2$ and $R^1$ and $R^2$ are hydrogen may further be reacted with an acyl halide or an alkyl chloroformate in a reaction-inert solvent such as, for example dichloromethane, in the presence of a suitable base, such as, for example, pyridine, to form the corresponding amide, respectively, carbamate derivative.

Some of the compounds of formula (I-A) and some of the intermediates in the present invention may contain an asymmetric carbon atom. Pure stereochemically isomeric forms of said compounds and said intermediates can be obtained by the application of art-known procedures. For example, diastereoisomers can be separated by physical methods such as selective crystallization or chromatographic techniques, e.g. counter current distribution, liquid chromatography and

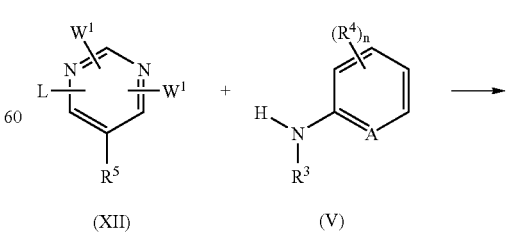

-continued

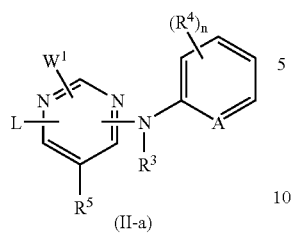
(II-a)

A particular subgroup of the intermediates of formula (II-a) is represented by formula

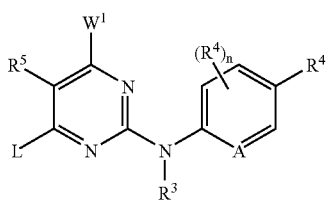
(II'-a)

wherein n' is 0,1,2, or 3.

Particular intermediates of formula (II'-a) are those wherein $W^1$ is a halo atom, more in particular, a chloro atom.

Intermediates of formula (II), wherein Y is N, $R^4$ is placed in paraposition of $NR^3$, and n is 1, said intermediates being represented by formula (II-b-1) can be prepared by reacting an intermediate of formula (XIII) wherein $W^1$ is a suitable leaving group such as, for example, a halogen, with an amine derivative of formula (XIV) in a reaction-inert solvent such as, for example, tetrahydrofuran, 1,4-dioxane or the like, in the presence of a suitable base such as, for example, triethylamine; and subsequently reacting the thus obtained intermediate of formula (XV) with an intermediate of formula (XVI) in a reaction-inert solvent such as, for example, acetonitrile, 1,4-dioxane or the like, in the presence of a base such as, for example, potassium carbonate, sodium hydride, N,N-diisopropyl-ethylamine or the like.

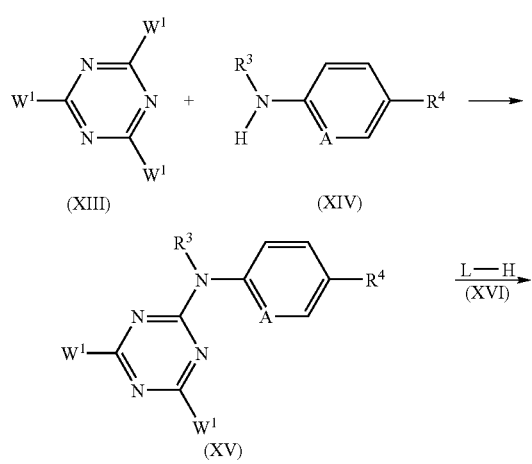

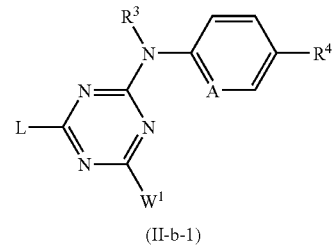
(II-b-1)

The order of the above reaction scheme may also be reversed, i.e. first an intermediate of formula (XIII) may be reacted with an intermediate of formula (XVI), and then, the resulting intermediate of formula (XVII) may further be reacted with an amine derivative of formula (XIV); thus forming an intermediate of formula (II-b-1).

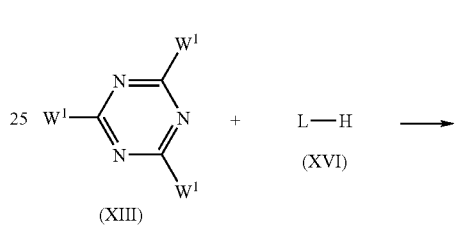

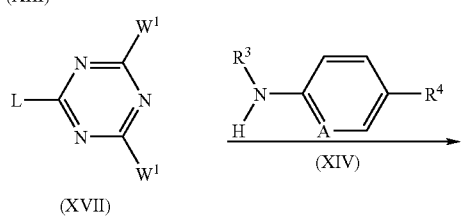

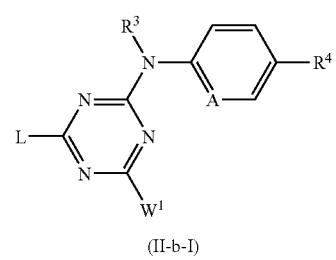
(II-b-I)

Particular intermediates are those intermediates of formula (II-b-1) wherein $R^4$ is cyano, amino, carbonyl, nitro or trifluoromethyl, $R^3$ is hydrogen, A is CH, $W^1$ is a halogen such as, chloro and bromo, and L is as defined in the compounds of formula (I) provided that $R^6$ is other than p-cyano-phenyl, p-nitro-phenyl, p-methoxy-phenyl and p-aminocarbonyl-phenyl, and $R^7$ is other than 2-(4-hydroxyphenyl)ethyl]amino; more in particular, $R^3$, A and $W^1$ are as defined above, $R^4$ is cyano and L is —$X^1$—$R^6$ or $X^2$-Alk-$R^7$; wherein $R^6$ and $R^7$ each independently are indanyl, indolyl or phenyl; each of said indanyl, indolyl or phenyl may be substituted with two, three, four or five substituents each independently selected from halo, $C_{1-6}$alkyl, $C_{1-6}$alkyloxy, hydroxy, $C_{1-6}$alkylcarbonyl, $C_{1-6}$alkyloxycarbonyl, formyl, cyano, nitro, amino and trifluoromethyl.

Intermediates of formula (IV) wherein Q is $NR^1R^2$, said intermediates being represented by formula (IV-a), can be prepared by reacting a pyrimidine derivative of formula (XVIII) wherein $W^1$ is a suitable leaving group such as, for example, a halo atom, with an intermediate of formula (III) in a reaction inert solvent such as, for example, 1,4-dioxane, 2-propanol or the like. Different regio-specific isomers may be formed and can be separated from one another using suitable separation techniques such as, for example, chromatography.

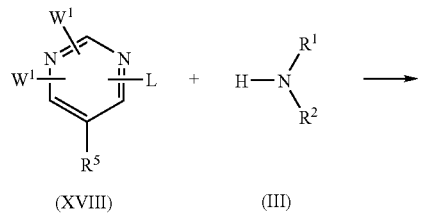

Intermediates of formula (XVIII) whereby L is L'—CH$_2$ and is attached in the 2 position of the pyrimidine ring and W$^1$ is chloro, said intermediates being represented by formula (XVIII-a), can be prepared by reacting an imidamide of formula (XIX) with a propanedioic acid ester of formula (XX) in a solvent such as, for example, ethanol, and in the presence of, for instance, sodium, and subsequently reacting the thus formed intermediate of formula (XXI) with a suitable reagent such as, for example, phosphoryl chloride.

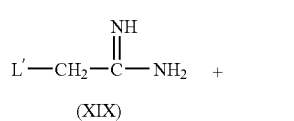

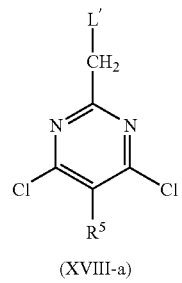

Intermediates of formula (XVIII) whereby L is L'—CH$_2$ and is attached in the 4 or 6 position of the pyrimidine ring and W$^1$ is chloro, said intermediates being represented by formula (XVIII-b), can be prepared by reacting an intermediate of formula (XXII) with urea or a functional derivative thereof, in a solvent such as, for example, ethanol, and in the presence of, for instance, sodium, and subsequently reacting the thus formed intermediate of formula (XXIII) with a suitable reagent such as, for example, phosphoryl chloride.

Intermediates of formula (XVIII) wherein L is L'—CH$_2$ and is attached anywhere on the pyrimidine ring, said intermediates being represented by formula (XVIII-c), can be prepared by reacting an intermediate of formula (XXIV), wherein W$^1$ is a suitable leaving group such as, for example, a halo atom, with an intermediate of formula (XXV) wherein W$^2$ is a suitable leaving group such as, for example, a halogen, according to the procedure of a Grignard reaction.

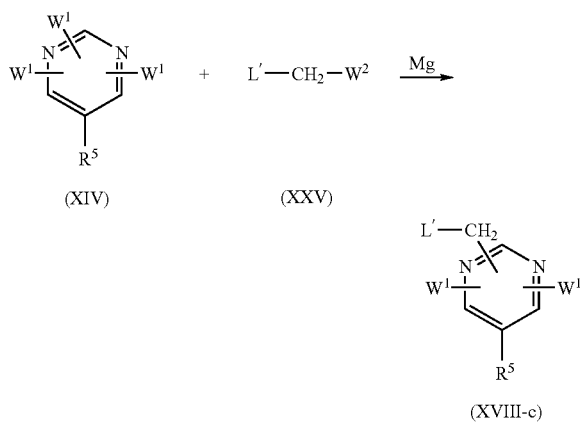

(XIV)  (XXV)

(XVIII-c)

Intermediates of formula (XVIII) wherein L is —Z—$R^6$, —Z— representing therein —O— or —NH—, and —Z—$R^6$ is attached in the 4 or 6 position of the pyrimidine ring, said intermediates being represented by formula (XVIII), can be prepared by reacting an intermediate of formula (XXVI) with an intermediate of formula (XXVII) wherein $W^1$ is a suitable leaving group such as, for example, a halo atom, in a reaction-inert solvent such as, for example, tetrahydrofuran or 1,4-dioxane, and in the presence of a suitable base such as, for example, potassium hydroxide or diisopropyl ethaneamine, or sodium hydride.

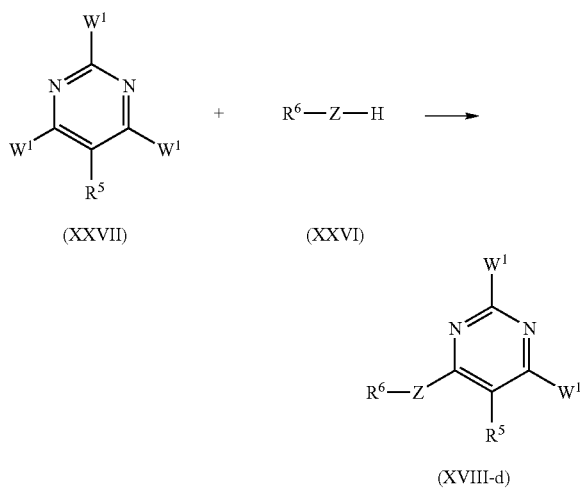

(XXVII)  (XXVI)

(XVIII-d)

Compounds of formula (I-A) and some of the intermediates may have one or more stereogenic centers in their structure, present in a R or a S configuration.

In general, compounds of formula (I-B) can be prepared by reacting an intermediate of formula (II(b)) wherein $W^1$ is a suitable leaving group such as, for example, a halogen, hydroxy, triflate, tosylate, thiomethyl, methylsulfonyl, trifluoromethylsulfonyl and the like, with an amino derivative of formula (III(b)) optionally under solvent-free conditions or in a reaction-inert solvent such as, for example, ethanol, 1-methyl-2-pyrrolidinone, N,N-dimethylformamide, 1,4-dioxane, tetrahydrofuran, dimethyl sulfoxide, tetraline, sulfolane, acetonitrile and the like, under a reaction-inert atmosphere such as, for example, oxygen free argon or nitrogen, and optionally in the presence of an acid such as, for example, 1 N hydrochloric acid in diethyl ether or the like. This reaction can be performed at a temperature ranging between 50° C. and 250° C.

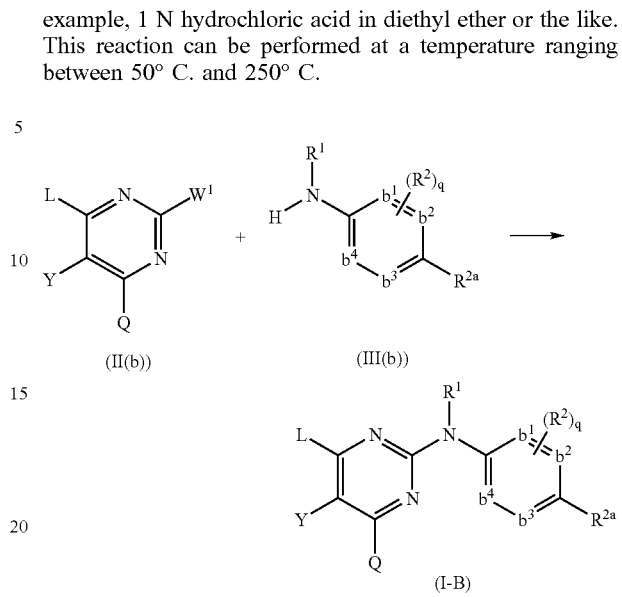

(II(b))  (III(b))

(I-B)

In this and the following preparations, the reaction products may be isolated from the reaction medium and, if necessary, further purified according to methodologies generally known in the art such as, for example, extraction, crystallization, distillation, trituration and chromatography.

The compounds of formula (I-B) wherein L is a radical of formula —$NR^1$—$R^3$, said compounds being represented by formula (I-B-1), can be prepared by reacting an intermediate of formula (IV(b)) wherein $W^2$ is a suitable leaving group such as, for example, a halogen or a triflate, with an intermediate of formula (V(b)) under solvent-free conditions or in an appropriate solvent such as, for example, ethanol, 1-methyl-2-pyrrolidinone, N,N-dimethylformamide, 1,4-dioxane, tetrahydrofuran, dimethyl sulfoxide, tetraline, sulfolane, acetonitrile and the like, under a reaction-inert atmosphere such as, for example, oxygen free argon or nitrogen, and optionally in the presence of an acid such as, for example, 1 N hydrochloric acid in diethyl ether. This reaction can be performed at a temperature ranging between 50° C. and 250° C.

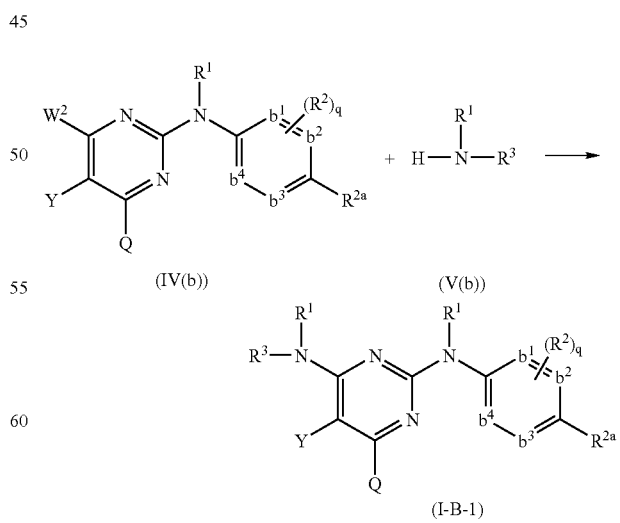

(IV(b))  (V(b))

(I-B-1)

The compounds of formula (I-B) wherein L is a radical of formula —O—$R^3$, said compounds being represented by formula (I-B-2), can be prepared by reacting an intermediate of formula (IV(b)) wherein $W^2$ is a suitable leaving group such as, for example a halogen or a triflate, with an intermediate of formula (VI(b)) in an appropriate solvent such as, for example, 1,4-dioxane, dimethyl sulfoxide, tetraline, sulfolane and the like under a reaction-inert atmosphere such as, for example, oxygen free argon or nitrogen, and in the presence of a base such as, for example, sodium hydride, potassium hydride, sodium hydroxide or the like. This reaction can be performed at a temperature ranging between 50° C. and 250° C.

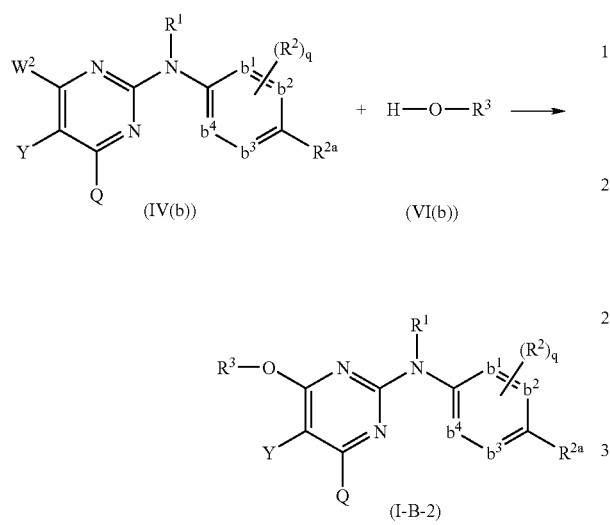

The compounds of formula (I-B) may further be prepared by converting compounds of formula (I-B) into each other according to art-known group transformation reactions.

The compounds of formula (I-B) may be converted to the corresponding N-oxide forms by the procedures described hereinabove.

For instance, the compounds of formula (I-B) wherein Q is a halogen may be converted to the corresponding compounds wherein Q is —$NR^4H$ using $NH_2R^4$ as a reagent in a reaction inert solvent such as, for example, 1,4-dioxane and the like, optionally in the presence of a suitable base such as, for example, triethylamine or N,N-diisopropyl-ethylamine or the like. In case $R^4$ contains a hydroxy moiety, it may be convenient to perform the above reaction with a protected form of $NH_2R^4$ whereby the hydroxy moiety bears a suitable protecting group P being, for instance, a trialkyl-silyl group, and subsequently removing the protective group according to art-known methodologies.

Some of the compounds of formula (I-B) and some of the intermediates in the present invention may contain an asymmetric carbon atom. Pure stereochemically isomeric forms of said compounds and said intermediates can be obtained by the application of art-known procedures. For example, diastereoisomers can be separated by physical methods such as selective crystallization or chromatographic techniques, e.g. counter current distribution, liquid chromatography and the like methods. Enantiomers can be obtained from racemic mixtures by first converting said racemic mixtures with suitable resolving agents such as, for example, chiral acids, to mixtures of diastereomeric salts or compounds; then physically separating said mixtures of diastereomeric salts or compounds by, for example, selective crystallization or chromatographic techniques, e.g. liquid chromatography and the like methods; and finally converting said separated diastereomeric salts or compounds into the corresponding enantiomers. Pure stereochemically isomeric forms may also be obtained from the pure stereochemically isomeric forms of the appropriate intermediates and starting materials, provided that the intervening reactions occur stereospecifically.

An alternative manner of separating the enantiomeric forms of the compounds of formula (I-B) and intermediates involves liquid chromatography, in particular liquid chromatography using a chiral stationary phase.

Some of the intermediates and starting materials are known compounds and may be commercially available or may be prepared according to art-known procedures.

Intermediates of formula (II(b)) wherein L is —X—$R^3$, said intermediates being represented by formula (II(b)-1), can be prepared by reacting a pyrimidine derivative of formula (VII(b)) wherein each $W^1$ is as defined previously, with $HXR^3$ (VIII(b)) in a reaction inert solvent such as, for example, 1,4-dioxane, 2-propanol or the like, and in the presence of a base such as, for example, triethylamine or N,N-diisopropylethyl-amine or the like. Different regio-specific isomers may be formed and can be separated from one another using suitable separation techniques such as, for example, chromatography.

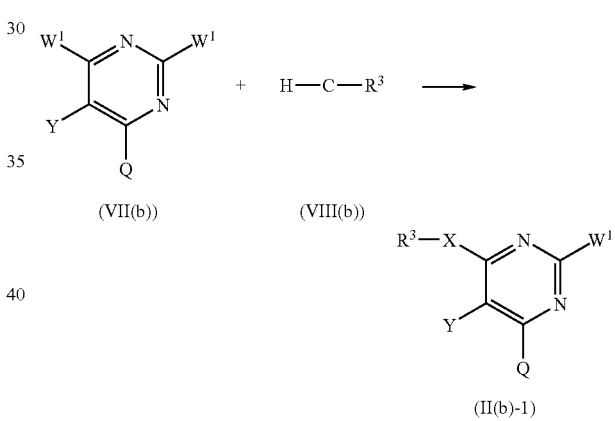

Intermediates of formula (IV(b)) can be prepared by reacting an intermediate of formula (VII(b)-a) wherein $W^2$ is a suitable leaving group such as, for example, a halogen, with an intermediate of formula (IX(b)) in a suitable solvent such as, for example, 1-methyl-2-pyrrolidinone, 1,4-dioxane or the like, in the presence of an acid such as, for example, 1 N hydrochloric acid in diethyl ether. This reaction can be performed at a temperature ranging between 50° C. and 250° C.

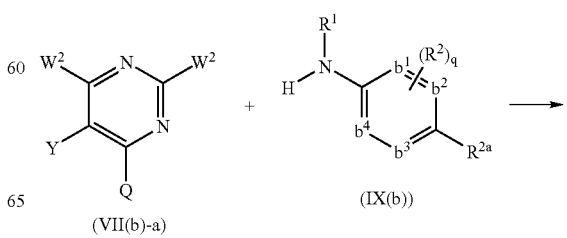

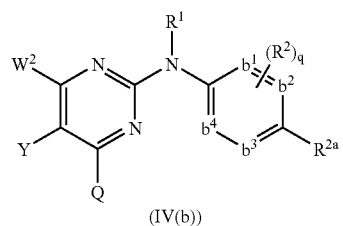

(IV(b))

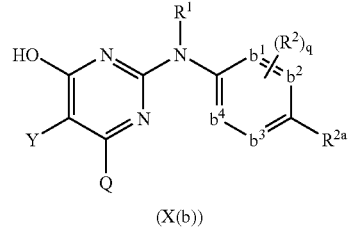

(X(b))

Alternatively, intermediates of formula (IV(b)) can be prepared by reacting an intermediate of formula (X(b)) with phosphorous oxychloride, triflic anhydride or a functional derivative thereof under a reaction-inert atmosphere such as, for example, oxygen free argon or nitrogen. This reaction can be performed at a temperature ranging between 20° C. and 150° C.

Intermediates of formula (X(b)) can also be prepared by reacting an intermediate of formula (XII(b)), wherein $W^2$ is a suitable leaving group and Y and Q are defined as described for a compound of formula (I-B), with an intermediate of formula (XIII(b)) in an appropriate solvent such as, for example, ethanol, or the like, and in the presence of a base such as, for example, sodium ethoxide or the like, under a reaction-inert atmosphere such as, for example, oxygen free argon or nitrogen. The reaction can be performed at a temperature ranging between 20° C. and 125° C.

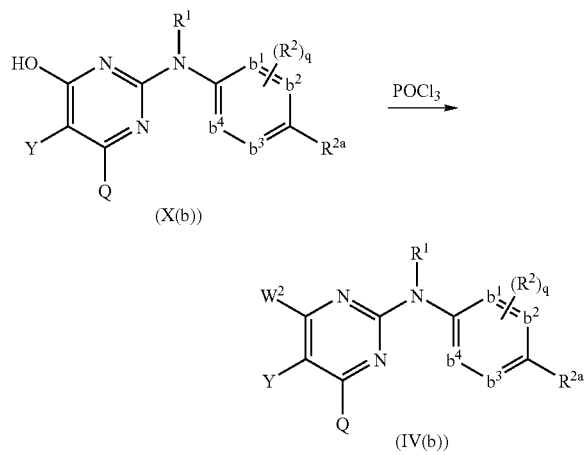

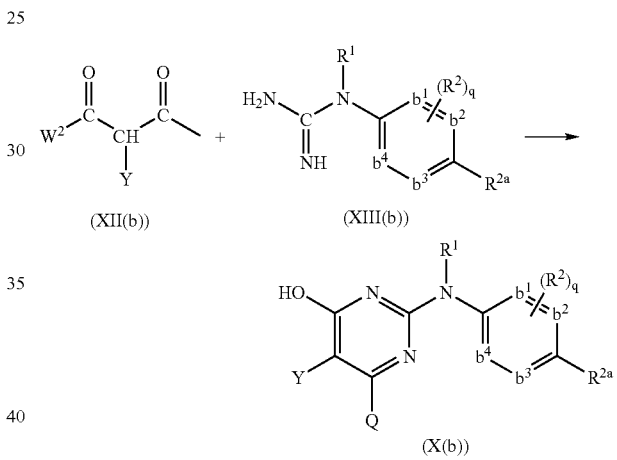

Intermediates of formula (X(b)) can be prepared by reacting an intermediate of formula (XI(b)) or a functional derivative thereof, with an intermediate of formula (IX(b)). This reaction may be performed under solvent-free conditions or in an appropriate solvent such as, for example, diglyme, tetraline or the like under a reaction-inert atmosphere such as, for example, oxygen free argon or nitrogen, and optionally in the presence of a base such as, for example, sodium hydride, potassium hydride or the like. This reaction can be performed at a temperature ranging between 100° C. and 250° C.

A convenient way of preparing an intermediate of formula (IV(b)) wherein Y is a bromine or chloro atom, said intermediates being represented by formula (IV(b)-1), involves the introduction of a bromine or chloro atom to an intermediate of formula (XIV(b)) using N-bromosuccinimide or N-chlorosuccinimide in a reaction-inert solvent such as, for example, chloroform, carbon tetrachloride or the like. This reaction can be performed at a temperature ranging between 20° C. and 125° C.

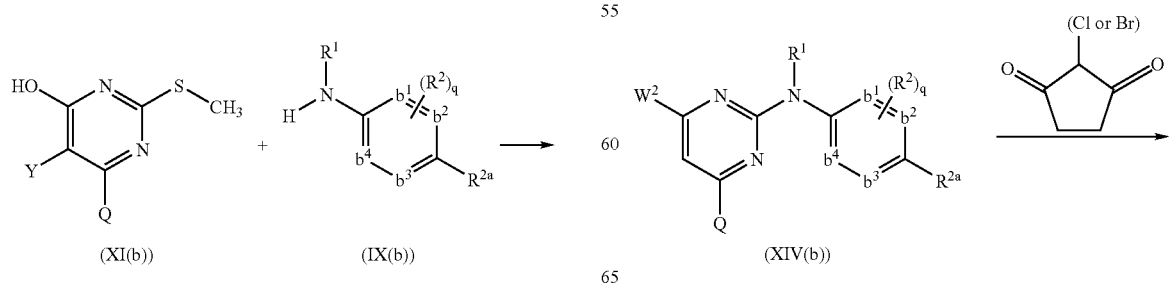

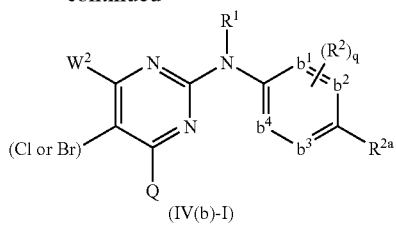

(IV(b)-I)

Analogous to the conversion of compounds of formula (I-B) wherein Q is a halogen to compounds of formula (I-B) wherein Q is —NHR⁴, the intermediates of formula (II(b)), (IV(b)) and (VII(b)) can also be converted.

Compounds of formula (I-C) wherein L is a radical of formula —X—R³, said compounds are represented by formula (I-C-a), can be prepared by reacting an intermediate of formula (II(c)) wherein W¹ is a suitable leaving group, for example, a halogen, with an amine derivative of formula (III(c)) in a reaction-inert solvent, for example, tetrahydrofuran, 1,4-dioxane or the like, in the presence of a suitable base such as, triethylamine; and subsequently reacting the thus obtained intermediate of formula (IV(c)) with an intermediate of formula (V(c)) in a reaction-inert solvent such as acetonitrile, 1,4-dioxane or the like, in the presence of a base such as potassium carbonate, sodium hydride, N,N-diisopropyl-ethylamine or the like.

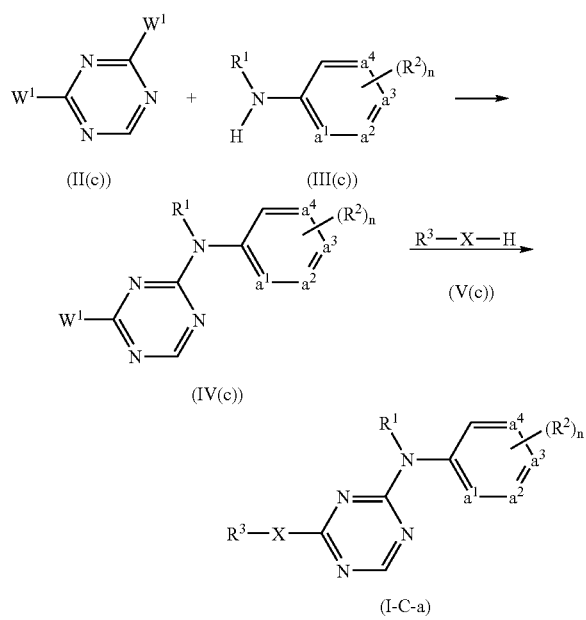

The order of the above reaction scheme may also be reversed, i.e. first an intermediate of formula (II(c)) may be reacted with an intermediate of formula (V(c)), and then, the resulting intermediate may further be reacted with an amine derivative of formula (III(c)); thus forming a compound of formula (I-C-a).

The reaction products may be isolated from the reaction medium and, if necessary, further purified according to methodologies generally known in the art such as, extraction, crystallization, distillation, trituration and chromatography.

Compounds of formula (I-C) wherein L is an optionally substituted $C_{1-10}$alkyl, $C_{2-10}$alkenyl, $C_{2-10}$alkynyl, $C_{3-7}$cycloalkyl, said compounds are represented by formula (I-C-b), can be prepared by first making a Grignard reagent of an intermediate of formula (VI(c)) wherein W² is a suitable substituent such as, a halogen, e.g. bromine, in the presence of magnesium in a reaction-inert solvent such as, diethyl ether, and subsequently reacting said Grignard reagent with an intermediate of formula (II(c)) wherein W¹ is a suitable leaving group such as, a halogen, e.g. chlorine, in a reaction-inert solvent, for example, benzene, thus forming an intermediate of formula (VII(c)). It may be convenient to perform the above reaction under a inert atmosphere, for instance, argon. Intermediate (VII(c)) may be isolated from its reaction medium, or may be in situ further reacted with an intermediate of formula (III(c)) in a reaction-inert solvent such as, 1,4-dioxane, and in the presence of a suitable base such as, diisopropylethylamine or the like, thus forming a compound of formula (I-C-b).

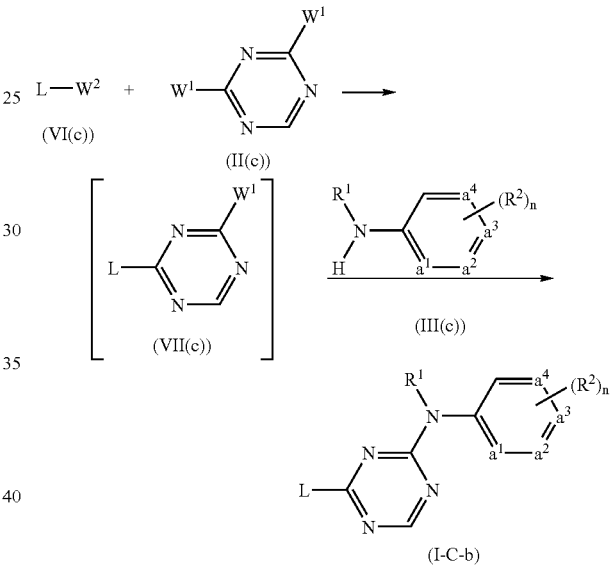

The compounds of formula (I-C) may further be prepared by converting compounds of formula (I-C) into each other according to art-known group transformation reactions.

The compounds of formula (I-C) may be converted to the corresponding N-oxides by the procedures as described hereinabove.

Some of the intermediates as mentioned hereinabove are commercially available or can be prepared according to art-known procedures.

Compounds of formula (I-C) and some of the intermediates may have one or more stereogenic centers in their structure, present in a R or a S configuration.

The compounds of formula (I-A), (I-B) or (I-C) as prepared in the hereinabove described processes may be synthesized as a mixture of stereoisomeric forms, in particular in the form of racemic mixtures of enantiomers which can be separated from one another following art-known resolution procedures. The racemic compounds of formula (I-A), (I-B) or (I-C) may be converted into the corresponding diastereomeric salt forms by reaction with a suitable chiral acid. Said diastereomeric salt forms are subsequently separated, for example, by selective or fractional crystallization and the enantiomers are liberated therefrom by alkali. An alternative manner of separating the enantiomeric forms of the compounds of formula (I-A), (I-B) or (I-C) involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound will be synthesized by stereospecific methods of preparation. These methods will advantageously employ enantiomerically pure starting materials.

It will be appreciated by those skilled in the art that in the processes described above the functional groups of intermediate compounds to prepare compounds of formula (I-A), (I-B) or (I-C) may need to be blocked by protecting groups.

Functional groups which it is desirable to protect include hydroxy, amino and carboxylic acid. Suitable protecting groups for hydroxy include trialkylsilyl groups (e.g. tert-butyldimethylsilyl, tert-butyldiphenylsilyl or trimethylsilyl), benzyl and tetrahydropyranyl. Suitable protecting groups for amino include tert-butyloxycarbonyl or benzyloxycarbonyl. Suitable protecting groups for carboxylic acid include $C_{1-6}$alkyl or benzyl esters.

The protection and deprotection of functional groups may take place before or after a reaction step.

The use of protecting groups is fully described in 'Protective Groups in Organic Chemistry', edited by J W F McOmie, Plenum Press (1973), and 'Protective Groups in Organic Synthesis' $2^{nd}$ edition, T W Greene & P G M Wutz, Wiley Interscience (1991).

The compounds of formula (I-A), (I-B) and (I-C) and the intermediates of formula (II'-a) unexpectedly show antiretroviral properties, in particular against Human Immunodeficiency Virus (HIV), which is the aetiological agent of Acquired Immune Deficiency Syndrome (AIDS) in humans. The HIV virus preferentially infects human T-4 cells and destroys them or changes their normal function, particularly the coordination of the immune system. As a result, an infected patient has an everdecreasing number of T-4 cells, which moreover behave abnormally. Hence, the immunological defense system is unable to combat infections and neoplasms and the HIV infected subject usually dies by opportunistic infections such as pneumonia, or by cancers. Other conditions associated with HIV infection include thrombocytopaenia, multiple sclerosis, Kaposi's sarcoma and infection of the central nervous system characterized by progressive demyelination, resulting in dementia and symptoms such as, progressive dysarthria, ataxia and disorientation. HIV infection further has also been associated with peripheral neuropathy, progressive generalized lymphadenopathy (PGL) and AIDS-related complex (ARC).

The compounds of formula (I-A), (I-B) and (I-C) also show activity against HIV-1 strains that have acquired resistance to art-known non-nucleoside reverse transcriptase inhibitors. They also have little or no binding affinity to human α-1 acid glycoprotein.

Those of skill in the treatment of HIV-infection could determine the effective daily amount from the test results presented here. In general it is contemplated that an effective daily amount would be from 0.01 mg/kg to 50 mg/kg body weight, more preferably from 0.1 mg/kg to 10 mg/kg body weight. It may be appropriate to administer the required dose as two, three, four or more sub-doses at appropriate intervals throughout the day. Said sub-doses may be formulated as unit dosage forms, for example, containing 1 to 1000 mg, in particular 5 to 600 mg of active ingredient per unit dosage form, and more in particular from 200 to 400 mg per unit dosage form or from 5 to 200 mg of active ingredient per unit dosage form depending on the particular compound being used.

The exact dosage and frequency of administration depends on the particular compound of formula (I-A), (I-B) or (I-C) used, the particular condition being treated, the severity of the condition being treated, the age, weight and general physical condition of the particular patient as well as other medication the individual may be taking, as is well known to those skilled in the art. Furthermore, it is evident that said effective daily amount may be lowered or increased depending on the response of the treated subject and/or depending on the evaluation of the physician prescribing the compounds of the instant invention. The effective daily amount ranges mentioned hereinabove are therefore only guidelines and are not intended to limit the scope or use of the invention to any extent.

The compounds of formula (I-A), (I-B) or (I-C) can also be used in the present invention in combination with another compound of formula (I-A), (I-B) or (I-C) or with another antiretroviral compound. Thus, the present invention also relates to a pharmaceutical composition containing (a) a compound of formula (I-A), (I-B) or (I-C), (b) another compound of formula (I-A), (I-B) or (I-C) or another antiretroviral compound, and (c) one or more water-soluble polymers, as a combined preparation for anti-HIV treatment. Said other antiretroviral compounds may be known antiretroviral compounds such as nucleoside reverse transcriptase inhibitors, e.g. zidovudine (3'-azido-3'-deoxythymidine, AZT), didanosine (dideoxy inosine; ddI), zalcitabine (dideoxycytidine, ddC) or lamivudine (3'-thia-2'-3'-dideoxycytidine, 3TC) and the like; non-nucleoside reverse transciptase inhibitors such as suramine, foscarnet-sodium (trisodium phosphono formate), nevirapine (11-cyclopropyl-5, 11-dihydro-4-methyl-6H-dipyrido[3,2-b: 2',3'-e] [1,4] diazepin-6-one), sustiva (efavirenz), tacrine (tetrahydroaminoacridine) and the like; compounds of the TIBO (tetrahydro-imidazo[4,5,1-jk][1,4]-benzodiazepine-2 (1H)-one and thione)-type e.g. (S)-8-chloro-4,5,6,7-tetrahydro-5-methyl-6-(3-methyl-2-butenyl)imidazo-[4,5,1-jk][1, 4]benzodiazepine-2(1H)-thione; compounds of the α-APA (α-anilino phenyl acetamide) type e.g. a-[(2-nitro-phenyl) amino]-2,6-dichlorobenzene-acetamide and the like; TAT-inhibitors, e.g. RO-5-3335 and the like; protease inhibitors e.g. indinavir, ritonavir, saquinovir and the like; NMDA receptor inhibitors e.g. pentamidine; α-glycosidase inhibitor e.g. castanospermine and the like; Rnase H inhibitor e.g. dextran (dextran sulfate) and the like; or immunomodulating agents, e.g. levamisole, thymopentin and the like.

The term "a solid dispersion" defines a system in a solid state (as opposed to a liquid or gaseous state) comprising at least two components, wherein one component is dispersed more or less evenly throughout the other component or components. When said dispersion of the components is such that the system is chemically and physically uniform or homogenous throughout or consists of one phase as defined in thermo-dynamics, such a solid dispersion will be called "a solid solution" hereinafter. Solid solutions are preferred physical systems because the components therein are usually readily bioavailable to the organisms to which they are administered. This advantage can probably be explained by the ease with which said solid solutions can form liquid solutions when contacted with a liquid medium such as gastric juice. The ease of dissolution may be attributed at least in part to the fact that the energy required for dissolution of the components from a solid solution is less than that required for the dissolution of components from a crystalline or microcrystalline solid phase.

The term "a solid dispersion" also comprises dispersions which are less homogenous throughout than solid solutions. Such dispersions are not chemically and physically uniform throughout or comprise more than one phase. For example, the term "a solid dispersion" also relates to particles having domains or small regions wherein amorphous, microcrystalline or crystalline (a), or amorphous, microcrystalline or crystalline (b), or both, are dispersed more or less evenly in another phase comprising (b), or (a), or a solid solution comprising (a) and (b). Said domains are regions within the particles distinctively marked by some physical feature, small in size compared to the size of the particle as a whole, and evenly and randomly distributed throughout the particle.

As described hereinabove, the particles of the present invention also comprise one or more water-soluble polymers.

The water-soluble polymer in the particles according to the present invention is a polymer that preferably has an apparent viscosity, when dissolved at 20° C. in an aqueous solution at 2% (w/v), of 1 to 5000 mPa·s more preferably of 1 to 700 mPa·s, and most preferred of 1 to 100 mPa·s. For example, the water-soluble polymer can be selected from the group comprising alkylcelluloses such as methylcellulose,
hydroxyalkylcelluloses such as hydroxymethylcellulose, hydroxyethylcellulose, hydroxypropylcellulose and hydroxybutylcellulose,
hydroxyalkyl alkylcelluloses such as hydroxyethyl methylcellulose and hydroxypropyl methylcellulose,
carboxyalkylcelluloses such as carboxymethylcellulose,
alkali metal salts of carboxyalkylcelluloses such as sodium carboxymethylcellulose,
carboxyalkylalkylcelluloses such as carboxymethylethylcellulose,
carboxyalkylcellulose esters,
starches,
pectines such as sodium carboxymethylamylopectine,
chitin derivates such as chitosan,
di-, oligo- and polysaccharides such as trehalose, cyclodextrins and derivatives thereof, alginic acid, alkali metal and ammonium salts thereof, carrageenans, galactomannans, tragacanth, agar—agar, gummi arabicum, guar gummi and xanthan gummi,
polyacrylic acids and the salts thereof,
polymethacrylic acids, the salts and esters thereof, methacrylate copolymers,
polyvinylalcohol,
polyalkylene oxides such as polyethylene oxide and polypropylene oxide and copolymers of ethylene oxide and propylene oxide.
Preferred water-soluble polymers are Eudragit E® and hydroxypropyl methylcelluloses (HPMC).

Said Eudragit E® (Röhm GmbH, Germany) is an aminoalkyl methacrylate copolymer, more in particular poly (butyl methacrylate, (2-dimethylaminoethyl)methacrylate, methyl methacrylate) (1:2:1). This basic polymethacrylate is soluble in gastric fluid up to pH 5. Eudragit E® 100, which is a solvent-free Eudragit E® solid substance is preferred.

Said HPMC contains sufficient hydroxypropyl and methoxy groups to render it water-soluble. HPMC having a methoxy degree of substitution from about 0.8 to about 2.5 and a hydroxypropyl molar substitution from about 0.05 to about 3.0 are generally water-soluble. Methoxy degree of substitution refers to the average number of methyl ether groups present per anhydroglucose unit of the cellulose molecule. Hydroxy-propyl molar substitution refers to the average number of moles of propylene oxide which have reacted with each anhydroglucose unit of the cellulose molecule. Hydroxypropyl methylcellulose is the United States Adopted Name for hypromellose (see Martindale, The Extra Pharmacopoeia, 29th edition, page 1435). In the four digit number "2910", the first two digits represent the approximate percentage of methoxyl groups and the third and fourth digits the approximate percentage composition of hydroxypropoxyl groups; 5 mPa·s is a value indicative of the apparent viscosity of a 2% aqueous solution at 20° C.

The molecular weight of the HPMC normally affects both the release profile of the milled extrudate as well as its physical properties. A desired release profile can thus be designed by choosing an HPMC of an appropriate molecular weight; for immediate release of the active ingredient from the particles, a low molecular weight polymer is preferred. High molecular weight HPMC is more likely to yield a sustained release pharmaceutical dosage form. The molecular weight of a water-soluble cellulose ether is generally expressed in terms of the apparent viscosity at 20° C. of an aqueous solution containing two percent by weight of said polymer. Suitable HPMC include those having a viscosity from about 1 to about 100 mPa·s, in particular form about 3 to about 15 mPa·s, preferably about 5 mPa·s The most preferred type of HPMC having a viscosity of 5 mPa·s., is the commercially available HPMC 2910 5 mPa·s, because this yields particles from which superior oral dosage forms of compounds of formula (I-A), (I-B) or (I-C) can be prepared as will be discussed hereunder and in the experimental part.

The weight-by-weight ratio of (a) (i.e. the antiviral compound): (b) (i.e. the water-soluble polymer) is in the range of 1:1 to 1:899, preferably 1:1 to 1:100, more preferably 1:1 to 1:5. In the case of (compound of formula (I-A), (I-B) or (I-C)): (HPMC 2910 5 mPa·s), said ratio preferably ranges from about 1:1 to about 1:3, and optimally is about 1:1.5 (or 2:3). The most appropriate weight by weight ratio of a compound of formula (I-A), (I-B) or (I-C) to water-soluble polymer(s) may be determined by a person skilled in the art by straightforward experimentation. The lower limit is determined by practical considerations. Indeed, given the therapeutically effective amount of a compound of formula (I-A), (I-B) or (I-C) (from about 1 mg to about 1000 mg per unit dosage form, preferably about 200 mg to 400 mg or 5 to 200 mg per unit dosage form), the lower limit of the ratio is determined by the maximum amount of mixture that can be processed into one dosage form of practical size. When the relative amount of water-soluble polymer is too high, the absolute amount of mixture needed to reach the therapeutic level will be too high to be processed into one capsule or tablet. Tablets, for example, have a maximum weight of about 1 g, and the extrudate can account for maximally about 90% (w/w) thereof. Consequently, the lower limit of the amount of a compound of formula (I-A), (I-B) or (I-C) over water-soluble polymer will be about 1:899 (1 mg of a compound of formula (I-A), (I-B) or (I-C)+899 mg water-soluble polymer).

On the other hand, if the ratio is too high, this means the amount of the compound of formula (I-A), (I-B) or (I-C) is relatively high compared to the amount of water-soluble polymer, then there is the risk that the compound of formula (I-A), (I-B) or (I-C) will not dissolve sufficiently in the water-soluble polymer, and thus the required bioavailability will not be obtained. The degree to which a compound has dissolved into a water-soluble polymer can often be checked visually: if the extrudate is clear then it is very likely that the compound will have dissolved completely in the water-soluble polymer. It will be appreciated that the upper limit of 1:1 may be underestimated for particular compounds of formula (I-A), (I-B) or (I-C) and particular water-soluble polymers. Since this can be established easily but for the experimentation time involved, solid dispersions wherein the ratio (a): (b) is larger than 1:1 are also meant to be comprised within the scope of the present invention.

The particles according to the present invention can be prepared by first preparing a solid dispersion of the components, and then optionally grinding or milling that dispersion. Various techniques exist for preparing solid dispersions including melt-extrusion, spray-drying and solution-evaporation, melt-extrusion being preferred.

The melt-extrusion process comprises the following steps:

a) mixing the components (a) and (b), b) optionally blending additives with the thus obtained mixture, c) heating the thus obtained blend until one obtains a homogenous melt, d) forcing the thus obtained melt through one or more nozzles; and e) cooling the melt till it solidifies.

The terms "melt" and "melting" should be interpreted broadly. For our purposes, these terms not only mean the alteration from a solid state to a liquid state, but can also refer to a transition to a glassy state or a rubbery state, and in which it is possible for one component of the mixture to get embedded more or less homogeneously into the other. In particular cases, one component will melt and the other component(s) will dissolve in the melt thus forming a solution, which upon cooling may form a solid solution having advantageous dissolution properties.

One of the most important parameters of melt extrusion is the temperature at which the melt-extruder is operating. It was found that the operating temperature can easily range between about 20° C. and about 300° C., more preferably about 70° C. and 250° C. The lower temperature limit depends on the solubility of a compound of formula (I-A), (I-B) or (I-C) in the water-soluble polymer and on the viscosity of the mixture. When the compound of formula (I-A), (I-B) or (I-C) is not completely dissolved in the water-soluble polymer, the extrudate will not have the required bioavailability; when the viscosity of the mixture is too high, the process of melt extrusion will be difficult. At temperatures of more than 300° C. the water-soluble polymer may decompose to an unacceptable level. It may be noted that there is no need to fear decomposition of a compound of formula (I-A), (I-B) or (I-C) at temperatures up to 300° C. A person skilled in the art will easily recognize the most appropriate temperature range to be used.

The throughput rate is also of importance because even at relatively low temperatures the water-soluble polymer may start to decompose when it remains too long in contact with the heating element.

It will be appreciated that the person skilled in the art will be able to optimize the parameters of the melt extrusion process within the above given ranges. The working temperatures will also be determined by the kind of extruder or the kind of configuration within the extruder that is used. Most of the energy needed to melt, mix and dissolve the components in the extruder can be provided by the heating elements.

However, the friction of the material within the extruder may also provide a substantial amount of energy to the mixture and aid in the formation of a homogenous melt of the components.

A person skilled in the art will easily recognize the most appropriate extruder, such as, for example, a single screw, a twin screw extruder or a multi-screw extruder, for the preparation of the subject-matter of the present invention.

Spray-drying of a solution of the components also yields a solid dispersion of said components and may be a useful alternative to the melt-extrusion process, particularly in those cases where the water-soluble polymer is not sufficiently stable to withstand the extrusion conditions and where residual solvent can effectively be removed from the solid dispersion. Yet another possible preparation consists of preparing a solution of the components, pouring said solution onto a large surface so as to form a thin film, and evaporating the solvent therefrom.

The solid dispersion product is milled or ground to particles having a particle size of less than 1500 μm, preferably less than 400 μm, more preferably less than 250 μm, and most preferably less than 125 μm. The particle size proves to be an important factor determining the speed with which a particular dosage form can be manufactured on a large scale. For instance, for capsules, the particle size may range preferably from 100 to 1500 μm; for tablets the particle size is preferably less than 250 μm. The smaller the particles, the faster the tabletting speed can be without detrimental effects on their quality. The particle size distribution is such that more than 70% of the particles (measured by weight) have a diameter ranging from about 50 μm to about 1400 μm, in particular from about 50 μm to about 200 μm, more in particular from about 50 μm to about 150, and most in particular from about 50 μm to about 125 μm. Particles of the dimensions mentioned herein can be obtained by sieving them through nominal standard test sieves as described in the CRC Handbook, $64^{th}$ ed., page F-114. Nominal standard sieves are characterized by the mesh/hole width (μm), DIN 4188 (mm), ASTM E 11-70 (No), Tyler® (mesh) or BS 410 (mesh) values. Throughout this description, and in the claims hereinafter, particle sizes are designated by reference to the mesh/hole width in μm and to the corresponding Sieve No. in the ASTM E11-70 standard.

Preferred are particles wherein the compound of formula (I-A), (I-B) or (I-C) is in a non-crystalline phase as these have an intrinsically faster dissolution rate than those wherein part or all of the compound of formula (I-A), (I-B) or (I-C) is in a microcrystalline or crystalline form.

Preferably, the solid dispersion is in the form of a solid solution comprising (a) and (b). Alternatively, it may be in the form of a dispersion wherein amorphous or microcrystalline (a) or amorphous or microcrystalline (b) is dispersed more or less evenly in a solid solution comprising (a) and (b).

Preferred particles are those obtainable by melt-extrusion of the components and grinding, and optionally sieving. More in particular, the present invention concerns particles consisting of a solid solution comprising two parts by weight of a compound of formula (I-A), (I-B) or (I-C) and three parts by weight of hydroxypropyl methylcellulose HPMC 2910 5 mPa·s, obtainable by blending said components, melt-extruding the blend at a temperature in the range of 20° C.–300° C., grinding the extrudate, and optionally sieving the thus obtained particles. The preparation is easy to perform and yields particles of a compound of formula (I-A), (I-B) or (I-C) that are free of organic solvent.

The particle as described hereinabove may further comprise one or more pharmaceutically acceptable excipients such as, for example, plasticizers, flavors, colorants, preservatives and the like. Said excipients should not be heat-sensitive, in other words, they should not show any appreciable degradation or decomposition at the working temperature of the melt-extruder.

In the current formulations (compound of formula (I-A), (I-B) or (I-C):HPMC 2910 5 mPa·s), the amount of plasticizer is preferably small, in the order of 0% to 15% (w/w), preferably less than 5% (w/w). With other water-soluble polymers though, plasticizers may be employed in much different, often higher amounts because plasticizers as mentioned hereinbelow lower the temperature at which a melt of (a), (b) and plasticizer is formed, and this lowering of the melting point is advantagous where the polymer has limited thermal stability. Suitable plasticizers are pharmaceutically acceptable and include low molecular weight polyalcohols such as ethylene glycol, propylene glycol, 1,2 butylene glycol, 2,3-butylene glycol, styrene glycol; polyethylene glycols such as diethylene glycol, triethylene glycol, tetra-ethylene glycol; other polyethylene glycols having a molecular weight lower than 1,000 g/mol; polypropylene glycols having a molecular weight lower than 200 g/mol; glycol ethers such as monopropylene glycol monoisopropyl ether; propylene glycol monoethyl ether; diethylene glycol monoethyl ether; ester type plasticizers such as sorbitol lactate, ethyl lactate, butyl lactate, ethyl glycolate, allyl glycollate; and amines such as monoethanolamine, diethanolamine, triethanolamine, monoisopropanolamine; triethylenetetramine, 2-amino-2-methyl-1,3-propanediol and the like. Of these, the low molecular weight polyethylene glycols, ethylene glycol, low molecular weight polypropylene glycols and especially propylene glycol are preferred.

Once the extrudate is obtained, it can be milled and sieved, and it can be used as ingredient to make pharmaceutical dosage forms.

The particles of the present invention can be formulated into pharmaceutical dosage forms comprising a therapeutically effective amount of particles. Although, at first instance, pharmaceutical dosage forms for oral administration such as tablets and capsules are envisaged, the particles of the present invention can also be used to prepare pharmaceutical dosage forms e.g. for rectal administration. Preferred dosage forms are those adapted for oral administration shaped as a tablet. They can be produced by conventional tabletting techniques with conventional ingredients or excipients and with conventional tabletting machines. As mentioned above, an effective antiviral dose of a compound of formula (I-A), (I-B) or (I-C) ranges from about 1 mg to about 1000 mg per unit dosage form, and preferably is about 200 to 400 mg or 5 to 200 mg per unit dosage form depending on the particular compound being used. When one considers that the weight-by-weight ratio of (a): (b) is maximally about 1:1, then it follows that one dosage form will weigh at least 10 to 800 mg. In order to facilitate the swallowing of such a dosage form by a mammal, it is advantageous to give the dosage form, in particular tablets, an appropriate shape. Tablets that can be swallowed comfortably are therefore preferably elongated rather than round in shape. Especially preferred are biconvex oblate tablets. As discussed hereunder in more detail, a film coat on the tablet further contributes to the ease with which it can be swallowed.

Tablets that give an immediate release of a compound of formula (I-A), (I-B) or (I-C) upon oral ingestion and that have good bioavailability are designed in such a manner that the tablets disintegrate rapidly in the stomach (immediate release) and that the particles which are liberated thereby are kept away from one another so that they do not coalesce, give local high concentrations of a compound of formula (I-A), (I-B) or (I-C) and the chance that the drug precipitates (bioavailability). The desired effect can be obtained by distributing said particles homogeneously throughout a mixture of a disintegrant and a diluent.

Suitable disintegrants are those that have a large coefficient of expansion. Examples thereof are hydrophilic, insoluble or poorly water-soluble crosslinked polymers such as crospovidone (crosslinked polyvinylpyrrolidone) and croscarmellose (crosslinked sodium carboxymethylcellulose). The amount of disintegrant in immediate release tablets according to the present invention may conveniently range from about 3 to about 15% (w/w) and preferably is about 7 to 9%, in particular about 8.5% (w/w). This amount tends to be larger than usual in tablets in order to ensure that the particles are spread over a large volume of the stomach contents upon ingestion. Because disintegrants by their nature yield sustained release formulations when employed in bulk, it is advantageous to dilute them with an inert substance called a diluent or filler.

A variety of materials may be used as diluents or fillers. Examples are spray-dried or anhydrous lactose, sucrose, dextrose, mannitol, sorbitol, starch, cellulose (e.g. microcrystalline cellulose Avicel™), dihydrated or anhydrous dibasic calcium phosphate, and others known in the art, and mixtures thereof. Preferred is a commercial spray-dried mixture of lactose monohydrate (75%) with microcrystalline cellulose (25%) which is commercially availble as Microcelac™. The amount of diluent or filler in the tablets may conveniently range from about 20% to about 40% (w/w) and preferably ranges from about 25% to about 32% (w/w).

The tablet may include a variety of one or more other conventional excipients such as binders, buffering agents, lubricants, glidants, thickening agents, sweetening agents, flavors, and colors. Some excipients can serve multiple purposes.

Lubricants and glidants can be employed in the manufacture of certain dosage forms, and will usually be employed when producing tablets. Examples of lubricants and glidants are hydrogenated vegetable oils, e.g hydrogenated Cottonseed oil, magnesium stearate, stearic acid, sodium lauryl sulfate, magnesium lauryl sulfate, colloidal silica, talc, mixtures thereof, and others known in the art. Interesting lubricants and glidants are magnesium stearate, and mixtures of magnesium stearate with colloidal silica. A preferred lubricant is hydrogenated vegetable oil type I, most preferably hydrogenated, deodorized Cottonseed oil (commercially available from Karlshamns as Akofine NF™ (formerly called Sterotex™)). Lubricants and glidants generally comprise 0.2 to 7.0% of the total tablet weight.

Other excipients such as coloring agents and pigments may also be added to the tablets of the present invention. Coloring agents and pigments include titanium dioxide and dyes suitable for food. A coloring agent is an optional ingredient in the tablet of the present invention, but when used the coloring agent can be present in an amount up to 3.5% based on the total tablet weight.

Flavors are optional in the composition and may be chosen from synthetic flavor oils and flavoring aromatics or natural oils, extracts from plants leaves, flowers, fruits and so forth and combinations thereof. These may include cinnamon oil, oil of wintergreen, peppermint oils, bay oil, anise oil, eucalyptus, thyme oil. Also useful as flavors are vanilla, citrus oil, including lemon, orange, grape, lime and grape-fruit, and fruit essences, including apple, banana, pear, peach, strawberry, raspberry, cherry, plum, pineapple, apricot and so forth, The amount of flavor may depend on a number of factors including the organoleptic effect desired. Generally the flavor will be present in an amount from about 0% to about 3% (w/w).

As known in the art, tablet blends may be dry-granulated or wet-granulated before tabletting. The tabletting process itself is otherwise standard and readily practised by forming a tablet from desired blend or mixture of ingredients into the appropriate shape using a conventional tablet press.

Tablets of the present invention may further be film-coated to improve taste, to provide ease of swallowing and an elegant appearance. Many suitable polymeric film-coating materials are known in the art. A preferred film-coating material is hydroxypropyl methylcellulose HPMC, especially HPMC 2910 5 mPa·s. Other suitable film-forming polymers also may be used herein, including, hydroxypropylcellulose, and acrylate-methacrylate copolymers. Besides a film-forming polymer, the film coat may further comprise a plasticizer (e.g. propylene glycol) and optionally a pigment (e.g. titanium dioxide). The film-coating suspension also may contain talc as an anti-adhesive. In immediate release tablets according to the invention, the film coat is small and in terms of weight accounts for less than about 3% (w/w) of the total tablet weight.

Preferred dosage forms are those wherein the weight of the particles is at least 40% of the total weight of the total dosage form, that of the diluent ranges from 20 to 40%, and that of the disintegrant ranges from 3 to 10%, the remainder being accounted for by one or more of the excipients described hereinabove.

The present invention further concerns a process of preparing particles as described hereinbefore, characterized by blending the components, extruding said blend at a temperature in the range of 20–300° C., grinding the extrudate, and optionally sieving the particles.

The invention also concerns solid dispersions obtainable by melt-extrusion of (a) a compound of formula (I-A), (I-B) or (I-C) or one of its stereoisomers or a mixture of two or more of its stereoisomers, and (c) one or more pharmaceutically acceptable water-soluble polymers.

It is another object of the invention to provide a process of preparing a pharmaceutical dosage form as described hereinbefore, characterized by blending a therapeutically effective amount of particles as described hereinbefore, with pharmaceutically acceptable excipients and compressing said blend into tablets or filling said blend in capsules.

Further, this invention concerns particles as described hereinbefore, for use in preparing a pharmaceutical dosage form for oral administration to a mammal suffering from a viral infection, wherein preferably a single such dosage form can be administered once daily to said mammal.

The present invention also concerns the use of particles according to as described hereinbefore, for the preparation of a pharmaceutical dosage form for oral administration to a mammal suffering from a viral infection, wherein preferably a single such dosage form can be administered once daily to said mammal.

The invention also relates to a method of treating a viral infection in a mammal which comprises administering to said mammal an effective antiviral amount of a compound of formula (I-A), (I-B) or (I-C), preferably in a single oral dosage form which can be administered once daily.

The invention also relates to a pharmaceutical package suitable for commercial sale comprising a container, an oral dosage form of a compound of formula (I-A), (I-B) or (I-C) as described hereinbefore, and associated with said package written matter.

The following examples are intended to illustrate the present invention.

EXPERIMENTAL PART

1. Compounds of Formula (I-A)

1.A. Preparation of Intermediate Compounds

Example 1.A1 a) A solution of 2,6-dichlorobenzylchloride (0.102 mol) in 1,1-diethylether (10 ml) was added dropwise to magnesium (0.102 mol) in 1,1-diethylether (60 ml). The reaction was initiated by adding 2 drops of 1,2-dibromoethane. After most of magnesium disappeared, 2,4,6-trichloropyrimidine (0.051 mol) in 1,1-diethylether (30 ml) was added. The mixture was stirred overnight at room temperature. The solvent was evaporated and the residue was purified by flash column chromatography over silica gel (eluent: $CH_2Cl_2$/hexane 1/2). The desired fractions were collected and the solvent was evaporated, yielding 3.3 g of (21%) 2,4-dichloro-6-[(2,6-dichloro-phenyl)methyl]pyrimidine (interm. 1; melting point (mp.): 106–107° C.).

b) Intermediate (1) (0.0081 mol) in 2-propanol (100 ml) was heated until complete dissolution. The solution was then transferred into a pressure tube and $NH^3$ gas was bubbled into it for 20 minutes. Then the mixture was heated to 80° C. for 16 hours. The solvent was evaporated, yielding a residue of two compounds: 2-chloro-6-[(2,6-di-chloro-phenyl)methyl]-4-pyrimidinamine (interm. 2) and 4-chloro-6-[(2,6-dichloro-phenyl)methyl]-2-pyrimidinamine (interm. 3).

Example 1.A2 a) Urea (0.03 mol) was added to a mixture of (±)-ethyl 2,6-dichloro-phenyl-α-methyl-β-oxobutanoate (0.02 mol) in $NaOC_2H_5$ in ethanol, (1M; 0.040 mol; 40 ml). The reaction mixture was stirred and refluxed overnight. The solvent was evaporated, water was added and the mixture was neutralized with 0.3 N HOAc. The precipitate was filtered off and was further triturated with ether and then $H_2O$, then filtered off and dried, yielding 2.2 g (39%) of 6-[(2,6-dichloro-phenyl)methyl]-5-methyl-2,4(1H,3H)-pyrimidinedione (interm. 4).

b) A mixture of intermediate (4) (0.0095 mol) in phosphoryl chloride (50 ml) was stirred and refluxed overnight. Excess of phosphoryl chloride was then evaporated. Ice-water was added to the residue. A white precipitate was formed, filtered off and dried. The residue was purified by flash column chromatography over silica gel (eluent: $CH_2Cl_2$). The desired fractions were collected and the solvent was evaporated, yielding 2.06 g (67%) of 2,4-dichloro-6-[(2,6-dichloro-phenyl)methyl]-5-methyl-pyrimidine (interm. 5).

c) 4-chloro-6-[(2,6-dichloro-phenyl)methyl]-5-methyl-2-pyrimidinamine (interm. 6) and 2-chloro-6-[(2,6-dichloro-phenyl)methyl]-5-methyl-4-pyrimidinamine (interm. 7) were prepared from intermediate 5 following the procedures as described in example A1b.

Example 1.A3 a) To the stirred solution of 2,6-dichlorobenzeneethanimidamide HCl (1:1), (0.0042 mol) in ethanol (20 ml), a solution of sodium (0.013 mol) in ethanol (10 ml) was added dropwise first and then propanedioic acid, diethyl ester (0.0109 mol) was added. The reaction mixture was stirred and refluxed for 4 hours and then stirred at room temperature overnight After adding another equivalent of propanedioic acid, diethyl ester (stirring and refluxing it overnight), the solvent was evaporated and the residue was dissolved in water and acidified with 1 N HCl. The solid was filtered off, washed with water and dried, yielding 0.87 g (76.4%) of 2-[(2,6-dichloro-phenyl)methyl]-4,6-pyrimidinediol (interm. 8).

b) 6-chloro-2-[(2,6-dichloro-phenyl)methyl]-4-pyrimidinamine (interm. 9) was prepared starting from intermediate 8 according to the procedures described in example A1b), A2b) & A2c).

Example 1.A4

4-Amino-1-butanol (1.57 ml) was added to a solution of intermediate (1) (0.008 mol) in 1,4-dioxane (20 ml) under Argon. The reaction mixture was stirred for 2 hours at room temperature. The solvent was evaporated. The residue was purified by flash column chromatography over silica gel (eluent gradient: $CH_2Cl_2/CH_3OH$: from 100/0 to 98/2). The pure fractions were collected and the solvent was evaporated, yielding 2.05 g of a mixture of 4-[[2-chloro-6-[(2,6-dichloro-phenyl)methyl]-4-pyrimidinyl]-amino]-1-butanol (interm. 10) and 4-[[4-chloro-6-[(2,6-dichloro-phenyl)methyl]-2-pyrimidinyl]amino]-1-butanol (interm. 11).

Example 1.A5 a) Potassium hydroxide/ethanol (10%; 0.035 mol) was added to a solution of 2,6-dichlorophenol (0.035 mol) in tetrahydrofuran (100 ml). The mixture was stirred and 2,4,6-trichloropyrimidine (0.044 mol) was added. The mixture was stirred overnight at 60° C. The reaction was quenched with NaOH 1N solution. The aqueous layers were extracted with EtOAc several times and then the organic layers were combined and washed with NaOH 3N and saturated NaCl, dried and concentrated. The residue was recrystallized from $CH_2Cl_2$/hexane. The precipitate was filtered off and dried, yielding 5.98 g 2,4-dichloro-6-(2,6-dichlorophenoxy)pyrimidine (55%) (interm. 12).

b) Reaction under Argon atmosphere. 2,4,6-trimethylaniline (0.0678 mol) was added to 2,4-dichloropyrimidine (0.0664 mol) in 1,4-dioxane (100 ml). N,N-di(1-methylethyl)-ethaneamine (0.0830 mol) was added. The reaction mixture was stirred and refluxed for 4 days and the solvent was evaporated. The residue was dissolved in $CH_2Cl_2$, washed with a saturated $NaHCO_3$ solution, then dried ($Na_2SO_4$), filtered and the solvent was evaporated to give 17.1 g solid residue. This solid was dissolved in $CH_2Cl_2$:hexane (1:1; 150 ml), and the resulting solution was concentrated to 100 ml, then filtered. The residue was purified by column chromatography on KP-Sil (eluent: $CH_2Cl_2$). The desired fractions were collected and the solvent was evaporated. The less polar fraction was stirred in $CH_2Cl_2$ for 3 hours and filtered, yielding 0.44 g 4-chloro-N-(2,4,6-trimethylphenyl)-2-pyrimidinamine (intermediate 10). A second fraction was recrystallized from acetonitrile, filtered off and dried, yielding 2-chloro-N-(2,4,6-trimethyl-phenyl)-4-pyrimidinamine (intermediate 14).

Example 1.A6

Pyridine (1 ml) was added to a mixture of 4-[[4-amino-6-[(2,6-dichloro-phenyl)-methyl]-2-pyrimidinyl]amino] benzonitrile (0.00135 mol) in $CH_2Cl_2$ (19 ml). A solution of chloroethanoyl chloride (0.001375 mol) in $CH_2Cl_2$ (0.5 mol) was added dropwise on an ice bath. The mixture was stirred at room temperature for 2 hours. More chloroethanoyl chloride (0.00625 mol) in $CH_2Cl_2$ (0.5 ml) was added. The mixture stood in the refrigerator overnight. The solvent was evaporated. The residue was treated with a saturated $Na_2CO_3$ solution and the mixture was extracted with $CH_2Cl_2$. The separated organic layer was dried, filtered and concentrated. The residue was purified by flash column chromatography over silica gel (eluent: $CH_2Cl_2/CH_3OH/NH_4OH$ 99/1/0.1). The desired fractions were collected and the solvent was evaporated, yielding 0.22 g (36.5%) of 2-chloro-N-[6-[(2, 6-dichloro-phenyl)methyl]-2-[(4-cyano-phenyl)amino]-4-pyrimidinyl]acetamide (interm. 13).

Example 1.A7

A mixture of 4-[(4-chloro-2-pyrimidinyl)amino]benzonitrile (0.005 mol) and nitryl tetrafluoroborate (0.0025 mol) in acetonitrile (5 ml) was stirred at room temperature for 4 h. The material was quenched with saturated bicarbonate (50 ml) on cracked ice. The mixture was allowed to reach room temperature, and the yellow solid was filtered off. The solid was adsorbed onto silica and purified by column chromatography (eluent: 30%, 50%, 60%, 70% $CH_2Cl_2$ in hexanes). The solvent of the desired fraction was evaporated and the residue was dried, yielding 0.89 g (64%) of 3-nitro-4-[(4-chloro-2-pyrimidinyl)amino]benzonitrile.(interm. 15)

Example 1.A8

A mixture of 2,6-dichloro-N-(2,4,6-trimethylphenyl)-4-pyrimidinamine (0.00376 mol) in a 2.0 M solution of $NH_3$ in 2-propanol (25 ml) and a 0.5 M solution of $NH_3$ in dioxane (25 ml) was heated in a pressure sample at 110–115° C. for 24 hours. The solvent was evaporated, and the residue was chromatographed on Biotage (eluent: 1:1 $CH_2Cl_2$: hexane). The desired fractions were collected and the solvent was evaporated, yielding a mixture of 0.523 g of 2-chloro-N4-(2,4,6-trimethylphenyl)-4,6-pyrimidine-diamine (interm. 53) and 0.101 g of 6-chloro-N4-(2,4,6-trimethylphenyl)-2,4-pyrimidinediamine. (interm. 16)

Example 1.A9 a) 2,4,6-trichloro-1,3,5-triazine (0.07440 mol) and tetrahydrofuran (100 ml) were combined and cooled to −75° C. under Ar atmosphere. 4-Aminobenzonitrile (0.07440 mol) was added and the solution was stirred for 4 hours at −75° C. Triethyl-amine (0.07440 mol) was added dropwise and the reaction mixture was allowed to warm up slowly to room temperature and stirred for 3 days. After adding 1,4-dioxane (100 ml), the resulting precipitate was collected by filtration, washed with tetrahydrofuran, and dried, yielding 12.74 g 4-[(4,6-dichloro-1,3,5-triazin-2-yl)amino]benzonitrile (interm. 17).

b) NaH (0.0113 mol), $CH_3CN$ (30 ml) and 2,6-dichlorophenol (0.0113 mol) were combined and stirred for 15 minutes under Ar atmosphere. Intermediate (17) (0.0113 mol) was added and the reaction mixture was stirred at room temperature for 16 hours. The reaction mixture was quenched with ice water (30 ml) and filtered. A precipitate formed in the filtrate and was filtered off. The resulting solid was washed with $H_2O$ and $CH_3CN$, then dried, yielding 0.62 g (14.0%) of 4-[[4-chloro-6-(2,6-dichloro-phenoxy)-1,3,5-triazin-2-yl]amino]benzonitrile (interm. 18).

c) N,N-Diisopropylethylamine (0.00714 mol) was added to a solution of 2-chloro-6-methylbenzenamine (0.00714 mol) in 1,4-dioxane (20 ml) under Ar flow. A solution of intermediate (17) (0.00714 mol) in 1,4-dioxane (5 ml) was added. The reaction mixture was stirred and refluxed for 24 hours. The solvent was evaporated and $CH_2Cl_2$ was added. The organic layer was washed with a saturated aqueous $NaHCO_3$ solution, and the resulting precipitate was filtered, yielding 0.56 g (21.1%) of 4-[[4-chloro-6-[(2-chloro-6-methylphenyl)amino]-1,3,5-triazin-2-yl]amino]benzonitrile (interm. 19).

Example 1.A10 a) 2,4,6-Trichloro-1,3,5-triazine (0.0266 mol) was added to 1,4-dioxane (50 ml) under Ar atmosphere. The solution was stirred until it became homogeneous, then 2,6-dichlorobenzenamine (0.0266 mol) and $K_2CO_3$ (0.0362 mol) were added. The reaction mixture was stirred at room temperature for 3 days. The solvent was evaporated. Water was added to the residue and the aqueous phase was extracted with $CH_2Cl_2$. The separated organic layer was washed with brine, dried with potassium carbonate, filtered and the filtrate was evaporated, yielding 7.52 g (91.2%) of N-(2,6-dichlorophenyl)-4,6-dichloro-1,3,5-triazin-2-amine (interm. 20).

b) 1,4-Dioxane (50 ml), 4-cyanoaniline (0.0243 mol), and N,N-diisopropylethylamine (0.0243 mol) were added to intermediate (20) (0.0243 mol) under Ar atmosphere. The reaction mixture was stirred and refluxed for 1 week. The reaction was cooled, the solvent was evaporated and the residue was dissolved in ethyl acetate. The organic phase was washed with a saturated $NaHCO_3$ solution and with brine, dried with potassium carbonate, filtered, and the solvent was evaporated. The residue was stirred in a mixture of $CH_2Cl_2$ and saturated $NaHCO_3$, and the precipitate filtered, yielding 2.26 g (23.8%) of 4-[[4-chloro-6-[(2,6-dichlorophenyl)amino]-1,3,5-triazin-2-yl]amino]benzonitrile (interm. 21).

Example 1.A11

Rink Amide resin (15 g; Calbiochem-Novabiochem Corp., San Diego, Calif.; Product No. 01–64-0013) was washed in a reaction vessel with $CH_2Cl_2$ (100 ml), N,N-dimethylformamide (200 ml), and N,N-dimethylformamide:piperidine (150 ml:50 ml) was added. The mixture was agitated for 2 hours, washed with N,N-dimethyl-formamide, $CH_2Cl_2$, and dimethylsulfoxide. Intermediate (17) (0.06 mol), N,N-diisopropylethylamine (10.5 ml) and dimethylsulfoxide (200 ml) were added and the reaction mixture was agitated for three days, then washed with N,N-dimethylformamide and $CH_2Cl_2$, yielding the resin bound intermediate (17).

1.B. Preparation of Compounds of Formula (I-A)

Example 1.B1

A mixture of

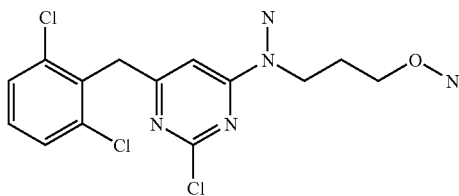

(*1.A4)

and

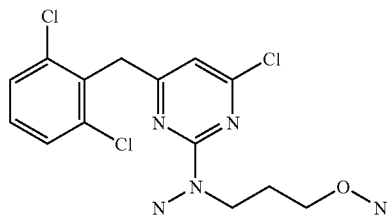

(*1.A4) (0.004 mol) and 4-amino-benzonitrile (0.0084 mol) were combined in a sealed tube and heated for 16 hours at 160° C. under Argon. The reaction mixture was allowed to cool to room temperature and dissolved in $CH_2Cl_2/CH_3OH$ 90/10 (20 ml) and 5 g of silica gel was added. After evaporating the solvent, the residue was purified by flash column chromatography over silica gel (eluent gradient: $CH_2Cl_2/CH_3OH$: from 100/0 to 97/3). The desired fraction was collected and the solvent was evaporated, yielding 0.31 g (18.1%) of 4-[[4-[(2,6-dichloro-phenyl)methyl]-6-[(3-hydroxypropyl)amino]-2-pyrimidinyl]amino]benzonitrile (comp. 4). (* indicates the example number according to which the intermediate was synthesized)

Example 1.B2

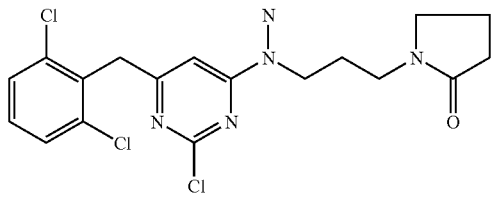

(*1.A4) and

Example 1.B4

A slurry of

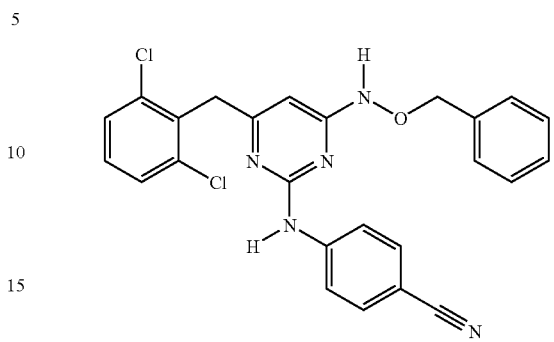

(*1.A2b) (0.005 mol) in CH$_2$Cl$_2$ (150 ml) was stirred rapidly and cooled to 0° C. under nitrogen. BBr$_3$ (0.015 mol) was introduced by syringe. The reaction mixture was stirred rapidly for two hours. The reaction mixture was recooled to 0° C. and quenched with NaOH (aq. 1 N, 25 ml). The biphasic partial quench mixture gives a precipitate which was filtered off and dried, yielding 2.5 g(91%) of 4-[[4-[(2,6-dichloro-phenyl)methyl]-6-(hydroxyamino)-2-pyrimidinyl]amino]benzonitrile dihydrobromide pentahydrate (comp. 12; mp. 240–244° C.).

Example 1.B5

1,1-Dimethoxy-N,N-dimethylmethanamine (0.152 mol) was added to 4-[[4-amino-6-[(2,6-dichlorophenyl)methyl]-2-pyrimidinyl]amino]benzonitrile (0.0008 mol). The mixture was stirred at room temperature for 2 days and then concentrated. The crude product was purified by flash chromatography over silica gel (eluent: CH$_2$Cl$_2$/CH$_3$OH 99/1). The desired fraction was collected and the solvent was evaporated. The resulting residue was triturated with hexane, yielding 0.15 g (42%) of N'-[2-[(4-cyano-phenyl)amino]-6-[(2,6-dichlorophenyl)methyl]-4-pyrimidinyl]-N,N-dimethylmethan-imidamide (mp. 175–180° C.).

Example 1.B6

Piperidine (0.12 ml) was added to a mixure of intermediate (13) (0.00047 mol) in terahydrofuran (20 ml). The mixture was stirred at room temperature for 4 hours. More piperidine (0.14 ml) was added. The mixture was stirred for another 2 hours. The solvent was evaporated. The residue was purified by flash column chromatography over silica gel (CH$_2$Cl$_2$/CH$_3$OH/NH$_4$OH 99/1/0.1). The desired fractions were collected and the solvent was evaporated, yielding 0.05 g (21.5%) of N-[6-[(2,6-di-chloro-phenyl)methyl]-2-[(4-cyano-phenyl)amino]-4-pyrimidinyl]-1-piperidine-acetamide (mp. 175–180° C.).

Example 1.B7

Pyridine (0.014 mol) was added to a mixture of 4-[[4-amino-6-[(2,6-dichlorophenyl)-methyl]-2-pyrimidinyl]amino]benzonitrile (0.0013 mol) in CH$_2$Cl$_2$. A solution of octanoyl chloride (1.5 equiv) in CH$_2$Cl$_2$ (0.5 ml) was added dropwise. The mixture was stirred at room temperature for 2 hours. More octanoyl chloride (3.5 equiv) in CH$_2$Cl$_2$ was added dropwise. The mixture was stirred. The solvent was

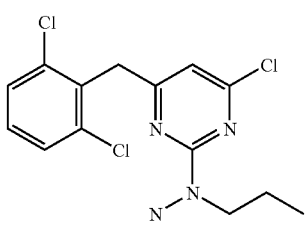

(0.00399 mol) and 4-aminobenzonitrile (0.0012 mol) in 1-methyl-2-pyrrolidinone (3 ml) was stirred for 16 hours at 130° C. under Argon. Then, the reaction mixture was cooled to room temperature and quenched with H$_2$O (200 ml). A precipitate formed, which was stirred for 16 hours, and separated by filtration over Celite. The residue was dissolved in CH$_3$OH/CH$_2$Cl$_2$ (10%, 200 ml), dried over K$_2$CO$_3$, filtered, and evaporated. This resulting material was further purified by flash column chromatography over silica gel (gradient eluent: CH$_2$Cl$_2$/CH$_3$OH from 100/0 to 95/5). The desired fraction was collected and the solvent was evaporated, yielding 0.43 g (21.7%) of 4-[[6-[(2,6-dichlorophenyl)methyl]-2-[[3-(2-oxo-1-pyrrolidinyl)propyl]-amino]-4-pyrimidinyl]amino]benzonitrile (mp. 104–114° C.).

Example 1.B3

HCl/diethyl ether (1N, 2.77 ml) was stirred into a solution of

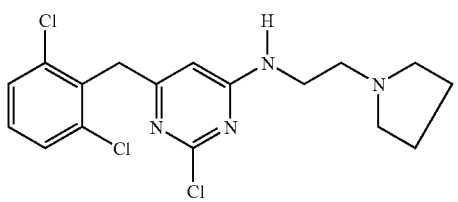

(*1.A4) (0.00277 mol) in 1-methyl-2-pyrrolidinone (4 ml) under N$_2$ atmosphere. The reaction mixture was heated for 5 minutes. Next, 4-aminobenzonitrile (0.0061 mol) was added and the reaction was heated at 100° C. for 16 hours. Then, the reaction mixture was cooled to room temperature and diluted with ethylacetate (10 ml). The organic layer was washed with NaOH (1 N; 2×100 ml), H$_2$O (2×100 ml), brine (50 ml), respectively, dried, filtered and the filtrate was evaporated. The crude material was purified by flash chromatography (eluent: 2.5–7.5% of CH$_3$OH containing 10% NH$_4$OH in CH$_2$Cl$_2$). The desired fractions were collected and the solvent was evaporated. The residue was dried, yielding 0.160 g (12.0%) of 4-[[4-[(2,6-dichloro-phenyl)methyl]-6-[[2-(1 pyrrolidinyl)ethyl]amino]-2-pyrimidinyl]amino]benzonitrile (comp. 14; mp. 80–85° C.).

then evaporated. The residue was treated with a saturated aqueous NaHCO$_3$ solution and the mixture was extracted with CH$_2$Cl$_2$. The separated organic layer was dried, filtered and the solvent was evaporated to give the crude product. The residue was recrystallized from CHCl$_3$ and hexane, yielding 0.443 g (68.6%) of N-[6-[(2,6-dichloro-phenyl)-methyl]-2-[(4-cyano-phenyl)amino]-4-pyrimidinyl]octanamide (mp. 135–137° C.).

Example 1.B8 a) A mixture of intermediate 14 (0.082 mol) and 5.4 N HCl in 2-propanol (0.086 mol) in water (300 ml) was stirred and warmed to 40–45° C. over 30 minutes. 4-Amino-benzonitrile (0.242 mol) was added at 40–45° C. The reaction mixture was stirred and refluxed for 4.5 hours, then cooled to room temperature. The mixture was alkalized by portionwise addition of NaHCO$_3$. This mixture was extracted with ethylacetate. The organic layer was separated, washed with brine, dried, filtered and the solvent was evaporated. This fraction was stirred in ethanol p.a. (100 ml), filtered off, washed with ethanol (50 ml), then dried, yielding 23.1 g (86%) 4-[[4-[(2,4,6-trimethylphenyl)-amino]-2-pyrimidinyl]amino]benzonitrile (comp. 17).

b) A mixture of 4-[(4-chloro-2-pyrimidinyl)amino]benzonitrile (0.021 mol) and HCl in 2-propanol (0.0095 mol) in water (30 ml) was stirred for one hour at 45° C. 4-amino-3,5-dimethyl-benzonitrile (0.025 mol) was added and the reaction mixture was stirred and refluxed overnight. The mixture was cooled to room temperature, then neutralized with NaHCO$_3$. This mixture was extracted with ethylacetate. The separated organic layer was washed with brine, dried, filtered and the solvent evaporated. The residue was crystallized from CH$_3$CN, filtered off and dried. The residue was stirred in boiling CH$_2$Cl$_2$ (20 ml), then filtered off and dried. The residue was crystallized from methyl isobutyl keton, filtered off and dried, yielding 0.3 g of 4-[[2-[(cyanophenyl)amino]-4-pyrimidinyl]amino]-3,5-dimethylbenzonitrile (comp. 25).

Example 1.B9 a) 4-[(4-chloro-2-pyrimidinyl)amino]benzonitrile (0.003 mol), 2,6-dibromo-4-methyl-benzenamine (0.006 mol) and 1 M HCl in diethyl ether (4.5 ml) in 1,4-dioxane (10 ml) were combined in a tube and heated under Ar until all diethyl ether had evaporated. The tube was sealed and heated at 170° C. for 2.5 days. Silica gel was added, and the solvent was evaporated. The residue was purified by flash column chromatography over silica gel (eluent gradient: CH$_2$Cl$_2$:CH$_3$OH:NH$_4$OH 100:0:0 to 99:0.9:0.1). The desired fractions were collected and the solvent was evaporated. The residue was recrystallized from acetonitrile, filtered off and dried, yielding 0.22 g (15.9%) of 4-[[4-[(2,6-dibromo-4-methylphenyl)amino]-2-pyrimidinyl]amino]benzonitrile.

b) 4-[[4-[(4-chloro-5-methyl-2-pyrimidinyl]amino]benzonitrile (0.01541 mol), 4-amino-3,5-dimethyl-benzonitrile (0.00219 mol), 1-methyl-2-pyrrolidinone (4 ml), 1,4-dioxane (15 ml) and diisopropylethylamine (0.0154 mol) were combined in a flask under a stream of argon and heated at 160–230° C. for 16 hours. CH$_2$Cl$_2$ and 1N NaOH were added, and the mixture was stirred 1 hour and filtered to give a brown solid (!). The CH$_2$Cl$_2$ filtrate was separated and was evaporated and purified by flash column chromatography (eluent: 2% CH$_3$OH/CH$_2$Cl$_2$). The desired fractions were combined, evaporated and the residue was stirred in CH$_2$Cl$_2$. The solid precipitate was filtered off, combined with the brown solid (!) and recrystallized from CH$_3$CN. The precipitate was filtered off and dried, yielding 1.57 g (29%) of 4-[[2-[(4-cyanophenyl)amino]-5-methyl-4-pyrimidinyl]amino]-3,5-dimethylbenzonitrile (comp. 52).

c) 2-[(4-cyanophenyl)amino]4-pyrimidinyl trifluoromethanesulfonate (0.0022 mol) and 2,6-dichloro-4-(trifluoromethyl)-benzenamine (0.0044 mol) were combined in 1,4-dioxane (2.5 ml) and heated in a sealed tube under Ar at 170° C. for 40 hours. The reaction mixture was allowed to cool to room temperature. Silica gel was added, and the solvent was evaporated. The residue was purified by flash column chromatography over silica gel (eluent gradient: CH$_2$Cl$_2$:CH$_3$OH:NH$_4$OH 100:0:0 to 97:2.7:0.3). The desired fractions were collected and the solvent was evaporated. The residue was recrystallized from CH$_3$CN, filtered off and dried, yielding 0.086 g (9.2%) of 4-[[4-[[2,6-dichloro-4-(trifluoromethyl)-phenyl]amino]-2-pyrimidinyl]amino]benzonitrile (comp. 23).

Example 1.B10

To a suspension of NaH (0.006 mol) in 1,4-dioxane (30 ml), 2,4,6-trimethyl-phenol (0.006 mol) was added. The mixture was stirred for 15 minutes at room temperature, and a clear solution formed. 4-[(4-chloro-2-pyrimidinyl)amino]benzonitrile (0.004 mol) was added, and the reaction mixture was heated to reflux under Argon for 15 hours. The reaction mixture was allowed to cool to room temperature, 0.5 ml of water was added, followed by 4 g of silica gel, and the solvent was evaporated. The residue was purified by flash column chromatography over silica gel (eluent gradient: CH$_2$Cl$_2$:CH$_3$OH 100:0:0 to 97:3). The pure fractions were collected and the solvent was evaporated, yielding 1.18 g (89.4%) of 4-[[4-(2,4,6-trimethylphenoxy)-2-pyrimidinyl]amino]benzonitrile (comp. 20).

Example 1.B11

4-[[4-[(2,4,6-trimethylphenyl)amino]-2-pyrimidinyl]amino]benzonitrile (0.0015 mol) was stirred in boiling ethanol (8 ml). 6 M HCl in 2-propanol (0.0015 mol) was added and the salt was allowed to crystallize out overnight at room temperature. The precipitate was filtered off, washed with 2-propanol and dried, yielding 0.47 g (86%) of 4-[[4-[(2,4,6-trimethyl-phenyl)amino]-2-pyrimidinyl]amino]benzonitrile hydrochloride (1:1) (comp. 31).

Example 1.B12

A mixture of 4-[[4-[(2,4,6-trimethylphenyl)amino]-2-pyrimidinyl]amino]benzonitrile (0.00303 mol) and NaBO$_3$.4H$_2$O (0.00911 mol) in CH$_3$OH (30 ml) and H$_2$O (10 ml) was stirred and refluxed for 4 days. The reaction mixture was cooled. The precipitate was filtered off and the precipitate (!) was purified by flash column chromatography over silica gel (eluent: CH$_2$Cl$_2$/CH$_3$OH gradient from 100/0 to 95/5). The desired fractions were collected and the solvent was evaporated, yielding 0.586 g (56%) of 4-[[4-[(2,4,6-trimethylphenyl)amino]-2-pyrimidinyl]amino]benzamide (comp. 40). The filtrate (!) was purified by reversed-phase HPLC (eluent gradient: ((0.5% ammoniumacetate in H$_2$O)/CH$_3$CN 90/10)/CH$_3$OH/CH$_3$CN (0 minutes) 75/25/0, (44 minutes) 0/50/50, (57 minutes) 0/0/100, (61.1–70 minutes) 75/25/0). Three desired fraction groups were collected and their solvent was evaporated, yielding 0.18 g of 4-[[4-[(2,4,6-trimethylphenyl)amino]-2-pyrimidinyl]amino]benzamide, N3-oxide (comp. 49) and 0.030 g of 4-[[4-[(2,4,6-trimethylphenyl)amino]-2-pyrimidinyl]-amino]benzamide, N1-oxide.

Example 1.B13 a) A mixture of 4-[[4-chloro-6-[(2,4,6-trimethylphenyl)amino]-1,3,5-triazin-2-yl]-amino]benzonitrile (*A9c) (0.00137 mol) and NH₃ in 1,4-dioxane (0.5 M; 0.00548 mol) was heated in a pressure vessel at 100° C. for 6 days. The solvent was evaporated and the residue was dissolved in CH₂Cl₂, washed with a saturated aqueous NaHCO₃ solution, dried, filtered and the solvent was evaporated. The residue was purified by column chromatography over silica gel (eluent: CH₂Cl₂/CH₃OH 100/0, 99/1 and 98/2). The desired fractions were collected and the solvent was evaporated. The residue was recrystallized from toluene. The precipitate was filtered and dried, yielding 0.29 g (61.4%) of 4-[[4-amino-6-[(2,4,6-trimethylphenyl)amino]-1,3,5-triazin-2-yl]amino]-benzonitrile.

b) As an alternative for the preparation of this compound, a mixture of 4-[[4-chloro-6-[(2,4,6-trimethylphenyl)amino]-1,3,5-triazin-2-yl]amino]benzonitrile (0.0230 mol) in NH₃ in 2-propanol (2.0 M; 60 ml) and NH₃ in 1,4-dioxane (0.5 M; 20 ml) was heated at 95° C. for 21 hours. The solvent was evaporated. The residue was dissolved in ethyl acetate, washed with 1 N NaOH, water and brine, dried, filtered and the filtrate was evaporated. The residue was recrystallized with acetonitrile, yielding 5.25 g (66.1%) of 4-[[4-amino-6-[(2,4,6-trimethylphenyl)amino]-1,3,5-triazin-2-yl]amino]benzonitrile.

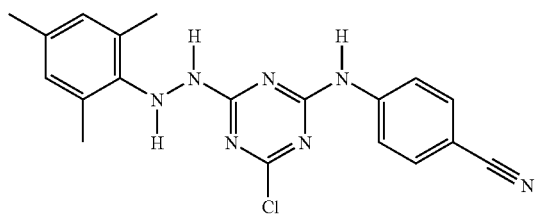

(0.00150 mol) and 0.5 M NH₃ in 1,4-dioxane (0.015 mol) were added into a pressure flask. The reaction mixture was heated to 40° C. After 5 days, the reaction was cooled to room temperature. 2.0 M NH₃ in 2-propanol (0.015 mol) was added, and the reaction was returned to 40° C. The reaction was diluted with diethylether and extracted with cold 1 M NaOH. The aqueous layer was extracted twice more, and the organic phases were combined. The insoluble material was filtered off and washed with diethylether, which dissolved most of the material into the filtrate. The filtrate was combined with the organic phases and this solution was dried, filtered and the solvent evaporated. The residue was purified over silica gel flash chromatography, eluting with 4:1 CH₂Cl₂:diethylether to 100% diethylether. The resulting material was recrystallized in tetrahydrofuran/CH₃CN, filtered off and dried, yielding 0.36 g (67%) of 4-[[4-amino-6-[(2,4,6-trimethylphenyl)azo]-1,3,5-triazin-2-yl]amino]benzonitrile.

Example 1.B14

O-(Trimethylsilyl)-hydroxylamine (0.0282 mol) was added to

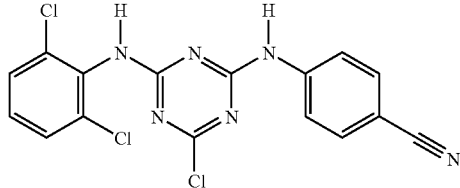

(*1.A10b) (0.00282 mol) in 1,4-dioxane (10 ml). The reaction mixture was stirred at room temperature for 2 days. The solvent was evaporated. The residue was dissolved in ethyl acetate, washed with 1 N HCl, washed with a saturated aqueous NaHCO₃ solution and with brine, dried, filtered and the solvent was evaporated. The residue was purified by column chromatography over silica gel ((I) eluent gradient: CH₂Cl₂/CH₃OH 98/2 to 96/4 and (II) eluent gradient: CH₂Cl₂/CH₃OH 100/0, 99/1 and 98/2) The desired fractions were collected and the solvent was evaporated. The residue was recrystallized from acetonitrile. The precipitate was filtered off and dried, yielding 0.32 g (29.2%) of 4-[[[6-(2,6-dichlorophenylamino)-4-(hydroxylamino)]-1,3,5-triazin-2-yl]amino]benzonitrile.

Example 1.B15

Tetrahydrofuran (10 ml) and 2,5-dimethylphenol (0.00818 mol) were added to NaH (0.00859 mol). The mixture was stirred for 30 minutes at room temperature. Then, a solution of intermediate (17) (0.00818 mol) in tetrahydrofuran (100 ml) was added. The reaction mixture was stirred for 16 hours. Then, the solvent was evaporated and NH₃ in 1,4-dioxane (50 ml) was added. The resulting reaction mixture was stirred for 16 hours. The solvent was evaporated; and, the resulting residue was treated with H₂O/CH₂Cl₂, stirred, and filtered. A precipitate formed in the filtrate and was filtered off, yielding 0.42 g of fraction 1. The resulting filtrate was dried over K₂CO₃ and concentrated. The residue was purified by flash column chromatography (eluent: CH₃OH/CH₂Cl₂ 2.5/97.5). The desired fractions were collected and the solvent was evaporated, yielding 2.89 g of fraction 2. Fractions 1 and 2 were combined and recrystallized from CH₃CN. The precipitate was filtered off and dried, yielding 1.16 g (42.7%) of 4-[[4-amino-6-(2,5-dimethylphenoxy)-1,3,5-triazin-2-yl]amino]benzonitrile.

Example 1.B16

To a reaction vessel under Ar were added resin bound intermediate (17) as prepared in example A 11 (0.00015 mol), a solution of silver triflate (0.075 g) in dimethylsulfoxide (1 ml), 4-bromo-2-chloro-6-methylphenol (0.0027 mol), dimethylsulfoxide (3 ml), and 1.0M sodium bis(trimethylsilyl)amide and disilazane (1,1,1-trimethyl-N-(trimethylsilyl)-silanamine, sodium salt) (3 ml). The reaction mixture was heated at 95° C. for 12 hours. The sample was filtered, and the resin was washed with N,N-dimethylformamide (3×), CH₂Cl₂, N,N-dimethylformamide, CH₃OH, and CH₂Cl₂ (3×). The sample was cleaved twice with 10% trifluoroacetic acid in CH₂Cl₂ (5 ml, then 3 ml). The solvent was evaporated under $N_2$. Purification by reverse phase HPLC yielded 0.0055 g of 4-[[4-amino-6-(4-bromo-2-chloro-6-methylphenoxy)-1,3,5-triazin-2-yl]-amino]benzonitrile.

Example 1.B17

To a flask under Ar were added the resin bound intermediate (17) as prepared in example A 11 (0.00015 mol), $CsCO_3$ (0.975 g), 4-chloro-2,6-dimethylphenol (0.0038 mol), dimethylsulfoxide (2 ml) and 1 ml of a solution of silver triflate (0.075 g) in dimethylsulfoxide (1 ml). Ar was bubbled through the reaction mixture for 1 minute. The flask was heated at 95° C. for 20 hours. The sample was then filtered, and washed with N,N-dimethylformamide (2x), water (3x), N,N-dimethylformamide (2x), $CH_3OH$ (1x), and $CH_2Cl_2$ (3x). The sample was then cleaved with 10% trifluoroacetic acid in $CH_2Cl_2$ (3 ml), yielding 0.0043 g of 4-[[4-amino-6-(4-chloro-2,6-dimethylphenoxy)-1,3,5-triazin-2-yl]amino]benzonitrile.

Example 1.B18

To a flask under Ar were added intermediate (17) (0.00752 mol), N,2,4,6-tetramethyl-benzenamine (0.00752 mol) in 1,4-dioxane (20 ml) and N,N-diisopropylethylamine (0.00752 mol). The reaction mixture was stirred and refluxed for 20 hours and the solvent was evaporated. The residue was transferred into a pressure vessel with 0.5M $NH_3$ in 1,4-dioxane (0.005 mol) and 2.0M $NH_3$ in 2-propanol (0.040 mol) and the mixture was heated at 115° C. for 24 hours. The solvent was evaporated, the residue dissolved in $CH_2Cl_2$, washed with 1N NaOH and water, dried with potassium carbonate, filtered, and the solvent evaporated. The residue was recrystallized two times with acetonitrile, filtered off and dried, yielding 1.0 g (37%) of 4-[[4-amino-6-[methyl-(2,4,6-trimethylphenyl)amino]-1,3,5-triazin-2-yl]amino]benzonitrile (comp. 76).

Example 1.B19

4,6-dichloro —N-(2,6-dibromo-4-methylphenyl)-1,3,5-triazin-2-amine (0.00651 mol), was dissolved in 1,4-dioxane (30 ml). Sequentially, 4-aminobenzonitrile (0.0066 mol) and N,N-diisopropylethylamine (0.0066 mol) were added, and the clear solution was heated to reflux for 4 days. The reaction was allowed to cool to room temperature overnight, and the mixture was diluted with ethyl acetate and treated with cold 1 M NaOH. The layers were separated, and the organic phase was re-extracted with fresh 1 M NaOH. The combined aqueous phases were treated with solid NaOH to maintain pH>10 and backwashed with ethyl acetate (2x). The combined organic phases were dried, filtered and concentrated. The residue was separated and purified by flash column chromatography over silica gel (eluent: $CH_2Cl_2$). The desired fractions were combined, treated with $CH_3CN$, triturated with $CH_3CN$, filtered off and dried, yielding 0.30 g (8.0%) of 4-[[4-amino-6-[(2,6-dibromo-4-methylphenyl)-amino]-1,3,5-triazin-2-yl]amino]benzonitrile.

Example 1.B20

Intermediate (17), 1-(2,3-dihydro-4-hydroxy-7-methyl-1H-inden-5-yl)-ethanone, $Cs_2CO_3$, and 1,4-dioxane were added to a reaction vessel under Ar and heated 100° C. for 48 hours while the sample was slightly vortexed. The sample was cooled, and $NH_3$ in isopropanol was added. The reaction was heated at 100° C. in a sealed tube for 48 hours. The reaction mixture was cooled and water (3 ml) was added to dissolve $Cs_2CO_3$. The sample was filtered and purified by HPLC, yielding 4-[[4-[(5-acetyl-2,3-dihydro-7-methyl-1H-inden-4-yl)oxy]-6-amino-1,3,5-triazin-2-yl]amino]benzonitrile.

1.C. HIV Activity of the Compounds of Formula (I-A)

Example 1.C.1

A rapid, sensitive and automated assay procedure was used for the in vitro evaluation of anti-HIV agents. An HIV-1 transformed T4-cell line, MT-4, which was previously shown (Koyanagi et al., Int. J. Cancer, 36, 445–451, 1985) to be highly susceptible to and permissive for HIV infection, served as the target cell line. Inhibition of the HIV-induced cytopathic effect was used as the end point. The viability of both HIV- and mock-infected cells was assessed spectrophotometrically via the in situ reduction of 3-(4,5-dimethylthiazol-2-yl)-2,5-diphenyltetrazolium bromide (MTT). The 50% cytotoxic concentration ($CC_{50}$ in μM) was defined as the concentration of compound that reduced the absorbance of the mock-infected control sample by 50%. The percent protection achieved by the compound in HIV-infected cells was calculated by the following formula:

$$\frac{(OD_T)_{HIV} - (OD_C)_{HIV}}{(OD_C)_{MOCK} - (OD_C)_{HIV}} \text{ expressed in \%,}$$

whereby $(OD_T)_{HIV}$ is the optical density measured with a given concentration of the test compound in HIV-infected cells; $(OD_C)_{HIV}$ is the optical density measured for the control untreated HIV-infected cells; $(OD_C)_{MOCK}$ is the optical density measured for the control untreated mock-infected cells; all optical density values were determined at 540 nm. The dose achieving 50% protection according to the above formula was defined as the 50% inhibitory concentration ($IC_{50}$ in μM). The ratio of $CC_{50}$ to $IC_{50}$ was defined as the selectivity index (SI). The compounds of formula (I-A) were shown to inhibit HIV-1 effectively. Particular $IC_{50}$, $CC_{50}$ and SI values are listed in Table 1 hereinbelow.

TABLE 1

| Co. No. | $IC_{50}$ (μM) | $CC_{50}$ (μM) | SI | Co. No. | $IC_{50}$ (μM) | $CC_{50}$ (μM) | SI |
|---|---|---|---|---|---|---|---|
| 3 | 0.027 | 49.7 | 1860 | 28 | 0.0063 | 45.8 | 7275 |
| 4 | 0.016 | 37.4 | 2558 | 29 | 0.0007 | 0.5 | 705 |
| 8 | 0.315 | >100 | >317 | 30 | 0.0036 | >100 | >27777 |
| 9 | 0.094 | 56.2 | 598 | 34 | 0.010 | >100 | >9523 |
| 10 | 0.020 | 24.4 | 1192 | 35 | 0.0021 | 1.9 | 911 |
| 11 | 0.037 | 58.6 | 1587 | 36 | 0.0033 | 5.2 | 1580 |
| 14 | 0.005 | 7.8 | 1557 | 37 | 0.0030 | 9.6 | 3188 |
| 12 | 0.003 | 9.0 | 2857 | 38 | 0.0028 | 0.4 | 144 |
| 13 | 0.006 | 53.6 | 8642 | 39 | 0.0031 | 4.8 | 1547 |
| 5 | 0.017 | 50.6 | 2910 | 41 | 0.011 | 8.7 | 771 |
| 6 | 0.035 | 12.2 | 346 | 42 | 0.0011 | >100 | >90909 |
| 1 | 0.001 | 47.9 | 59935 | 43 | 0.0026 | 0.4 | 151 |
| 2 | 0.042 | 43.4 | 1038 | 44 | 0.0008 | 0.4 | 541 |
| 15 | 0.004 | >100 | >27027 | 45 | 0.012 | 9.3 | 753 |
| 16 | 0.058 | 45.2 | 786 | 46 | 0.002 | 0.4 | 208 |
| 7 | 0.518 | 52.0 | 100 | 47 | 0.010 | >100 | >9803 |
| 17 | 0.001 | 2.08 | 2314 | 48 | 0.0031 | 2.2 | 711 |
| 31 | 0.0006 | 1.3 | 2111 | 51 | 0.0027 | 2.1 | 767 |
| 19 | 0.0007 | 0.8 | 1153 | 52 | 0.0007 | 0.4 | 619 |
| 20 | 0.0029 | >100 | >34482 | 18 | 0.0035 | 48.1 | 13743 |
| 21 | 0.0012 | >100 | >83333 | 32 | 0.0022 | 11.1 | 5064 |

TABLE 1-continued

| Co. No. | IC$_{50}$ (µM) | CC$_{50}$ (µM) | SI | Co. No. | IC$_{50}$ (µM) | CC$_{50}$ (µM) | SI |
|---|---|---|---|---|---|---|---|
| 22 | 0.0032 | 8.7 | 2716 | 33 | 0.0006 | 7.7 | 12783 |
| 23 | 0.0085 | 19.9 | 2347 | 50 | 0.0031 | 5.8 | 1885 |
| 24 | 0.001 | 1.4 | 1367 | 40 | 0.075 | 0.8 | 10 |
| 25 | 0.0004 | 4.7 | 11632 | 27 | 0.022 | >100 | 4555 |
| 26 | 0.0006 | 5.8 | 9641 | 53 | 0.0034 | 18.6 | 5476 |
| 54 | 0.003 | 33.8 | 10899 | 69 | 0.002 | 1.7 | 859 |
| 55 | 0.005 | 49.9 | 10187 | 71 | 0.004 | 57.3 | 13349 |
| 56 | 0.001 | 44.0 | 33826 | 73 | 0.003 | 48.0 | 16561 |
| 57 | 0.001 | 6.3 | 4480 | 74 | 0.001 | 48.5 | 80824 |
| 58 | 0.006 | 8.1 | 1372 | 75 | 0.010 | 8.2 | 860 |
| 59 | 0.004 | 40.6 | 11285 | 76 | 0.003 | 51.7 | 16164 |
| 60 | 0.001 | 7.6 | 7614 | 77 | 0.001 | 5.9 | 11848 |
| 66 | 0.001 | 32.1 | 24712 | 78 | 0.003 | 47.0 | 17431 |
| 67 | 0.005 | >10.0 | >1851 | 70 | 0.007 | 30.0 | 4534 |
| 68 | 0.002 | 12.2 | 6102 | 72 | 0.001 | 54.1 | 45129 |

2. Compounds of Formula (I-B)

2.A. Preparation of the Intermediate Compounds

Example 2.A1

Reaction under argon atmosphere. A solution of 2,4,6-trimethylbenzenamine (0.00461 mol) in 1,4-dioxane (5 ml) was added to a solution of 5-bromo-2,4-dichloropyrimidine (0.00439 mol) in 1,4-dioxane (5 ml). N,N-bis(1-methylethyl)ethanamine (0.00548 mol) was added. The reaction mixture was stirred and refluxed for 20 hours. The solvent was evaporated. The residue was dissolved in ethyl acetate, washed with a saturated aqueous sodium bicarbonate solution, water and brine, dried with sodium sulfate, filtered, and the solvent was evaporated. The residue was purified by column chromatography over silica gel (eluent: 1:5, 1:2 and 1:1 CH$_2$Cl$_2$: hexane). Two pure fraction groups were collected and their solvent was evaporated, yielding 0.35 g (24%) of 5-bromo-4-chloro-N-(2,4,6-trimethylphenyl)-2-pyrimidinamine (intern. 1) and 0.93 g (65%) of 5-bromo-2-chloro-N-(2,4,6-trimethylphenyl)-4-pyrimidinamine (interm. 2).

Example 2.A2 a) 4-Hydroxy-5-chloro-2-methylthiopyrimidine (0.0156 mol) and 4-aminobenzonitrile (0.078-mol) were combined as a melt and stirred at 180–200° C. for 6 hours. The reaction mixture was cooled, and triturated sequentially with boiling CH$_2$Cl$_2$ and CH$_3$CN to obtain 95% pure compound, which was dried, yielding 1.27 g (33%) of 4-[(5-chloro-4-hydroxy-2-pyrimidinyl)amino]benzonitrile (interm. 3; mp.>300° C.).

b) POCl$_3$ (10 ml) was added to intermediate (3) (0.0028 mol). The flask was equipped with a condenser and heated to 80° C. for 35 minutes. The material was quenched on ice and allowed and the resulting precipitate was collected and washed with water (50 ml). The sample was dried. A fraction thereof was further purified by column chromatography. The pure fractions were collected and the solvent was evaporated, yielding 4-[(4,5-dichloro-2-pyrimidinyl)amino]benzonitrile (interm. 4).

c) The mixture of intermediate (4) (0.0132 mol) in tetrahydrofuran (75 ml) and CH$_2$Cl$_2$ (10 ml) was stirred for 15 min. HCl in diethyl ether (0.0145 mol) was added slowly, and the mixture was stirred for 5 minutes. The solvent was removed under reduced pressure, yielding 3.98 g of 4-[(4,5-dichloro-2-pyrimidinyl)amino]benzonitrile monohydrochloride (interm. 5).

Example 2.A3 a) 2,4,5,6-tetrachloropyrimidine (0.0134 mol), 1,4-dioxane (30 ml), 2,4,6-trimethyl aniline (0.0134 mol), and N,N-bis (1-methylethyl)ethanamine (0.0136 mol) were added to a flask under argon and stirred at 55° C. for 16 hours. The solvent was evaporated, and the residue was dissolved in CH$_2$Cl$_2$, then purified by column chromatography over silica gel (eluent: CH$_2$Cl$_2$/hexane 1/4, and 1/2). The desired fractions were collected and their solvent was evaporated, yielding 0.15 g 4,5,6-trichloro-N-(2,4,6-trimethylphenyl)-2-pyrimidinamine (interm. 6) and 3.15 g 2,5,6-trichloro-N-(2, 4,6-trimethylphenyl)-4-pyrimidinamine (interm. 7).

b) A mixture of intermediate 7 (0.00474 mol) in NH$_3$, (2.0 M in 2-propanol; 20 ml) was heated in a pressure vessel at 75–80° C. for 40 hours. The temperature was increased to 110–115° C. The solvent was evaporated to produce 1.85 g of residue. The sample was heated with NH$_3$, (0.5 M in 1,4-dioxane; 20 ml) at 125° C. for 18 hours. The solvent was evaporated, yielding 1.7 g of a mixture of two isomers, i.e. 2,5-dichloro-N4-(2,4,6-trimethylphenyl)-4,6-pyrimidinediamine (interm. 8) and 5,6-dichloro-N4-(2,4,6-trimethylphenyl)-2,4-pyrimidinediamine (interm. 9).

Example 2.A4 a) A mixture of 4-[(1,4-dihydro-4-oxo-2-pyrimidinyl) amino]benzonitrile, (0.12 mol) in POCl$_3$ (90 ml) was stirred and refluxed under Argon for 20 minutes. The reaction mixture was slowly poured onto 750 ml ice/water, and the solid was separated by filtration. The solid was suspended in 500 ml water, and the pH of the suspension was adjusted to neutral by adding a 20% NaOH solution. The solid was again separated by filtration, suspended in 200 ml 2-propanone, and 1000 ml CH$_2$Cl$_2$ was added. The mixture was heated until all solid had dissolved. After cooling to room temperature, the aqueous layer was separated, and the organic layer was dried. During removal of the drying agent by filtration, a white solid formed in the filtrate. Further cooling of the filtrate in the freezer, followed by filtration, yielded 21.38 g (77.2%) of 4-[(4-chloro-2-pyrimidinyl) amino]benzonitrile (interm. 10).

b) Intermediate (10) (0.005 mol), 1-bromo-2,5-pyrrolidinedione (0.006 mol) and trichloromethane (10 ml) were combined in a sealed tube and heated at 100° C. overnight. The reaction mixture was allowed to cool to room temperature. Silica gel (2 g) was added, and the solvent was evaporated. The residue was purified by flash column chromatography over silica gel (eluent: CH$_2$Cl$_2$/hexanes 9/1). The pure fractions were collected and the solvent was evaporated, yielding 1.31 g (84.5%) of 4-[(5-bromo-4-chloro-2-pyrimidinyl)amino]benzonitrile (interm. 11).

Example 2.A5

To a flask under Argon was added 4-amino-2,5,6-trichloropyrimidine (0.08564 mol), 4-amino-benzonitrile (0.1071 mol), 1-methyl-2-pyrrolidinone (17 ml) and HCl in diethylether (1M; 85.6 ml). The mixture was placed in an oil bath at 130° C. under a stream of nitrogen until the ether was gone. An additional 10 ml of 1-methyl-2-pyrrolidinone was added. The mixture was heated at 145° C. for 16 hours under argon. 1,4-Dioxane was added. The mixture was refluxed, cooled, then filtered. The filtrate was evaporated. The residue was dissolved in $CH_2Cl_2$, washed with 1 N NaOH, then filtered. The solid was dissolved in 2-propanone, evaporated onto silica gel, and chromatographed using 1–3% 2-propanone in hexane as eluent. The pure fractions were collected and the solvent was evaporated, yielding 1.63 g (6.8%) of 4-[(4-amino-5,6-dichloro-2-pyrimidinyl)amino] benzonitrile (interm. 12).

2.B. Preparation of the Final Compounds of Formula (I-B)

Example 2.B1 a) To a flask under argon containing intermediate (1) (0.00107 mol) was added ether. To this homogeneous solution was added HCl/diethylether (1M; 0.00109 mol). The solvent was evaporated and 1,4-dioxane (35 ml) and 4-aminobenzonitrile (0.00322 mol) were added. The reaction mixture was stirred and refluxed for 4 days. The solvent was evaporated. The residue was dissolved in $CH_2Cl_2$, washed with a saturated sodium bicarbonate solution, dried, filtered and the solvent was evaporated to give 0.79 g of amber oil. The oil was purified by reverse phase HPLC. The desired fractions were collected and the solvent was evaporated, yielding residues 1 and 2. Residue 1 was purified by column chromatography over silica gel (eluent: 0 and 2% $CH_3OH$: $CH_2Cl_2$). The pure fractions were collected and the solvent was evaporated, yielding 0.0079 g (2.0%) of 4-[[5-chloro-2-[(2,4,6-trimethylphenyl)amino]-4-pyrimidinyl]amino] benzonitrile (compound 1).

Residue 2 was purified by column chromatography over silica gel (eluent: 0 and 2% $CH_3OH$:$CH_2Cl_2$). The pure fractions were collected and the solvent was evaporated, yielding 0.0044 g (1.0%) of 4-[[5-bromo-2-[(2,4,6-trimethylphenyl)amino]-4-pyrimidinyl]amino]benzonitrile (compound 2).

b) To a flask containing intermediate 2 (0.00285 mol) was added ether. To this homogeneous solution was added HCl in diethyl ether (1M; 0.00855 mol). The solvent was evaporated and 1,4-dioxane (20 ml) was added. Finally, 4-aminobenzonitrile (0.00291 mol) and 1,4-dioxane (15 ml) were added and the reaction mixture was stirred and refluxed for seven days. The solvent was evaporated, the residue dissolved in $CH_2Cl_2$, washed with 1 M NaOH, and the solvent evaporated. The residue was dissolved in $CH_2Cl_2$ (10 ml) and the precipitate was filtered off and dried, yielding 0.15 g (13%) of 4-[[5-bromo-4-[(2,4,6-trimethylphenyl)amino]-2-pyrimidinyl]amino]benzonitrile (comp. 3).

Example 2.B2 a) A 3:1 mixture of intermediate (8) and intermediate (9) [as prepared in example A3b] and 4-aminobenzonitrile (0.01422 mol) was heated in a pressure vessel at 180° C. for 5 hours. The sample was partitioned between $CH_2Cl_2$ and diluted $NaHCO_3$, dried over $K_2CO_3$, filtered, and evaporated. $CH_3CN$ was stirred in, the resulting precipitate removed by filtration. The filtrate was further purified by reverse phase HPLC. The pure fractions were collected and the solvent was evaporated, yielding 0.17 g of 4-[[4-amino-5-chloro-6-[(2,4,6-trimethylphenyl)amino]-2-pyrimidinyl]amino]benzonitrile trifluoroacetate (1:1) (comp. 4).

Example 2.B3

HCl in diethylether (1M; 0.0045 mol) was added to a suspension of intermediate (4) (0.003 mol) in 1,4-dioxane (5 ml), stirred under argon in a sealable tube. The mixture was warmed to evaporate the diethylether, and 2,4,6-trimethylbenzenamine (0.009 mol) was added. The tube was sealed, and the reaction mixture was heated to 150° C. for 12 hours. The reaction mixture was allowed to cool to room temperature. Sequentially, silica gel (2.2 g) and $CH_3OH$ (50 ml) were added. After evaporating the solvent, the residue was purified by flash chromatography (eluent gradient: $CH_2Cl_2$:$CH_3OH$:$NH_4OH$ 99.5:0.45:0.05 up to 99:0.9:0.1). The pure fractions were collected and the solvent was evaporated. The residue was dried, yielding 0.80 g (73.4%) of 4-[[5-chloro-4-[(2,4,6-trimethylphenyl)amino]-2-pyrimidinyl]amino]benzonitrile (comp. 5).

Example 2.B4

A mixture of intermediate (5) (0.0025 mol) and 2,6-dibromo-4-methylbenzenamine (0.0075 mol) in 1,3-dioxane (5.0 ml) in a sealed tube under argon was heated and stirred at 160° C. for 16 hours. The reaction mixture was concentrated by rotary evaporation onto silica gel (2.0 g). The material was purified by flash chromatography (eluent 1:1 hexanes:$CH_2Cl_2$; neat $CH_2Cl_2$; 0.5%, 1% (10% $NH_4OH$ in $CH_3OH$) in $CH_2Cl_2$) for 90% purity. Recrystallization afforded 0.15 g (12.2%) of 4-[[5-chloro-4-[(2,6-dibromo-4-methylphenyl)amino]-2-pyrimidinyl]amino]benzonitrile (comp. 10; 95% purity).

Example 2.B5

NaH (0.0075 mol; 60% suspension in oil) was added to a suspension of 2,4,6-trimethyl-phenol (0.0075 mol) in 1,4-dioxane (5 ml) in a sealable tube under argon. The mixture was stirred for 15 minutes, and intermediate (4) (0.0025 mol) was added. The tube was sealed, and the reaction mixture was heated to 150° C. for 15 hours. The reaction was allowed to cool to room temperature. After silica gel (2.0 g) was added, the solvent was evaporated. The residue was purified by flash column chromatography over silica gel (eluent gradient: $CH_2Cl_2$: hexanes 9:1 up to 100:0; then $CH_2Cl_2$:$CH_3OH$:$NH_4OH$ 100:0:0 up to 97:2.7:0.3). The pure fractions were collected and the solvent was evaporated. The residue was dried, yielding 0.73 g of (80.2%) 4-[[5-chloro-4-(2,4,6-trimethylphenoxy)-2-pyrimidinyl]amino]benzonitrile (comp. 6).

Example 2.B6

NaH, 60% suspension in oil (0.003 mol) and 1-methyl-2-pyrrolidinone (3 ml) were added to a suspension of 4-hydroxy-3,5-dimethylbenzonitrile (0.003 mol) in 1,4-dioxane (3 ml) in a sealable tube under argon. After the $H_2$ had evolved, intermediate (11) (0.001 mol) was added. The tube was sealed and the reaction mixture was heated to 160° C. for 16 hours. The mixture was cooled to room temperature, transferred to a beaker and diluted with methanol (20 ml). Water (200 ml) was added dropwise. The aqueous mixture was extracted with $CH_2Cl_2$/$CH_3OH$ 90/10 (3×300 ml). The organic layer was separated, dried, filtered and adsorbed onto silica gel (1 g). The solvent was evaporated and the residue was purified by flash column chromatography over silica gel (eluent: $CH_2Cl_2$/$CH_3OH$/$NH_4OH$ from 100/0/0 to 98/1.8/0.2). The desired fractions were collected and the solvent was evaporated. The residue was triturated with hot CH₃CN, filtered off, then dried, yielding 0.20 g (47.6%) of 4-[[5-bromo-4-(4-cyano-2,6-dimethylphenoxy)-2-pyrimidinyl]amino]benzonitrile (comp. 17).

Example 2.B7

To a pressure vessel under argon was added intermediate 12 (0.00286 mol), 4-cyano-2,6-dimethylaniline (0.00571 mol), 1M HCl in diethyl ether (0.00140 mol) and 1,4-dioxane (8 ml). The reaction mixture was heated in an oil bath under a stream of nitrogen until all the solvents had evaporated. 1-methyl-2-pyrrolidinone (3 ml) was added, and the reaction mixture heated at 220–240° C. for 3 hours. Heating was continued at 210–220° C. for 6 hours. The residue was dissolved in 1,4-dioxane, evaporated, partitioned between CH₂Cl₂ and 1 N NaOH, filtered, dried organic layers with potassium carbonate and evaporated. The desired compound was isolated and purified by preparative reverse phase chromatography. The pure fractions were collected and the solvent was evaporated, yielding 0.0165 g (1.1% after lyophilization) of 4-[[4-amino-5-chloro-6-[(4-cyano-2,6-dimethylphenyl)amino]-2-pyrimidinyl]amino]benzonitrile trifluoroacetate (1:1) (comp. 19).

Example 2.B8

A mixture of intermediate (11) (0.0011 mol), 2,6-dimethyl-4-(2-propyl)benzenamine (0.0011 mol), N,N,N',N'-tetramethyl-1,8-naphthalenediamine (0.0022 mol) and 1 M HCl in ether (2.3 ml) (0.0023 mol) in 1,4-dioxane (25 ml) was stirred and heated to 95° C. for 16 hours. Solvent was removed by rotary evaporation and the residue was purified by reverse phase preparatory HPLC. The combined fractions containing the desired material were lyophilized to yield 0.23 g of

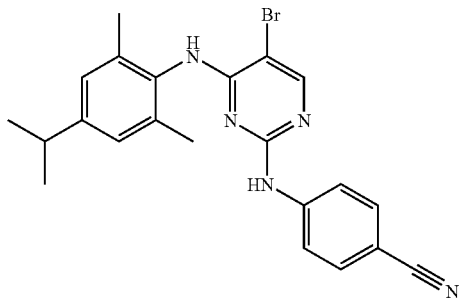

(48%);

mp. 198–201° C. (comp.)

Example 2.B9

N,N-di(methylethyl)ethanamine (0.0024 mol) was added to 4-amino-2,5-dimethyl-3,4-benzonitrile (0.00219 mol) and 4-[[(5-bromo4,6-dichloro)-2-pyrimidinyl]amino]-benzonitrile (0.00218 mol). The reaction vial was sealed and heated to 155–160° C. with stirring for 1.5 days. The sample was cooled to room temperature. The sample was treated with flash column chromatography over silica gel (eluent: CH₂Cl₂). Purification was completed through preparative HPLC to yield 0.05 g of 4-[[5-bromo-4-chloro-6-[(4-cyano-2,6-dimethylphenyl)amino]-2-pyrimidinyl]amino]benzonitrile (5.0%); mp. 259–260° C.

Example 2.B10

Sequentially 2,4,6-trimethylbenzenamine (0.0022 mol) and N,N-di(methylethyl)-ethanamine (0.0024 mol) were added to a solution of and 4-[[(5-bromo-4,6-dichloro)-2-pyrimidinyl]amino]benzonitrile (0.00218 mol) in 1,4-dioxane (10 ml). The tube was sealed and the suspension was heated to 120–130° C. in an oil bath while stirring for 90 hours. The mixture was cooled to room temperature. More N,N-di(methylethyl)-ethanamine (15 ml) was added, and the sample was reheated to 120–130° C. for 64 hours. The reaction was heated at 150° C. for 6 days. The sample was cooled to room temperature. The sample was diluted with ethylacetate and extracted with cold 1M NaOH. The aqueous phase was backwashed with ethylacetate. The combined organic phases were dried and concentrated. Flash column chromatography over silica gel (eluent: CH₂Cl₂). The sample was further purified by preparatory HPLC to yield 0.53 g of 4-[[5-bromo-4-chloro-6-[(2,4,6-trimethylphenyl)amino]-2-pyrimidinyl]amino]-benzonitrile (54.9%); mp. 220–221° C.

Example 2.B11

A mixture of 4-aminobenzonitrile (0.0043 mol) and

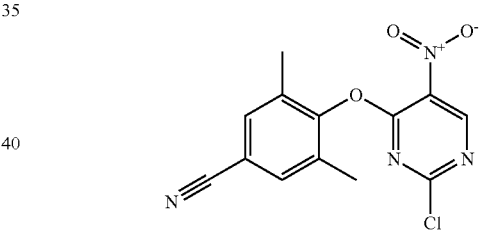

(0.0021 mol) in 1,4-dioxane (30 ml) was stirred at 100° C. for 16 hours. The solvent was removed by rotary evaporation. The solid residue was triturated and the residue was dried in vacuo at 40° C. for 16 hours, yielding 0.452 g of

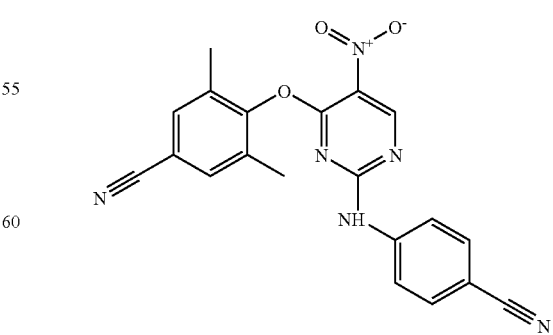

(55%); mp.>300° C.

Example 2.B12

To a pressure vessel was added

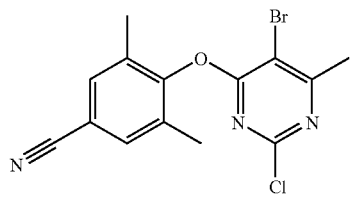

(0.00567 mol), 4-aminobenzonitrile (0.01163 mol) and 1-methyl-2-pyrrolidinone (20 ml). The reaction mixture was heated at 140° C. for 16 hours. The reaction mixture was cooled to room temperature and acetonitrile and water were added. The resulting precipitate was filtered, and the solid recrystallized with acetonitrile to give 1.27 g of 4-[[5-bromo-4-(4-cyano-2,6-dimethylphenoxy)-6-methyl-2-pyrimidinyl]amino]benzonitrile (52); mp. 260–262° C.

Example 2.B13

Intermediate (11) (0.001 mol) and 2,6-dimethyl-4-aminobenzonitrile (0.00473 mol) were combined and heated to 150° C. while stirring for 16 hours. The sample was dissolved in $CH_3OH$ and evaporated onto silica gel (1 g) and eluted with 1:1 hexanes: $CH_2Cl_2$, 4:1 $CH_2Cl_2$:hexanes, and neat $CH_2Cl_2$ (2 L). The desired fractions wer evaporated and the residue was dried in vacuo for 16 hours at 45° C. The thus obtained was transferred to a 4 ml vial in $CH_2Cl_2$ and the solvent was evaporated, yielding 0.120 g of 4-[[5-bromo-6-[(4-cyano-2,6-dimethylphenyl)amino]-2-pyrimidinyl]-amino]benzonitrile (28.6%); mp. 277–280° C.

Example 2.B14

4-[[5-bromo4-(4-cyano-2,6-dimethylphenoxy)-6-chloro-2-pyrimidinyl]amino]-benzonitrile (0.00250 mol) and $NH_3$/1,4-dioxane 0.5M (0.015 mol) were heated in a pressure vessel at 150° C. for 4 days. The sample was allowed to sit at ambient conditions for 2 days. Water was added slowly to the mixture until a precipitate formed. The mixture was stirred for 2 hours and filtered. The solid was recrystallized from $CH_3CN$ to obtain 0.58 g (fraction 1). The filtrate was evaporated (fraction 2). Both fractions were combined and purified by column chromatography, eluting with $CH_2Cl_2$. The resulting residue of the desired fraction was recrystallized from $CH_3CN$ to yield 0.44 g of 4-[[4-amino-5-bromo-6-(4-cyano-2,6-dimethylphenyloxy)-2-pyrimidinyl]amino] benzonitrile (40.5%). The sample was dried at 80° C. for 16 hours at 0.2 mm Hg.

Example 2.B15

4-[[5-bromo-4-(4-cyano-2,6-dimethylphenoxy)-6-chloro-2-pyrimidinyl]amino]-benzonitrile (0.000660 mol), tetrahydrofuran (1 ml), and 1-pyrrolidineethanamine (0.00198 mol) were added to a pressure vessel. The mixture was heated at 75° C. for 16 hours. $CH_2Cl_2$ was added, and the mixture was washed with water, dried, filtered and the filtrate was evaporated. Purification using flash column chromatography eluting with 1:9 methanol:methylene chloride produced a solid which was redissolved in $CH_3CN$. HCl/diethylether 1.0M (0.48 ml) was added, and the mixture was cooled in ice. Filtration yielded 0.19 g of 4-[[5-bromo-4-(4-cyano-2,6-dimethylphenoxy)-6-[(1-pyrrolidinyl)ethylamino]-2-pyrimidinyl]amino]benzonitrile hydrochloride (1:1) (50.6%); mp. 208–210° C.

Example 2.B16

To a pressure vessel was added 4-[[5-bromo-4-(4-cyano-2,6-dimethylphenoxy)-6-chloro-2-pyrimidinyl]amino]benzonitrile (0.00064 mol), tetrahydrofuran (3 ml), O-methylhydroxylamine (0.06 g), tetrahydrofuran and NaOH 1N (0.00067 mol). The reaction mixture was stirred for 3 days at room temperature, then for 1 day at 75° C., for 1 day at 90° C. and for 2 days at 110° C. To O-methylhydroxylamine (0.60 g) was added tetrahydrofuran (4 ml) and NaOH 50% (0.00719 mol). The liquid was decanted into the reaction flask and the reaction mixture was heated at 110° C. for 3 days. The solvent was evaporated. The residue was dissolved in $CH_2Cl_2$, washed with a saturated $NaHCO_3$ solution and water, dried ($Na_2SO_4$), filtered and the solvent was evaporated. The residue was purified by column chromatography over silica gel (eluent: $CH_2Cl_2/CH_3OH$ 98/2). The pure fractions were collected and the solvent was evaporated. The residue was crystallized from $CH_3CN$, filtered off and dried, yielding 0.15 g of 4-[[S-bromo-4-(4-cyano-2,6-dimethylphenoxy)-6-(methoxyamino)-2-pyrimidinyl]amino]benzonitrile (51%); mp. 185–186° C. The sample was dried (0.2 mm Hg, 80° C., 16 hours).

Example 2.B17 a) n-Butyllithium (2.01, 0.005 mol) was added to a 0° C. stirred solution of 1-(methyl-ethyl)-2-propanamine (0.70 ml, 0.005 mol) and tetrahydrofuran (300 ml). After stirring cold for 30 min, compound (17) (0.005 mol) was added. The resulting mixture was stirred cold for 30 min at which point 1,1-dimethylethyl bromoacetate (1.5 ml, 10 mmol) was added and the temperature was allowed to rise to room temperature and the reaction was stirred for three. In a separate flask n-butyllithium (2.0 ml, 5 mmol) was added to a stirred 0° C. solution of 1-(methylethyl)-2-propanamine (0.70 ml, 5 mmol) in tetrahydrofuran (50 ml) and allowed to react for 30 min at which time it was transferred to the room temperature reaction. This procedure was repeated. Quenched with 0.5 ml $H_2O$, the sample was concentrated by rotary evaporation onto silica gel, and purified by flash chromatography (eluting with 0, 10, 20% ethylacetate in hexanes) to give a white solid of

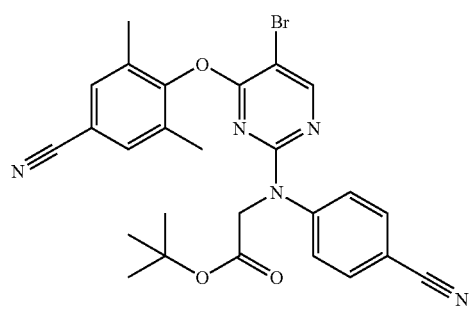

mp. 195–197° C.

b) A suspension of compound (17) in 40 ml of N,N-methylformamide was treated with 0.24 g of NaH. The effervescent mixture was stirred for 90. A solution of 1,4-dichloro-1,4-butanedione in 10 ml N,N-dimethylformamide was prepared and cooled in an ice bath. The mixture prepared from compound (17) was transferred to the cold solution of 1(methylethyl)-1-propanamine and was warmed to room temperature with stirring for 42 hours. Another 0.24 g of NaH was added, the reaction was stirred for 3 days, and diluted with ether and poured into ice. Precipitation was removed by filtration. The 2 phase filtrate was separated and the acidic aqueous fraction was extracted twice more with ether. The combined ether fractions were washed with small volumes of distilled water and dried. The solvent was evaporated and the residue was subjected to silica gel column chromatography. Reverse phase prep HPLC with immediate cooling for lyophilization of the appropriate fractions provided 0.07 g of

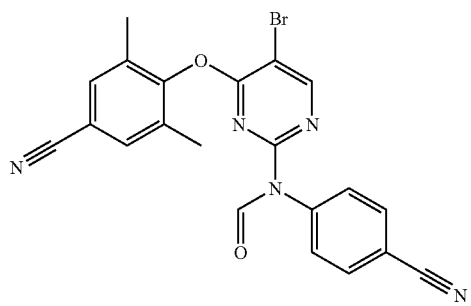

(7.8%); mp. 232–233° C.

c) To a flask under argon was added NaH 60% and tetrahydrofuran. The reaction was stirred at room temperature for 10 min and compound (17) added. After stirring for 1 hr ethyl carbonochloridate was added. The reaction mixture was stirred at room temperature for another 16 hrs and the solvent evaporated. The residue was partially dissolved in dimethylsulfoxide and filtered. The filtrate was purified by reverse phase Chromatography and lyophilized to give 0.47 g (18%) of

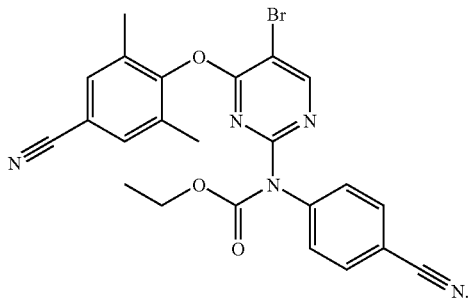

d) A mixture of 4-[[5-amino-4-(4-cyano-2,6-dimethylphenoxy)-2-pyrimidinyl]-amino]benzonitrile (0.00147 mol) in ethanoic acid anhydride (10 ml) and 2-propanone (10 ml) was stirred at room temperature for 16 hours. The mixture was then heated to 55° C., and more ethanoic acid anhydride (3 ml) was added. The mixture was removed from heat after 18 hours and stirred for 6 days at room temperature. The sample was concentrated by rotary evaporation to a solid. Purification by column chromatography (eluting with 0, 0.5, 1, 1.5, 2% (10% NH$_4$OH in CH$_3$OH) in methylene chloride) yielded

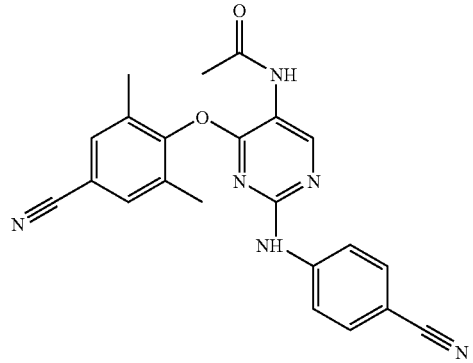

; mp. 290–295° C. The solid was dried in vacuo for 16 hours at 60° C.

Example 2.B18

A mixture of 4-[[4-(4-cyano-2,6-dimethylphenoxy)-5-nitro-2-pyrimidinyl]amino]-benzonitrile (0.0005 mol) in tetrahydrofuran (20 ml) was hydrogenated overnight with Pd/C 10% (0.100 g) as a catalyst. After uptake of H$_2$ (3 equiv; 0.0015 mol), the catalyst was filtered off and the filtrate was concentrated by rotary evaporation and dried in vacuo over 16 hours at 40° C., yielding 0.15 g of 4-[[5-amino-4-(4-cyano-2,6-dimethylphenoxy)-2-pyrimidinyl]amino]benzonitrile (84%); mp.>300° C.

Example 2.B19

4-[[4-[(2,4,6-trimethylphenyl)amino]-5-nitro-2-pyrimidinyl]amino]benzonitrile (0.001 mol), Pd/C 10% (0.025 g), ethanol (20 ml), and hydrazine (0.030 mol) were combined to form a slurry and stirred at room temperature for 16 hours. The solvent was removed by rotary evaporation. The residue was taken up in tetrahydrofuran (20 ml) and methanol (1 ml). A second portion of hydrazine (0.5 g) was added, and the reaction was stirred for 16 hours at room temperature. A third portion of hydrazine (0.5 ml) was added and the reaction was stirred for an additional 16 hours at room temperature. The sample was concentrated by rotary evaporation onto silica gel (1 g) and purified by flash chromatography (eluent: 0.5, 1,2% 10% (NH$_4$OH in CH$_3$OH) in CH$_2$Cl$_2$). The desired fractions were purified by preparatory HPLC to yield 0.24 g of 4-[[5-amino-4-[(2,4,6-trimethylphenyl)amino]-2-pyrimidinyl]amino]benzonitrile (70%); mp. 224–225° C.

Example 2.B20

Compound (3) (0.001 mol), trimethyl silanecarbonitrile (0.0012 mol), Pd(PPh$_3$)$_2$Cl$_2$ (0.020 g), CuI (0.010 g) and CF$_3$COOH/H$_2$O (3 ml) were combined in a sealed tube and heated to 110° C. for 10 hours. Second portions of the catalysts Pd(PPh$_3$)$_2$Cl$_2$ (0.020 g) and CuI (0.010 g), and CF$_3$COOH/H$_2$O (3 ml) were added and the reaction mixture was stirred for 10 hours at 110° C. The material was concentrated by rotary evaporation. The residue was purified by preparative reversed-phase HPLC. The desired fractions were concentrated and purified by reversed-phase preparative HPLC and dried with a stream of N$_2$, then in vacuo at 40° C. for 16 hours. Yield: 0.011 g of 4-[[5-ethynyl-4-[(2,4,6-trimethylphenyl)amino]-2-pyrimidinyl]amino]benzonitrile; mp. 165–175° C.

Example 2.B21

Compound (3) (0.000906 mol), tributylphenyl stannane (0.000906 mol), Pd(PPh$_3$)$_4$ (0.002718 mol), and 1,4-dioxane (3 ml) were combined under N$_2$ in a sealed tube and heated to 110° C. for 16 hours. The reaction mixture was cooled and concentrated by rotary evaporation. The sample was purified by Preparatory Reverse Phase HPLC, then dried under Ar stream. Drying in vacuo yielded 0.0845 g of or 4-[[5-phenyl-4-[(2,4,6-trimethylphenyl)amino]-2-pyrimidinyl]amino]benzonitrile; mp. 209–214° C.

Example 2.B22

Compound (3) (0.001 mol), tetraethenyl stannane (0.22 ml), 1,4-dioxane (2 ml) and Pd(PPh$_3$)$_4$ (0.112 g) were combined in a sealed tube under Ar. The mixture was stirred and heated to 100° C. for 16 hours. More tetraethenyl stannane and Pd(PPh$_3$)$_4$ were added. The reaction was placed under Ar, stirred and heated. The reaction was concentrated by rotary evaporation and purified on preparative HPLC. The material was dried with a N$_2$ stream, and dried under vacuum for 4 hours at 60° C. to obtain 0.422 g of 4-[[5-ethenyl-4-[(2,4,6-trimethylphenyl)amino]-2-pyrimidinyl]amino]-benzonitrile; mp. 237–242° C.

Example 2.B23

Compound (3) (0.001225 mol), CuCN (0.001470 mol) and N,N-dimethylformamide (2 ml) were combined in a sealed tube under Argon, then stirred and heated to 160° C. for 16 hours. The residue was purified by column chromatography (eluent: CH$_2$Cl$_2$/hexane 1/1, then pure CH$_2$Cl$_2$). The desired fractions were collected and the solvent was evaporated. The residue was triturated under CH$_2$Cl$_2$ at room temperature. The solid was dried (vacuum, 40° C., 24 hours, yielding 0.0864 g of

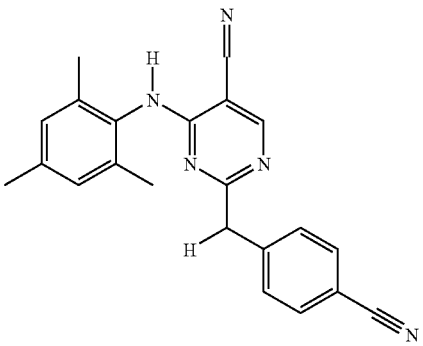

(24%); mp. 254–259° C.

Tables 2, 3, 4 and 5 list compounds of formula (I-B) which were made analogous to one of the above examples.

TABLE 2

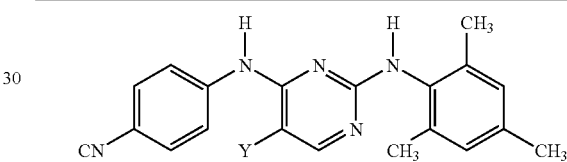

| Comp. No. | Ex. No. | Y | Physical data |
|---|---|---|---|
| 1 | 2.B1a | Cl | — |
| 2 | 2.B1a | Br | mp. 227–228° C. |
| 22 | 2.B11 | NO$_2$ | mp. 224–226° C. |

TABLE 3

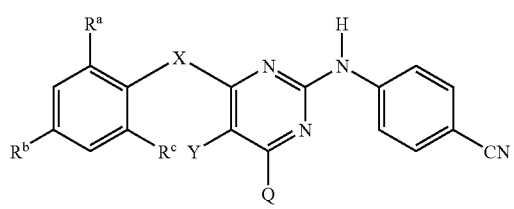

| Comp. No. | Ex. No. | R$^a$ | R$^b$ | R$^c$ | X | Y | Q | |
|---|---|---|---|---|---|---|---|---|
| 3 | 2.B1b | CH$_3$ | CH$_3$ | CH$_3$ | NH | Br | H | mp. 227–228° C. |
| 4 | 2.B2 | CH$_3$ | CH$_3$ | CH$_3$ | NH | Cl | NH$_2$ | mp. 241–242° C. |
| 5 | 2.B3 | CH$_3$ | CH$_3$ | CH$_3$ | NH | Cl | H | mp. 224–226° C. |
| 6 | 2.B5 | CH$_3$ | CH$_3$ | CH$_3$ | O | Cl | H | mp. 218–219° C. |
| 7 | 2.B5 | CH$_3$ | CH$_3$ | CH$_3$ | S | Cl | H | mp. 264–266° C. |
| 8 | 2.B5 | CH$_3$ | Br | CH$_3$ | O | Cl | H | mp. 237–238° C. |
| 9 | 2.B3 | CH$_3$ | Br | CH$_3$ | NH | Cl | H | mp. 217–219° C. |
| 10 | 2.B4 | Br | CH$_3$ | Br | NH | Cl | H | mp. 262–263° C. |
| 11 | 2.B4 | Br | Br | F | NH | Cl | H | mp. 200–202° C. |
| 12 | 2.B4 | CH$_3$ | C(CH$_3$)$_3$ | CH$_3$ | NH | Cl | H | mp. 214–215° C. |

TABLE 3-continued

| Comp. No. | Ex. No. | $R^a$ | $R^b$ | $R^c$ | X | Y | Q | |
|---|---|---|---|---|---|---|---|---|
| 13 | 2.B4 | $CH_3$ | CN | $CH_3$ | NH | Cl | H | mp. 281–283° C. |
| 14 | 2.B4 | Cl | Cl | $CH_3$ | NH | Cl | H | mp. 243–245° C. |
| 15 | 2.B5 | Cl | Br | $CH_3$ | O | Cl | H | mp. 244–247° C. |
| 16 | 2.B5 | $CH_3$ | Cl | $CH_3$ | O | Cl | H | mp. 232–235° C. |
| 17 | 2.B6 | $CH_3$ | CN | $CH_3$ | O | Br | H | mp. 288–289° C. |
| 18 | 2.B5 | $CH_3$ | CN | $CH_3$ | O | Cl | H | mp. 283–284° C. |
| 19 | 2.B7 | $CH_3$ | CN | $CH_3$ | NH | Cl | $NH_2$ | mp. 266–268° C. |
| 20 | 2.B3 | Cl | Cl | $CH_3$ | NH | Br | H | mp. 253–254° C. |
| 21 | 2.B3 | $CH_3$ | Br | $CH_3$ | NH | Br | H | mp. 243–245° C. |
| 23 | 2.B23 | $CH_3$ | CN | $CH_3$ | NH | CN | H | mp. 275–290° C. |
| 24 | 2.B23 | $CH_3$ | Br | $CH_3$ | NH | CN | H | mp. 291–299° C. |
| 25 | 2.B14 | $CH_3$ | CN | $CH_3$ | O | Br | $NH-CH_3$ | mp. 248–250° C. |
| 26 | 2.B14 | $CH_3$ | CN | $CH_3$ | O | Br | $NH_2$ | mp. 255–256° C. |
| 27 | 2.B14 | $CH_3$ | $CH_3$ | $CH_3$ | O | Br | $NH_2$ | — |
| 28 | 2.B14 | $CH_3$ | $CH_3$ | $CH_3$ | O | Br | $NH-CH_3$ | mp. 213–214° C. |
| 29 | 2.B14 | $CH_3$ | CN | $CH_3$ | O | Br | $NH-C_2H_5$ | mp. 263–264° C. |
| 30 | 2.B14 | $CH_3$ | CN | $CH_3$ | O | Cl | $NH_2$ | mp. 272–274° C. |
| 31 | 2.B14 | $CH_3$ | $CH_3$ | $CH_3$ | O | Cl | $NH_2$ | mp. 199–202° C. |
| 32 | 2.B11 | $CH_3$ | $CH_3$ | $CH_3$ | NH | $NO_2$ | H | mp. >300° C. |
| 33 | 2.B5 | $CH_3$ | $CH_3$ | $CH_3$ | O | Br | H | mp. 207–215° C. |
| 34 | 2.B5 | $CH_3$ | $CH_3$ | $CH_3$ | O | Cl | Cl | mp. 225–226° C. |
| 35 | 2.B5 | $CH_3$ | CN | $CH_3$ | O | Cl | Cl | mp. 273–276° C. |
| 36 | 2.B6 | $CH_3$ | CN | $CH_3$ | O | Cl | Br | mp. 281–282° C. |
| 37 | 2.B5 | $CH_3$ | $CH_3$ | $CH_3$ | O | Cl | Br | mp. 214–215° C. |

TABLE 4

| Comp. No. | Ex. No. | $R^a$ | $R^b$ | $R^c$ | X | Y | Q | Z | |
|---|---|---|---|---|---|---|---|---|---|
| 38 | 2.B17C | $CH_3$ | CN | $CH_3$ | O | Br | H | $C(=O)-CH_3$ | mp. 194–196° C. |

TABLE 5

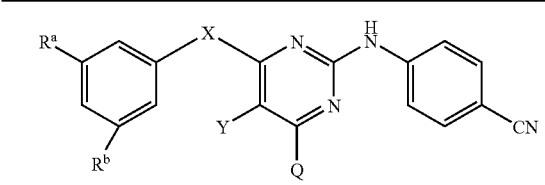

| Comp. No. | Ex. No. | $R^a$ | $R^b$ | X | Y | Q | |
|---|---|---|---|---|---|---|---|
| 39 | 2.B5 | Cl | Cl | S | Br | H | mp. 198–200° C. |

2.C. Pharmacological Example

Example 2.C.1

The same test as described above for the compounds of formula (I-A) (example 1.C.1) was used for the in vitro evaluation of the anti-HIV agents of formula (I-B). The compounds of formula (I-B) were shown to inhibit HIV-1 effectively. Particular $IC_{50}$, $CC_{50}$ and SI values of compounds of formula (I-B) are listed in Table 6 hereinbelow.

TABLE 6

| Co. No. | $IC_{50}$ (µM) | $CC_{50}$ (µM) | SI |
|---|---|---|---|
| 2 | 0.030 | 82.6 | 2730 |
| 3 | 0.006 | 4.4 | 738 |

TABLE 6-continued

| Co. No. | IC$_{50}$ (µM) | CC$_{50}$ (µM) | SI |
|---|---|---|---|
| 1 | 0.004 | 10.9 | 2787 |
| 4 | 0.002 | 10.0 | 5555 |
| 5 | 0.002 | 0.4 | 178 |
| 6 | 0.009 | >100 | >11049 |
| 7 | 0.084 | >100 | >1182 |
| 8 | 0.012 | >100 | >8298 |
| 9 | 0.003 | 1.2 | 376 |
| 10 | 0.005 | 0.4 | 92 |
| 11 | 0.002 | 0.4 | 183 |
| 12 | 0.020 | 48.5 | 2393 |
| 13 | 0.0005 | 0.4 | 860 |
| 14 | 0.002 | 0.4 | 191 |
| 15 | 0.010 | >100 | >9661 |
| 16 | 0.010 | >100 | >10416 |
| 17 | 0.002 | >10 | >6451 |
| 18 | 0.001 | >10 | >7142 |

3. Compounds of Formula (I-C)

Hereinafter, the term 'RT' means room temperature, 'THF' means tetrahydrofuran and 'EtOAc' means ethyl acetate.

3.A. Preparation of the Intermediates

Example 3.A1

Starting material 2,4-dichloro-1,3,5-triazine was prepared in 34.8% yield by the method of Synthesis 1981, 907. A solution of 2,4-dichloro-1,3,5-triazine (0.0238 mol) in 1,4-dioxane (120 ml) was prepared with vigorous stirring. 4-Aminobenzonitrile (0.0240 mol) was added in one portion, resulting in a suspension. N,N-bis(1-methylethyl) ethanamine (0.0241 mol) was added. The reaction mixture was stirred at RT for 48 hours. The reaction was concentrated in vacuo to produce a viscous orange syrup which was dissolved with EtOAc and treated with cold 1 M NaOH. The combined aqueous phases were back extracted with EtOAc. The combined organic extracts were dried over MgSO$_4$, filtered and the filtrate was evaporated to give 5.27 g of yellow powder that was subjected to flash chromatography on silica gel (eluent: 100% CH$_2$Cl$_2$ to 90:10 CH$_2$Cl$_2$/Et$_2$O). The pure fractions were collected and the solvent was evaporated to give 3.87 g of off white solid that was recrystallized from CH$_3$CN, filtered off and dried, yielding 3.57 g (64.8%) of 4-[(4-chloro-1,3,5-triazin-2-yl)amino] benzonitrile (Intermediate 1).

3.B. Preparation of the Final Compounds

Example 3.B.1

Intermediate (1) (0.00160 mol) was partially dissolved by stirring in 1,4-dioxane (10 ml). Sequentially, 2,4,6-trimethylbenzenamine (0.00164 mol) and N,N-bis-(1-methylethyl)ethanamine (0.00164 mol) were added, and the resulting suspension was heated to reflux with stirring. The mixture cleared at 40–50° C. After 4.5 days at reflux, the reaction was cooled to RT, diluted with Et$_2$O, and treated with cold 1 M NaOH. EtOAc was added to dissolve all of the material between the 2 layers. The organic phase was separated and extracted with cold 1 M NaOH. The combined aqueous fractions were washed with EtOAc, adding solid NaOH to adjust the pH to >10. The combined organic phases were dried (MgSO$_4$), filtered and the solvent was evaporated in vacuo to give 0.60 g brown waxy solid. This fraction was purified by flash column chromatography over silica gel (eluent: 100% CH$_2$Cl$_2$ to 80:20 CH$_2$Cl$_2$/Et$_2$O). The pure fractions were collected and the solvent was evaporated to give 0.40 g of white waxy solid that was recrystallized from CH$_3$CN. The precipitate was filtered off and dried, yielding 0.24 g (45.4%) of 4-[[4-[(2,4,6-trimethylphenyl)amino]-1,3,5-triazin-2-yl]amino]benzonitrile (compound 1).

Example 3.B.2

NaH (0.0025 mol) and THF (5 ml) were added to a flask equipped with an addition funnel. A solution of 2,4,6-trimethylphenol (0.00206 mol) in THF (15 ml) was added dropwise with stirring over 15 minutes. The reaction mixture was stirred at room temperature for 45 minutes. Intermediate (1) (0.00203 mol) was added in one portion. The reaction mixture was stirred for 4 days. The reaction was quenched by pouring over ice (75 ml). Upon melting, a minimal amount of precipitate formed. The mixture was treated with Et$_2$O and EtOAc and the fractions were separated. The pH of the aqueous fraction was adjusted to >10 by treatment with solid NaOH and extracted with EtOAc. The combined organic phases were treated with cold 1 M NaOH. The organic phases were dried over MgSO$_4$. Concentration in vacuo afforded 0.65 g white powder. This fraction was recrystallized from CH$_3$CN, filtered off and dried, yielding 0.50 g (74.4%) of 4-[[4-(2,4,6-trimethylphenoxy)-1,3,5-triazin-2-yl]amino]benzonitrile (compound 2).

Example 3.B.3

Intermediate (1) (0.00203 mol) and 1,4-dioxane (15 ml) were added to a flask and stirred. Sequentially, 2,4,6-trimethylbenzenethiol (0.00204 mol) and N,N-bis(1-methylethyl)ethanamine (0.00207 mol) were added and stirred at ambient temperature. After stirring for one hour, THF (10 ml) was added. The reaction mixture was heated to reflux for 64 hours and cooled to RT. The reaction mixture was diluted with EtOAc and treated with cold 1 M NaOH. The aqueous phase was extracted with EtOAc while maintaining the pH>10 with the addition of solid NaOH. The combined organic phases were dried over MgSO$_4$ and concentrated to afford 0.75 g yellow powder. The residue was crystallized from CH$_3$CN, filtered off and dried, yielding 0.64 g (90.7%) of 4-[[4-[(2,4,6-trimethylphenyl)thio]-1,3,5-triazin-2-yl]amino]benzonitrile (compound 3).

Table 7 lists the compounds of formula (I-C) which were prepared according to one of the above examples.

TABLE 7

| Comp No. | Ex. No. | X | R$^a$ | R$^b$ | R$^c$ | Physical Data |
|---|---|---|---|---|---|---|
| 1 | 3.B1 | —NH— | CH$_3$ | CH$_3$ | CH$_3$ | mp. 248–249° C. |
| 2 | 3.B2 | —O— | CH$_3$ | CH$_3$ | CH$_3$ | mp. 220–221° C. |
| 3 | 3.B2 | —O— | CH$_3$ | Br | Cl | mp. 221–222° C. |
| 4 | 3.B3 | —S | CH$_3$ | CH$_3$ | CH$_3$ | mp. 256–257° C. |
| 5 | 3.B2 | —O— | Br | CH$_3$ | Br | mp. 255–257° C. |

TABLE 7-continued

[structure diagram]

| Comp No. | Ex. No. | X | $R^a$ | $R^b$ | $R^c$ | Physical Data |
|---|---|---|---|---|---|---|
| 6 | 3.B1 | —NH— | Br | $CH_3$ | Br | mp. 285–286° C. |
| 7 | 3.B1 | —NH— | $CH_3$ | Br | $CH_3$ | mp. 248–249° C. |

3.C. Pharmacological Example

Example 3.C.1

The same test as described above for the compounds of formula (I-A) (example 1.C.1) was used for the in vitro evaluation of the anti-HIV agents of formula (I-C). The compounds of formula (I-C) were shown to inhibit HIV-1 effectively. Particular $IC_{50}$, $CC_{50}$ and SI values of compounds of formula (I-C) are listed in Table 8 hereinbelow.

TABLE 8

| Co. No. | $IC_{50}$ (µM) | $CC_{50}$ (µM) | SI |
|---|---|---|---|
| 1 | 0.0004 | 9.1 | 22722 |
| 2 | 0.0006 | >100 | >166666 |
| 3 | 0.0011 | 56.2 | 53536 |
| 4 | 0.0022 | >100 | >46511 |
| 5 | 0.0016 | 10.1 | 6452 |
| 6 | 0.0005 | 1.0 | 1901 |
| 7 | 0.0007 | 27.8 | 39722 |

4. Preparation of the Particles of the Present Invention 8 g of compound 17 of formula (I-A) and 12 g hydroxypropyl methylcellulose 2910 5 mpa·s (HPMC 2910 5 mPa·s) were mixed until the mixture was homogenous. The mixture was fed into a Gimac single screw extruder L/D 24:1 having the following operating parameters: screw rate was 30 revolutions per minute, the temperature ranged from 70° C. to 235° C. Yield was 17 g (85%). The melt extrudate was milled and fractions with particle size below 150 µm (condition I in point 6) and between 500 and 850 µm (condition II in point 6) were collected.

5. Thermal Stability of the Antiviral Compound in the Melt Extrudate

The thermal stability of compound 17 of formula (I-A) after melt extrusion was determined by HPLC (high performance liquid chromatography). No degradation of the antiviral compound could be detected, which confirms the thermal stability of said compound after melt extrusion.

6. Dissolution Study

In-vitro dissolution studies were performed on the melt extrudate fractions described under point 4. 375 mg of each fraction was directly added to the dissolution medium. The fraction with particle size between 500 and 850 µm was also filled in a gelatin capsule nr. 0 EL, which was then added to the dissolution medium (III). The dissolution medium was 900 ml of 0.1 N HCl at 37° C. in Apparatus 2 (USP 23, <711> Dissolution, pp. 1791–1793) (paddle, 100 rpm). The concentration of the active ingredient compound 17 of formula (I-A) dissolved in the test medium was determined by removing a 3 ml sample at the indicated time, filtering the sample over a millex-LCR filter, measuring its absorbance at 286 nm and calculating the concentration therefrom.

The following results were obtained:

| Time (min) | Percentage dissolved active ingredient | | |
|---|---|---|---|
| | I | II | III |
| 0 | 0.00 | 0.00 | 0.00 |
| 5 | 64.32 | 33.96 | 12.90 |
| 15 | 76.44 | 69.18 | 52.02 |
| 30 | 82.74 | 79.50 | 79.08 |
| 45 | 91.50 | 84.84 | 88.98 |
| 60 | 98.34 | 92.40 | 92.28 |

I: compound 17 of formula (I-A):HPMC 2910 5 mPa · s (1:1.5 (w/w)); fraction with particle size below 150 µm
II: compound 17 of formula (I-A):HPMC 2910 5 mPa · s (1:1.5 (w/w)); fraction with particle size between 500 and 850 µm
III: compound 17 of formula (I-A):HPMC 2910 5 mPa · s (1:1.5 (w/w)); fraction with particle size between 500 and 850 µm filled in a gelatin capsule nr. 0 EL The in vitro dissolution study from the melt extrudate fractions and the fraction filled in a gelatine capsule shows that the drug release reached at least 85% after 60 minutes.

The invention claimed is:
1. A particle consisting of a solid dispersion, comprising:
(a) a compound of formula

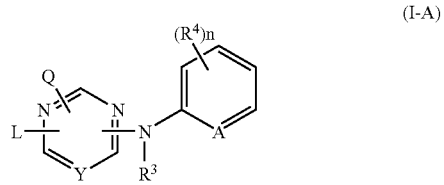

(I-A)

a N-oxide, a pharmaceutically acceptable addition salt or a stereochemically isomeric form thereof,
wherein
Y is $CR^5$ or N;
A is CH, $CR^4$ or N;
n is 0, 1, 2, 3 or 4;
Q is —$NR^1R^2$ or when Y is $CR^5$ then Q may also be hydrogen;
$R^1$ and $R^2$ are each independently selected from hydrogen, hydroxy, $C_{1-12}$alkyl, $C_{1-12}$alkyloxy, $C_{1-12}$alkylcarbonyl, $C_{1-12}$alkyloxycarbonyl, aryl, amino, mono- or di($C_{1-12}$alkyl)amino, mono- or di($C_{1-12}$alkyl)aminocarbonyl wherein each of the aforementioned $C_{1-12}$alkyl groups may optionally and each individually be substituted with one or two substituents each independently selected from hydroxy, $C_{1-6}$alkyloxy, hydroxy$C_{1-6}$alkyloxy, carboxyl, $C_{1-6}$alkyloxycarbonyl, cyano, amino, imino, aminocarbonyl, aminocarbonylamino, mono- or di($C_{1-6}$alkyl)amino, aryl and Het; or $R^1$ and $R^2$ taken together may form pyrrolidinyl, piperidinyl, morpholinyl, azido or mono- or di($C_{1-12}$alkyl)amino$C_{1-4}$alkylidene;
Het is an aliphatic or aromatic heterocyclic radical, wherein said aliphatic heterocyclic radical is optionally substituted with an oxo group and wherein said aromatic heterocyclic radical is optionally substituted with hydroxy;

$R^3$ is hydrogen, aryl, $C_{1-6}$alkylcarbonyl, $C_{1-6}$alkyl, $C_{1-6}$alkyloxycarbonyl, $C_{1-6}$alkyl substituted with $C_{1-6}$alkyloxycarbonyl;

each $R^4$ independently is hydroxy, halo, $C_{1-6}$alkyl, $C_{1-6}$alkyloxy, cyano, aminocarbonyl, nitro, amino, trihalomethyl, trihalomethyloxy, or when Y is $CR^5$ then $R^4$ may also represent $C_{1-6}$alkyl substituted with cyano or aminocarbonyl;

$R^5$ is hydrogen or $C_{1-4}$alkyl;

L is —$X^1$—$R^6$ or —$X^2$-Alk-$R^7$, wherein
$R^6$ and $R^7$ each independently are phenyl or phenyl substituted with one, two, three, four or five substituents each independently selected from halo, hydroxy, $C_{1-6}$alkyl, $C_{1-6}$alkyloxy, $C_{1-6}$ alkylcarbonyl, $C_{1-6}$alkyloxycarbonyl, formyl, cyano, nitro, amino, and trifluoromethyl; or when Y is $CR^5$ then $R^6$ and $R^7$ may also be selected from phenyl substituted with one, two, three, four or five substituents each independently selected from aminocarbonyl, trihalomethyloxy and trihalomethyl; or when Y is N then $R^6$ and $R^7$ may also be selected from indanyl or indolyl, each of said indanyl or indolyl may be substituted with one, two, three, four or five substituents each independently selected from halo, hydroxy, $C_{1-6}$alkyl, $C_{1-6}$alkyloxy, $C_{1-6}$alkylcarbonyl, $C_{1-6}$alkyloxycarbonyl, formyl, cyano, nitro, amino, and trifluoromethyl;

$X^1$ and $X^2$ are each independently —$NR^3$—, —NH—NH—, —N=N—, —O—, —S—, —S(=O)— or —S(=O)$_2$—;

Alk is $C_{1-4}$alkanediyl; or when Y is $CR^5$ then L may also be selected from $C_{1-10}$alkyl, $C_{3-10}$alkenyl, $C_{3-10}$alkynyl, $C_{3-7}$cycloalkyl, or $C_{1-10}$alkyl substituted with one or two substituents independently selected from $C_{3-7}$cycloalkyl, indanyl, indolyl and phenyl, wherein said phenyl, indanyl and indolyl may be substituted with one, two, three, four or where possible five substituents each independently selected from halo, hydroxy, $C_{1-6}$alkyl, $C_{1-6}$alkyloxy, cyano, aminocarbonyl, $C_{1-6}$ alkyloxycarbonyl, formyl, nitro, amino, trihalomethyl, trihalomethyloxy and $C_{1-6}$alkylcarbonyl;

aryl is phenyl or phenyl substituted with one, two, three, four or five substituents each independently selected from halo, $C_{1-6}$alkyl, $C_{1-6}$alkyloxy, cyano, nitro and trifluoromethyl; and (b) one or more pharmaceutically acceptable water-soluble polymers.

2. A particle according to claim 1 having a particle size of less than 1500 μm.

3. A particle consisting of a solid dispersion, comprising:
(a) a compound selected from the group consisting of
4-[[4-[(2,4,6-trimethylphenyl)amino]-2-pyrimidinyl]amino]benzonitrile;
4-[[2-[(cyanophenyl)amino]-4-pyrimidinyl]amino]-3,5-dimethylbenzonitrile; and
(b) one or more pharmaceutically acceptable water-soluble polymers.

4. A particle according to claim 1, wherein said compound (a) is 4-[[4-[(2,4,6-trimethylphenyl)amino]-2-pyrimidinyl]amino]benzonitrile.

5. A particle according to claim 1, wherein said water-soluble polymer is a polymer that has an apparent viscosity of 1 to 5000 mPa·s when dissolved at 20° C. in an aqueous solution at 2% (w/v).

6. A particle according to claim 5, wherein the water-soluble polymer is a polymer selected from the group consisting of:
alkylcelluloses,
hydroxyalkylcelluloses,
hydroxyalkyl alkylcelluloses,
carboxyalkylcelluloses,
alkali metal salts of carboxyalkylcelluloses,
carboxyalkylalkylcelluloses,
carboxyalkylcellulose esters,
starches,
pectines,
chitin derivatives,
di-, oligo- or polysaccharides,
polyacrylic acids and the salts thereof,
polymethacrylic acids, the salts and esters thereof, methacrylate copolymers,
polyvinylalcohol, and
polyalkylene oxides.

7. A particle according to claim 6, wherein said water-soluble polymer is hydroxypropyl methylcellulose.

8. A particle according to claim 7, wherein the weight ratio of (a):(b) is in the range of 1:1 to 1:899.

9. A particle according to claim 1, consisting of a solid solution, comprising:
(a) two parts by weight of said compound (a); and
(b) three parts by weight of hydroxypropyl methylcellulose.

10. A particle according to claim 1, further comprising one or more pharmaceutically acceptable excipients.

11. A solid dispersion comprising:
(a) a compound of formula

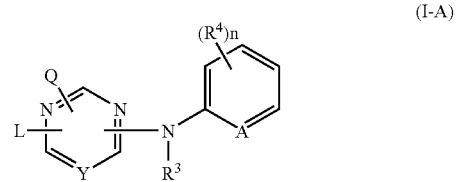

(I-A)

a N-oxide, a pharmaceutically acceptable addition salt or a stereochemically isomeric form thereof, wherein Y is $CR^5$ or N;

A is CH, $CR^4$ or N;

n is 0, 1, 2, 3 or 4;

Q is —$NR^1R^2$ or when Y is $CR^5$ then Q may also be hydrogen;

$R^1$ and $R^2$ are each independently selected from hydrogen, hydroxy, $C_{1-12}$alkyl, $C_{1-12}$alkyloxy, $C_{1-12}$alkylcarbonyl, $C_{1-12}$alkyloxycarbonyl, aryl, amino, mono- or di($C_{1-12}$alkyl)amino, mono- or di($C_{1-12}$alkyl)aminocarbonyl wherein each of the aforementioned $C_{1-12}$alkyl groups may optionally and each individually be substituted with one or two substituents each independently selected from hydroxy, $C_{1-6}$alkyloxy, hydroxy$C_{1-6}$alkyloxy, carboxyl, $C_{1-6}$alkyloxycarbonyl, cyano, amino, imino, aminocarbonyl, aminocarbonylamino, mono- or di($C_{1-6}$alkyl)amino, aryl and Het; or R¹ and R² taken together may form pyrrolidinyl, piperidinyl, morpholinyl, azido or mono- or di($C_{1-2}$alkyl)amino$C_{1-4}$alkylidene;

R³ is hydrogen, aryl, $C_{1-6}$alkylcarbonyl, $C_{1-6}$alkyl, $C_{1-6}$alkyloxycarbonyl, $C_{1-6}$alkyl substituted with $C_{1-6}$alkyloxycarbonyl; and each R⁴ independently is hydroxy, halo, $C_{1-6}$alkyl, $C_{1-6}$alkyloxy, cyano, amino-carbonyl, nitro, amino, trihalomethyl, trihalomethyloxy, or when Y is CR⁵ then R⁴ may also represent $C_{1-6}$alkyl substituted with cyano or aminocarbonyl;

R⁵ is hydrogen or $C_{1-4}$alkyl;

L is —X¹—R⁶ or —X²-Alk-R⁷ wherein

R⁶ and R⁷ each independently are phenyl or phenyl substituted with one, two, three, four or five substituents each independently selected from halo, hydroxy, $C_{1-6}$alkyl, $C_{1-6}$alkyloxy, $C_{1-6}$alkylcarbonyl, $C_{1-6}$alkyloxycarbonyl, formyl, cyano, nitro, amino, and trifluoromethyl; or when Y is CR⁵ then R⁶ and R⁷ may also be selected from phenyl substituted with one, two, three, four or five substituents each independently selected from aminocarbonyl, trihalomethyloxy and trihalomethyl; or when Y is N then R⁶ and R⁷ may also be selected from indanyl or indolyl, each of said indanyl or indolyl may be substituted with one, two, three, four or five substituents each independently selected from halo, hydroxy, $C_{1-6}$alkyl, $C_{1-6}$alkyloxy, $C_{1-6}$alkylcarbonyl, $C_{1-6}$alkyloxycarbonyl, formyl, cyano, nitro, amino, and trifluoromethyl;

X¹ and X² are each independently —NR³—, —NH—NH—, —N=N—, —O—, —S—, —S(=O)— or —S(=O)₂—;

Alk is $C_{1-4}$alkanediyl; or when Y is CR⁵ then L may also be selected from $C_{1-10}$alkyl, $C_{3-10}$alkenyl, $C_{3-10}$alkynyl, $C_{3-7}$cycloalkyl, or $C_{1-10}$alkyl substituted with one or two substituents independently selected from $C_{3-7}$cycloalkyl, indanyl, indolyl and phenyl, wherein said phenyl, indanyl and indolyl may be substituted with one, two, three, four or where possible five substituents each independently selected from halo, hydroxy, $C_{1-6}$alkyl, $C_{1-6}$alkyloxy, cyano, aminocarbonyl, $C_{1-6}$alkyloxycarbonyl, formyl, nitro, amino, trihalomethyl, trihalomethyloxy and $C_{1-6}$alkylcarbonyl;

aryl is phenyl or phenyl substituted with one, two, three, four or five substituents each independently selected from halo, $C_{1-6}$alkyl, $C_{1-6}$alkyloxy, cyano, nitro and trifluoromethyl;

Het is an aliphatic or aromatic hetercyclic radical, wherein said aliphatic heterocyclic radical is optionally substituted with an oxo group and wherein said aromatic heterocyclic radical is optionally substituted with hydroxyl; and (b) one or more pharmaceutically acceptable water-soluble polymers.

12. A solid dispersion according to claim 11, wherein the compound of formula (I-A) is a compound wherein Y is CR⁵ or N; A is CH, CR⁴ or N; n is 0, 1, 2, 3 or 4; Q is —NR¹R²; R¹ and R² are each independently selected from hydrogen, hydroxy, $C_{1-12}$alkyl, $C_{1-12}$alkyloxy, $C_{1-12}$alkylcarbonyl, $C_{1-12}$alkyloxycarbonyl, aryl, amino, mono- or di($C_{1-12}$alkyl)amino, mono- or di($C_{1-12}$alkyl)aminocarbonyl wherein each of the aforementioned $C_{1-12}$alkyl groups may optionally and each individually be substituted with one or two substituents each independently selected from hydroxy, $C_{1-6}$alkyloxy, hydroxy$C_{1-6}$alkyloxy, carboxyl, $C_{1-6}$alkyloxycarbonyl, cyano, amino, imino, aminocarbonyl, aminocarbonylamino, mono- or di($C_{1-6}$alkyl)amino, aryl and Het; or R¹ and R² taken together may form pyrrolidinyl, piperidinyl, morpholinyl, azido or mono- or di($C_{1-12}$alkyl)amino$C_{1-4}$alkylidene;

R³ is hydrogen, aryl, $C_{1-6}$alkylcarbonyl, $C_{1-6}$alkyl, $C_{1-6}$alkyloxycarbonyl, $C_{1-6}$alkyl substituted with $C_{1-6}$alkyloxycarbonyl; each R⁴ independently is hydroxy, halo, $C_{1-6}$alkyl, $C_{1-6}$alkyloxy, cyano, aminocarbonyl, nitro, amino, trihalomethyl, trihalomethyloxy; R⁵ is hydrogen or $C_{1-4}$alkyl; L is —X¹—R⁶ or —X²-Alk-R⁷ wherein R⁶ and R⁷ each independently are phenyl or phenyl substituted with one, two, three, four or five substituents each independently selected from halo, hydroxy, $C_{1-6}$alkyl, $C_{1-6}$alkyloxy, $C_{1-6}$alkylcarbonyl, $C_{1-6}$alkyloxycarbonyl, formyl, cyano, nitro, amino, and trifluoromethyl, X¹ and X² are each independently —NR³—, —NH—NH—, —N=N—, —O—, —S—, —S(=O)— or —S(=O)₂—, and Alk is $C_{1-4}$alkanediyl; aryl is phenyl or phenyl substituted with one, two, three, four or five substituents each independently selected from halo, $C_{1-6}$alkyl, $C_{1-6}$alkyloxy, cyano, nitro and trifluoromethyl; Het is an aliphatic or aromatic heterocyclic radical; said aliphatic heterocyclic radical is selected from pyrrolidinyl, piperidinyl, homopiperidinyl, piperazinyl, morpholinyl, tetrahydrofuranyl and tetrahydrothienyl wherein each of said aliphatic heterocyclic radical may optionally be substituted with an oxo group; and said aromatic heterocyclic radical is selected from pyrrolyl, furanyl, thienyl, pyridyl, pyrimidinyl, pyrazinyl and pyridazinyl wherein each of said aromatic heterocyclic radical may optionally be substituted with hydroxy.

13. A solid dispersion according to claim 11, wherein the compound of formula (I-A) is selected from 4-[[4-amino-6-[(2,6-dichlorophenyl)methyl]-2-pyrimidinyl]amino]benzonitrile;

6-[(2,6-dichlorophenyl)methyl]-N2-(4-fluorophenyl)-2,4-pyrimidinediamine;

4-[[4-[(2,4-dichlorophenyl)methyl]-6-[(4-hydroxybutyl)amino]-2-pyrimidinyl]amino]benzonitrile;

4-[[4-[(2,6-dichlorophenyl)methyl]-6-[(3-hydroxypropyl)amino]-2-pyrimidinyl]amino]benzonitrile;

N-[2-[(4-cyanophenyl)amino]-6-[(2,6-dichlorophenyl)methyl]-4-pyrimidinyl]-acetamide;

N-[2-[(4-cyanophenyl)amino]-6-[(2,6-dichlorophenyl)methyl]-4-pyrimidinyl]-butanamide;

4-[[2-amino-6-(2,6-dichlorophenoxy)-4-pyrimidinyl]amino]benzonitrile;

4-[[4-[(2,6-dichlorophenyl)methyl]-6-[(2-hydroxy-2-phenylethyl)amino]-2-pyrimidinyl]amino]benzonitrile;

4-[[4-[(2,6-dichlorophenyl)methyl]-6-[[3-(2-oxo-1-pyrrolidinyl)propyl]amino]-2-pyrimidinyl]amino]benzonitrile;

4-[[4-[(2,6-dichlorophenyl)methyl]-6-[[2-(2-hydroxyethoxy)ethyl]amino]-2-pyrimidinyl]amino]benzontrile monohydrochloride;

4-[[4-[(2,6-dichlorophenyl)methyl]-6-[(2,3-dihydroxypropyl)amino]-2-pyrimidinyl]amino]benzonitrile;

4-[[4-[(2,6-dichlorophenyl)methyl]-6-(hydroxyamino)-2-pyrimidinyl]amino]-benzonitrile;

4-[[4-[(2-cyanoethyl)amino]-6-[(2,6-dichlorophenyl)methyl]-2-pyrimidinyl]amino]-benzonitrile;

4-[[4-[(2,6-dichlorophenyl)methyl]-6-[[2-(1-pyrrolidinyl)ethyl]amino]-2-pyrimidinyl]amino]benzonitrile;

4-[[4-amino-6-[(2,6-dichlorophenyl)methyl]-5-methyl-2-pyrimidinyl]amino]-benzonitrile;

N2-(4-bromophenyl)-6-[(2,6-dichlorophenyl)methyl]-5-methyl-2,4-pyrimidinediamine;

4-[[4-[(2,4,6-trimethylphenyl)amino]-2-pyrimidinyl]
amino]benzonitrile;
4-[[2-[(2,4,6-trimethylphenyl)amino]-4-pyrimidinyl]
amino]benzonitrile;
4-[[4-[(2,6-dimethylphenyl)amino]-2-pyrimidinyl]
amino]benzonitrile;
4-[[4-(2,4,6-trimethylphenoxy)-2-pyrimidinyl]amino]
benzonitrile;
4-[[4-[(2,6-dichlorophenyl)thio]-2-pyrimidinyl]amino]
benzonitrile;
4-[[4-[[2,6-dibromo-4-(1-methylethyl)phenyl]amino]-2-
pyrimidinyl]amino]-benzonitrile;
4-[[4-[[2,6-dichloro-4-(trifluoromethyl)phenyl]amino]-2-
pyrimidinyl]amino]-benzonitrile;
4-[[4-[(2,4-dichloro-6-methylphenyl)amino]-2-pyrimidi-
nyl]amino]benzonitrile;
4-[[2-[(cyanophenyl)amino]-4-pyrimidinyl]amino]-3,5-
dimethylbenzonitrile;
4-[[4-[(2,4-dibromo-6-fluorophenyl)amino]-2-pyrimidi-
nyl]amino]benzonitrile;
4-[[4-amino-6-[(2,6-dichlorophenyl)methyl]-5-methyl-2-
pyrimidinyl]amino]-benzeneacetonitrile;
4-[[4-[methyl(2,4,6-trimethylphenyl)amino]-2-pyrimidi-
nyl]amino]benzonitrile;
4-[[4-[(2,4,6-trichlorophenyl)amino]-2-pyrimidinyl]
amino]benzonitrile;
4-[[4-[(2,4,6-trimethylphenyl)thio]-2-pyrimidinyl]amino]
benzonitrile;
4-[[4-[(2,4,6-trimethylphenyl)amino-2-pyrimidinyl]
amino]benzonitrile;
4-[[4-amino-6-[(2,4,6-trimethylphenyl)amino]-2-pyrim-
idinyl]amino]benzonitrile;
4-[[2-amino-6-[(2,4,6-trimethylphenyl)amino]-4-pyrim-
idinyl]amino]benzonitrile;
4-[[4-(2-bromo-4-chloro-6-methylphenoxy)-2-pyrimidi-
nyl]amino]benzonitrile;
4-[[4-[(4-chloro-2,6-dimethylphenyl)amino]-2-pyrimidi-
nyl]amino]benzonitrile;
3,5-dichloro-4-[[2-[(4-cyanophenyl)amino]-4-pyrimidi-
nyl]amino]benzonitrile;
4-[[4-[[2,6-dichloro-4-(trifluoromethoxy)phenyl]amino]-
2-pyrimidinyl]amino]-benzonitrile;
4-[[4-[(2,4-dibromo-3,6-dichlorophenyl)amino]-2-pyrim-
idinyl]amino]benzonitrile;
4-[[4-[(2,6-dibromo-4-propylphenyl)amino]-2-pyrimidi-
nyl]amino]benzonitrile;
4-[[4-[(2,4,6-trimethylphenyl)amino]-2-pyrimidinyl]
amino]benzamide;
4-[[4-[(4-(1,1-dimethylethyl)-2,6-dimethylphenyl)
amino]-2-pyrimidinyl]amino]-benzonitrile;
4-[[2-[(4-cyanophenyl)amino]-4-pyrimidinyl]oxy]-3,5-
dimethylbenzonitrile;
4-[[4-[(4-chloro-2,6-dimethylphenyl)amino]-5-methyl-2-
pyrimidinyl]amino]-benzonitrile;
4-[[2-[(4-cyanophenyl)amino]-5-methyl-4-pyrimidinyl]
amino]-3,5-dimethyl benzonitrile;
4-[[4-[[4-(1,1-dimethylethyl)-2,6-dimethylphenyl]
amino]-5-methyl-2-pyrimidinyl]amino]benzonitrile;
4-[[4-[(4-bromo-2,6-dimethylphenyl)amino]-5-methyl-2-
pyrimidinyl]amino]-benzonitrile;
4-[[5-methyl-4-[(2,4,6-trimethylphenyl)thio]-2-pyrimidi-
nyl]amino]benzonitrile;
4-[[4-[(2,6-dibromo-4-propylphenyl)amino]-5-methyl-2-
pyrimidinyl]amino]-benzonitrile;
4-[[4-[(2,4,6-trimethylphenyl)amino]-2-pyrimidinyl]
amino]benzamide, N3-oxide;

N2-(4-chlorophenyl)-N4-(2,4,6-trimethylphenyl)-2,4-py-
rimidinediamine;
4-[[4-[[2,6-dibromo-4-(1-methylethyl)phenyl]amino]-5-
methyl-2-pyrimidinyl]amino]benzonitrile;
4-[[2-[(4-cyanophenyl)amino]-5-methyl-4-pyrimidinyl]
amino]-3,5-dimethyl benzonitrile;
4-[[4-[(phenylmethyl)amino]-2-pyrimidinyl]amino]ben-
zonitrile;
4-[[4-amino-6-(2,6-dimethylphenoxy)-1,3,5-triazin-2-yl]
amino]benzonitrile;
4-[[4-amino-6-[(2-chloro-6-methylphenyl)amino]-1,3,5-
triazin-2-yl]amino]benzonitrile;
4-[[4-amino-6-[(2,4,6-trimethylphenyl)amino]-1,3,5-tri-
azin-2-yl]amino]-benzonitrile;
4-[[4-(hydroxyamino)-6-[(2,4,6-trimethylphenyl)amino]-
1,3,5-triazin-2-yl]amino]-benzonitrile;
4-[[4-amino-6-[(2-ethyl-6-methylphenyl)amino]-1,3,5-
triazin-2-yl]amino]benzonitrile;
4-[[4-amino-6-[(2,6-dichlorophenyl)thio]-1,3,5-triazin-2-
yl]amino]benzonitrile;
4-[[4-(hydroxyamino)-6-[(2,4,6-trichlorophenyl)amino]-
1,3,5-triazin-2-yl]amino]-benzonitrile;
4-[[4-amino-6-(2,4,6-trimethylphenoxy)-1,3,5-triazin-2-
yl]amino]benzonitrile;
4-[[4-(hydroxyamino)-6-(2,4,6-trimethylphenoxy)-1,3,5-
triazin-2-yl]amino]-benzonitrile;
4-[[4-amino-6-[(2,4-dichloro-6-methylphenyl)amino]-1,
3,5-triazin-2-yl]amino]-benzonitrile;
4-[[4-[(2,4-dichloro-6-methylphenyl)amino]-6-(hy-
droxyamino)-1,3,5-triazin-2-yl]-amino]benzontrile;
4-[[4-(hydroxyamino)-6-(2,4,6-trichlorophenoxy)-1,3,5-
triazin-2-yl]amino]benzonitrile trifluoroacetate (1:1);
4-[[4-(4-acetyl-2,6-dimethylphenoxy)-6-amino-1,3,5-tri-
azin-2-yl]amino]benzonitrile;
4-[[4-amino-6-(2,4,6-tribromophenoxy)-1,3,5-triazin-2-
yl]amino]benzonitrile;
4-[[4-amino-6-(4-nitro-2,6-dimethylphenoxy)-1,3,5-tri-
azin-2-yl]amino]benzonitrile;
4-[[4-amino-6-(2,6-dibromo-4-methylphenoxy)-1,3,5-tri-
azin-2-yl]amino]benzonitrile;
4-[[4-amino-6-(4-formyl-2,6-dimethylphenoxy)-1,3,5-
triazin-2-yl]amino]benzonitrile;
4-[[4-amino-6-[(2,4-dichlorophenyl)thio]-1,3,5-triazin-2-
yl]amino]benzonitrile;
4-[[4-[(5-acetyl-2,3-dihydro-7-methyl-1H-inden-4-yl)
oxy]-6-amino-1,3,5-triazin-2-yl]amino]benzonitrile;
4-[[4-amino-6-[(4-bromo-2-chloro-6-methylphenyl)
amino]-1,3,5-triazin-2-yl]amino]-benzonitrile;
4-[[4-amino-6-[(2-chloro-4,6-dimethylphenyl)amino]-1,
3,5-triazin-2-yl]amino]-benzonitrile;
4-[[4-amino-6-[[2,4-dichloro-6-(trifluoromethyl)phenyl]
amino]-1,3,5-triazin-2-yl]-amino]benzonitrile;
4-[[4-amino-6-[methyl(2,4,6-trimethylphenyl)amino]-1,
3,5-triazin-2-yl]amino]benzonitrile;
4-[[4-amino-6-[(2,6-dibromo-4-methylphenyl)amino]-1,
3,5-triazin-2-yl]amino]benzonitrile;
4-[[4-amino-6-[[2,6-dibromo-4-(1-methylethyl)phenyl]
amino]-1,3,5-triazin-2-yl]-amino]benzonitrile;
a N-oxide, a pharmaceutically acceptable addition salt
thereof.

14. A solid dispersion according to claim 13, wherein the compound of formula (I-A) is 4-[[4-[(2,4,6-trimethylphenyl) amino]-2-pyrimidinyl]amino]benzonitrile; a N-oxide, or a pharmaceutically acceptable addition salt thereof.

15. A solid dispersion according to claim 13, wherein the compound of formula (I-A) is 4-[[2-[(cyanophenyl)amino]-

4-pyrimidinyl]amino]-3,5-dimethylbenzonitrile;a N-oxide, or a pharmaceutically acceptable addition salt thereof.

16. A solid dispersion according to any one of claims 11–15, wherein the water-soluble polymer is a polymer that has an apparent viscosity of 1 to 5000 mPa·s when dissolved at 20° C. in an aqueous solution at 2% (w/v).

17. A solid dispersion according to any one of claims 11–15, wherein the water-soluble polymer is selected from the group comprising
 alkylcelluloses,
 hydroxyalkylcelluloses,
 hydroxyalkyl alkylcelluloses,
 carboxyalkylcelluloses,
 alkali metal salts of carboxyalkylcelluloses,
 carboxyalkylalkylcelluloses,
 carboxyalkylcellulose esters,
 starches,
 pectines,
 chitin derivates,
 di-, oligo- or polysaccharides,
 polyacrylic acids and the salts thereof,
 polymethacrylic acids, the salts and esters thereof, methacrylate copolymers,
 polyvinylalcohol,
 polyalkylene oxides such as polyethylene oxide and polypropylene oxide and copolymers of ethylene oxide and propylene oxide.

18. A solid dispersion according to claim 17, wherein the water-soluble polymer is selected from the group comprising methylcellulose; hydroxymethylcellulose; hydroxyethylcellulose; hydroxypropylcellulose; hydroxybutylcellulose; hydroxyethyl methylcellulose; hydroxypropyl methylcellulose; carboxymethylcellulose; sodium carboxymethylcellulose; carboxymethylethylcellulose; sodium carboxymethylamylopectine; chitosan; trehalose; cyclodextrins or a derivative thereof, alginic acid, alkali metal and ammonium salts thereof, carrageenans; galactomannans; tragacanth; agar—agar; gummi arabicum; guar gummi; xanthan gummi; polyethylene oxide; polypropylene oxide; and copolymers of ethylene oxide and propylene oxide.

19. A solid dispersion according to claim 17, wherein the water-soluble polymer is selected from Eudragit E® and hydroxypropyl methylcellulose.

20. A solid dispersion according to any one of claim 17, wherein the water-soluble polymer is an aminoalkyl methacrylate copolymer.

21. A solid dispersion according to any one of claim 17, wherein the water-soluble polymer is hydroxypropyl methylcellulose.

22. A solid dispersion according to claim 21 wherein the hydroxypropyl methylcellulose has an apparent viscosity from about 1 to about 100 mPa·s when dissolved at 20° C. in an aqueous solution at 2% (w/v).

23. A solid dispersion according to claim 22, wherein the hydroxypropyl methylcellulose has an apparent viscosity from about 3 to about 15 mPa·s when dissolved at 20° C. in an aqueous solution at 2% (w/v).

24. A solid dispersion according to claim 23, wherein the hydroxypropyl methylcellulose has an apparent viscosity of about 5 mPa·s when dissolved at 20° C. in an aqueous solution at 2% (w/v).

25. A solid dispersion according to claim 24, wherein the hydroxypropyl methylcellulose is hydroxypropyl methylcellulose HPMC 2910 5 mPa·s.

26. A solid dispersion according to 11, wherein the weight-by-weight ratio of (a): (b) is in the range of 1:1 to 1:899.

27. A solid dispersion according to claim 26, wherein the weight-by-weight ratio of (a):(b) is in the range of 1:1 to 1:100.

28. A solid dispersion according to claim 27, wherein the weight-by-weight ratio of (a):(b) is in the range of 1:1 to 1:5.

29. A solid dispersion according to claim 28, wherein the weight-by-weight ratio of (a):(b) is in the range of from about 1:1 to about 1:3.

30. A solid dispersion according to claim 28, wherein the weight-by-weight ratio of (a):(b) is in the range of about 1:3 to about 1:5.

31. A solid dispersion according to claim 29 wherein the weight-by-weight ratio of (a):(b) is in the range of about 1:1 to about 1:1.5.

32. A solid dispersion according to claim 29 wherein the weight-by-weight ratio of (a):(b) is in the range of about 1:1.5 to about 1:3.

* * * * *